(12) United States Patent
Hamner et al.

(10) Patent No.: US 11,857,778 B2
(45) Date of Patent: Jan. 2, 2024

(54) SYSTEMS AND METHODS FOR TREATING INFLAMMATORY BOWEL DISEASE THROUGH PERIPHERAL NERVE STIMULATION

(71) Applicant: Cala Health, Inc., Burlingame, CA (US)

(72) Inventors: Samuel Richard Hamner, San Francisco, CA (US); Erika Kristine Ross, San Mateo, CA (US); Kathryn H. Rosenbluth, San Francisco, CA (US)

(73) Assignee: Cala Health, Inc., San Mateo, CA (US)

( * ) Notice: Subject to any disclaimer, the term of this patent is extended or adjusted under 35 U.S.C. 154(b) by 419 days.

(21) Appl. No.: 16/962,810

(22) PCT Filed: Jan. 17, 2019

(86) PCT No.: PCT/US2019/013966
§ 371 (c)(1),
(2) Date: Jul. 16, 2020

(87) PCT Pub. No.: WO2019/143790
PCT Pub. Date: Jul. 25, 2019

(65) Prior Publication Data
US 2021/0252278 A1    Aug. 19, 2021

Related U.S. Application Data

(60) Provisional application No. 62/618,557, filed on Jan. 17, 2018.

(51) Int. Cl.
*A61N 1/04* (2006.01)
*A61N 1/36* (2006.01)
*A61N 1/32* (2006.01)

(52) U.S. Cl.
CPC ........... *A61N 1/0456* (2013.01); *A61N 1/323* (2013.01); *A61N 1/36007* (2013.01);
(Continued)

(58) Field of Classification Search
CPC .. A61N 1/0456; A61N 1/323; A61N 1/36007; A61N 1/36031; A61N 1/36034;
(Continued)

(56) References Cited

U.S. PATENT DOCUMENTS 3,204,637 A   9/1965  Frank et al.
3,870,051 A   3/1975  Brindley
(Continued)

FOREIGN PATENT DOCUMENTS

CN    1135722      11/1996
CN    101022849    8/2007
(Continued)

OTHER PUBLICATIONS

U.S. Appl. No. 15/277,946, filed Sep. 27, 2016, Rosenbluth et al.
(Continued)

*Primary Examiner* — Amanda K Hulbert
(74) *Attorney, Agent, or Firm* — Knobbe Martens Olson & Bear LLP

(57) ABSTRACT

Systems and methods for treating symptoms of an inflammatory gastrointestinal disease in a patient with transcutaneous stimulation of a peripheral nerve are disclosed. The method can include any number of positioning a first peripheral nerve effector on the patient's skin to stimulate the peripheral nerve of the patient, delivering a first electrical nerve stimulation signal transcutaneously to the peripheral nerve through the first peripheral nerve effector, and modifying at least one brain or spinal cord autonomic feedback loop relating to release of neurotransmitters from the autonomic nervous system that modulate synthesis of inflam-
(Continued)

matory biomarkers and reduce inflammation relating to the inflammatory gastrointestinal disease.

20 Claims, 38 Drawing Sheets

(52) U.S. Cl.
CPC ..... *A61N 1/36031* (2017.08); *A61N 1/36034* (2017.08); *A61N 1/36036* (2017.08)

(58) Field of Classification Search
CPC ................ A61N 1/36036; A61N 2/002; A61B 2018/00494; A61B 2562/0219; A61B 2562/0223; A61B 2562/0247; A61B 5/01; A61B 5/021; A61B 5/02405; A61B 5/026; A61B 5/0533; A61B 5/0816; A61B 5/1038; A61B 5/1107; A61B 5/1112; A61B 5/1118; A61B 5/20; A61B 5/318; A61B 5/4035; A61B 5/42; A61B 5/4812; A61B 5/4836; A61B 5/72

See application file for complete search history.

(56) References Cited

U.S. PATENT DOCUMENTS

| | | |
|---|---|---|
| 4,300,575 A | 11/1981 | Wilson |
| 4,458,696 A | 7/1984 | Larimore |
| 4,461,075 A | 7/1984 | Bailey |
| 4,539,996 A | 9/1985 | Engel |
| 4,569,351 A | 2/1986 | Tang |
| 4,582,049 A | 4/1986 | Ylvisaker |
| 4,729,377 A | 3/1988 | Granek et al. |
| 4,739,764 A | 4/1988 | Lue et al. |
| 4,763,659 A | 8/1988 | Dunseath, Jr. |
| 4,771,779 A | 9/1988 | Tanagho et al. |
| 4,981,146 A | 1/1991 | Bertolucci |
| 4,982,432 A | 1/1991 | Clark et al. |
| 5,003,978 A | 4/1991 | Dunseath, Jr. |
| 5,052,391 A | 10/1991 | Silverstone et al. |
| 5,070,862 A | 12/1991 | Berlant |
| 5,137,507 A | 8/1992 | Park |
| 5,330,516 A | 7/1994 | Nathan |
| 5,397,338 A | 3/1995 | Grey et al. |
| 5,514,175 A | 5/1996 | Kim et al. |
| 5,540,235 A | 7/1996 | Wilson |
| 5,562,707 A | 10/1996 | Prochazka et al. |
| 5,562,717 A | 10/1996 | Tippey et al. |
| 5,573,011 A | 11/1996 | Felsing |
| 5,575,294 A | 11/1996 | Perry et al. |
| 5,606,968 A | 3/1997 | Mang |
| 5,643,173 A | 7/1997 | Welles |
| 5,775,331 A | 7/1998 | Raymond et al. |
| 5,833,709 A | 11/1998 | Rise et al. |
| 5,833,716 A | 11/1998 | Bar-Or et al. |
| 5,899,922 A | 5/1999 | Loos |
| 6,016,449 A | 1/2000 | Fischell et al. |
| 6,076,018 A | 6/2000 | Sturman et al. |
| 6,081,744 A | 6/2000 | Loos |
| 6,161,044 A | 12/2000 | Silverstone |
| 6,178,352 B1 | 1/2001 | Gruzdowich et al. |
| 6,351,674 B2 | 2/2002 | Silverstone |
| 6,366,813 B1 | 4/2002 | DiLorenzo |
| 6,445,955 B1 | 9/2002 | Michelson et al. |
| 6,449,512 B1 | 9/2002 | Boveja |
| 6,453,204 B1 | 9/2002 | Rhoads |
| 6,505,074 B2 | 1/2003 | Boveja et al. |
| 6,546,290 B1 | 4/2003 | Shloznikov |
| 6,564,103 B2 | 5/2003 | Fischer et al. |
| 6,579,270 B2 | 6/2003 | Sussman et al. |
| 6,652,449 B1 | 11/2003 | Gross et al. |
| 6,678,548 B1 | 1/2004 | Echauz et al. |
| 6,701,185 B2 | 3/2004 | Burnett et al. |
| 6,704,603 B1 | 3/2004 | Gesotti |
| 6,731,987 B1 | 5/2004 | McAdams et al. |
| 6,735,474 B1 | 5/2004 | Loeb et al. |
| 6,735,480 B2 | 5/2004 | Giuntoli et al. |
| 6,788,976 B2 | 9/2004 | Gesotti |
| 6,819,956 B2 | 11/2004 | DiLorenzo |
| 6,829,510 B2 | 12/2004 | Nathan et al. |
| 6,836,684 B1 | 12/2004 | Rijkhoff et al. |
| 6,862,480 B2 | 3/2005 | Cohen et al. |
| 6,892,098 B2 | 5/2005 | Ayal et al. |
| 6,937,905 B2 | 8/2005 | Carroll et al. |
| 6,959,215 B2 | 10/2005 | Gliner et al. |
| 6,959,216 B2 | 10/2005 | Faghri |
| 6,988,005 B2 | 1/2006 | McGraw et al. |
| 7,010,352 B2 | 3/2006 | Hogan |
| 7,089,061 B2 | 8/2006 | Grey |
| 7,146,220 B2 | 12/2006 | Dar et al. |
| 7,162,305 B2 | 1/2007 | Tong et al. |
| 7,171,266 B2 | 1/2007 | Gruzdowich et al. |
| 7,177,694 B2 | 2/2007 | Elbaum |
| 7,177,703 B2 | 2/2007 | Boveja et al. |
| 7,209,787 B2 | 4/2007 | DiLorenzo |
| 7,228,178 B2 | 6/2007 | Carroll et al. |
| 7,231,254 B2 | 6/2007 | DiLorenzo |
| 7,236,830 B2 | 6/2007 | Gliner |
| 7,254,444 B2 | 8/2007 | Moore et al. |
| 7,277,758 B2 | 10/2007 | DiLorenzo |
| 7,324,851 B1 | 1/2008 | DiLorenzo |
| 7,326,235 B2 | 2/2008 | Edwards |
| 7,328,068 B2 | 2/2008 | Spinelli et al. |
| 7,349,739 B2 | 3/2008 | Harry et al. |
| 7,353,064 B2 | 4/2008 | Gliner et al. |
| 7,369,896 B2 | 5/2008 | Gesotti |
| 7,499,747 B2 | 3/2009 | Kieval et al. |
| 7,529,582 B1 | 5/2009 | DiLorenzo |
| 7,558,610 B1 | 7/2009 | Odderson |
| 7,636,602 B2 | 12/2009 | Baru Fassio et al. |
| 7,643,880 B2 | 1/2010 | Tanagho et al. |
| 7,643,882 B2 | 1/2010 | Boston |
| 7,647,112 B2 | 1/2010 | Tracey et al. |
| 7,650,190 B2 | 1/2010 | Zhou et al. |
| 7,657,317 B2 | 2/2010 | Thacker et al. |
| 7,742,820 B2 | 6/2010 | Wyler et al. |
| 7,761,166 B2 | 7/2010 | Giftakis et al. |
| 7,769,464 B2 | 8/2010 | Gerber et al. |
| 7,857,771 B2 | 12/2010 | Alwan et al. |
| 7,899,527 B2 | 3/2011 | Yun et al. |
| 7,899,556 B2 | 3/2011 | Nathan et al. |
| 7,917,201 B2 | 3/2011 | Gozani et al. |
| 7,930,034 B2 | 4/2011 | Gerber |
| 7,949,403 B2 | 5/2011 | Palermo et al. |
| 7,957,814 B2 | 6/2011 | Goetz et al. |
| 7,974,696 B1 | 7/2011 | DiLorenzo |
| 7,974,698 B2 | 7/2011 | Tass et al. |
| 7,991,476 B2 | 8/2011 | Nachum |
| 7,996,088 B2 | 8/2011 | Marrosu et al. |
| 7,998,092 B2 | 8/2011 | Avni et al. |
| 8,000,796 B2 | 8/2011 | Tass et al. |
| 8,025,632 B2 | 9/2011 | Einarsson |
| 8,046,083 B2 | 10/2011 | Tegenthoff et al. |
| 8,075,499 B2 | 12/2011 | Nathan et al. |
| 8,086,318 B2 | 12/2011 | Strother et al. |
| 8,121,694 B2 | 2/2012 | Molnar et al. |
| 8,145,316 B2 | 3/2012 | Deem et al. |
| 8,165,668 B2 | 4/2012 | Dacey, Jr. et al. |
| 8,165,685 B1 | 4/2012 | Knutson et al. |
| 8,170,658 B2 | 5/2012 | Dacey, Jr. et al. |
| 8,175,718 B2 | 5/2012 | Wahlgren et al. |
| 8,187,209 B1 | 5/2012 | Guiffrida et al. |
| 8,195,287 B2 | 6/2012 | Dacey, Jr. et al. |
| 8,209,036 B2 | 6/2012 | Nathan et al. |
| 8,219,188 B2 | 7/2012 | Craig |
| 8,233,988 B2 | 7/2012 | Errico et al. |
| 8,260,439 B2 | 9/2012 | Diubaldi et al. |
| 8,265,763 B2 | 9/2012 | Fahey |
| 8,301,215 B2 | 10/2012 | Lee |
| 8,306,624 B2 | 11/2012 | Gerber et al. |
| 8,308,665 B2 | 11/2012 | Harry et al. |
| 8,313,443 B2 | 11/2012 | Tom |
| 8,326,432 B2 | 12/2012 | Kalisek |

(56) References Cited

U.S. PATENT DOCUMENTS

| | | |
|---|---|---|
| 8,343,026 B2 | 1/2013 | Gardiner et al. |
| 8,364,257 B2 | 1/2013 | Van Den Eerenbeemd et al. |
| 8,374,701 B2 | 2/2013 | Hyde et al. |
| 8,380,314 B2 | 2/2013 | Panken et al. |
| 8,382,688 B2 | 2/2013 | Dar et al. |
| 8,391,970 B2 | 3/2013 | Tracey et al. |
| 8,396,556 B2 | 3/2013 | Libbus et al. |
| 8,409,116 B2 | 4/2013 | Wang et al. |
| 8,412,338 B2 | 4/2013 | Faltys |
| 8,414,507 B2 | 4/2013 | Asada |
| 8,417,351 B2 | 4/2013 | Kilger |
| 8,428,719 B2 | 4/2013 | Napadow |
| 8,430,805 B2 | 4/2013 | Burnett et al. |
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |
| 8,473,064 B2 | 6/2013 | Castel et al. |
| 8,548,594 B2 | 10/2013 | Thimineur et al. |
| 8,571,687 B2 | 10/2013 | Libbus et al. |
| 8,581,731 B2 | 11/2013 | Purks et al. |
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,738,143 B2 | 5/2014 | Tucker et al. |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,431 B2 | 12/2015 | Holzhacker |
| 9,220,895 B2 | 12/2015 | Siff et al. |
| 9,227,056 B1 | 1/2016 | Heldman et al. |
| 9,238,137 B2 | 1/2016 | Einav et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,311,686 B2 | 4/2016 | Roush et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,213 B2 | 5/2016 | Otsamo et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,387,338 B2 | 7/2016 | Burnett |
| 9,393,430 B2 | 7/2016 | Demers et al. |
| 9,408,683 B2 | 8/2016 | St. Anne et al. |
| 9,414,776 B2 | 8/2016 | Sillay et al. |
| 9,415,205 B2 | 8/2016 | Lasko et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,586,038 B1 | 3/2017 | Kosierkiewicz |
| 9,597,509 B2 | 3/2017 | Hoffer et al. |
| 9,610,442 B2 | 4/2017 | Yoo et al. |
| 9,610,459 B2 | 4/2017 | Burnett et al. |
| 9,615,797 B2 | 4/2017 | John |
| 9,630,004 B2 | 4/2017 | Rajguru et al. |
| 9,649,486 B2 | 5/2017 | Holzhacker |
| 9,656,070 B2 | 5/2017 | Gozani et al. |
| 9,669,211 B2 | 6/2017 | Wijting et al. |
| 9,675,800 B2 | 6/2017 | Li et al. |
| 9,675,801 B2 | 6/2017 | Kong et al. |
| 9,707,393 B2 | 7/2017 | Hsueh et al. |
| 9,731,126 B2 | 8/2017 | Ferree et al. |
| 9,757,584 B2 | 9/2017 | Burnett |
| 9,782,584 B2 | 10/2017 | Cartledge et al. |
| 9,802,041 B2 | 10/2017 | Wong et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,884,179 B2 | 2/2018 | Bouton et al. |
| 9,924,899 B2 | 3/2018 | Pracar et al. |
| 9,956,395 B2 | 5/2018 | Bikson et al. |
| 9,974,478 B1 | 5/2018 | Brokaw et al. |
| 9,980,659 B2 | 5/2018 | Sadeghian-Motahar et al. |
| 9,992,918 B2 | 6/2018 | Watanabe et al. |
| 10,004,900 B2 | 6/2018 | Kent et al. |
| 10,016,600 B2 | 7/2018 | Creasey et al. |
| 10,022,545 B1 | 7/2018 | Giuffrida |

(56) References Cited

U.S. PATENT DOCUMENTS

| | | |
|---|---|---|
| 10,028,695 B2 | 7/2018 | Machado et al. |
| 10,045,740 B2 | 8/2018 | John |
| 10,046,161 B2 | 8/2018 | Biasiucci et al. |
| 10,076,656 B2 | 9/2018 | Dar et al. |
| 10,080,885 B2 | 9/2018 | Nathan et al. |
| 10,112,040 B2 | 10/2018 | Herb et al. |
| 10,118,035 B2 | 11/2018 | Perez et al. |
| 10,130,809 B2 | 11/2018 | Cartledge et al. |
| 10,130,810 B2 | 11/2018 | Ferree et al. |
| 10,137,025 B2 | 11/2018 | Fior et al. |
| 10,173,060 B2 | 1/2019 | Wong et al. |
| 10,179,238 B2 | 1/2019 | Wong et al. |
| 10,213,593 B2 | 2/2019 | Kaplan et al. |
| 10,213,602 B2 | 2/2019 | Ironi et al. |
| 10,232,174 B2 | 3/2019 | Simon et al. |
| 10,252,053 B2 | 4/2019 | Page et al. |
| 10,285,646 B1 | 5/2019 | Grant et al. |
| 10,286,210 B2 | 5/2019 | Yoo |
| 10,293,159 B2 | 5/2019 | Kong et al. |
| 10,335,594 B2 | 7/2019 | Lin et al. |
| 10,335,595 B2 | 7/2019 | Ferree et al. |
| 10,342,977 B2 | 7/2019 | Raghunathan |
| 10,398,896 B2 | 9/2019 | Lin et al. |
| 10,456,573 B1 | 10/2019 | Feinstein et al. |
| 10,463,854 B2 | 11/2019 | Perez |
| 10,500,396 B2 | 12/2019 | Tamaki et al. |
| 10,537,732 B2 | 1/2020 | Nachum et al. |
| 10,549,093 B2 | 2/2020 | Wong et al. |
| 10,556,107 B2 | 2/2020 | Yoo et al. |
| 10,561,839 B2 | 2/2020 | Wong et al. |
| 10,603,482 B2 | 3/2020 | Hamner et al. |
| 10,610,114 B2 | 4/2020 | Buckley et al. |
| 10,625,074 B2 | 4/2020 | Rosenbluth et al. |
| 10,632,312 B2 | 4/2020 | Ziv |
| 10,661,082 B2 | 5/2020 | Kerselaers |
| 10,722,709 B2 | 7/2020 | Yoo et al. |
| 10,765,856 B2 | 9/2020 | Wong et al. |
| 10,773,079 B2 | 9/2020 | Keller et al. |
| 10,780,269 B2 | 9/2020 | Gozani et al. |
| 10,786,669 B2 | 9/2020 | Rajguru et al. |
| 10,814,130 B2 | 10/2020 | Wong et al. |
| 10,814,131 B2 | 10/2020 | Goldwasser et al. |
| 10,835,736 B2 | 11/2020 | Horter et al. |
| 10,850,090 B2 | 12/2020 | Rosenbluth et al. |
| 10,870,002 B2 | 12/2020 | Wybo et al. |
| 10,905,879 B2 | 2/2021 | Wong et al. |
| 10,918,853 B2 | 2/2021 | Creasey et al. |
| 10,940,311 B2 | 3/2021 | Gozani et al. |
| 10,945,879 B2 | 3/2021 | Black et al. |
| 10,960,207 B2 | 3/2021 | Wong et al. |
| 10,967,177 B2 | 4/2021 | Lee |
| 11,026,835 B2 | 6/2021 | Black et al. |
| 11,033,206 B2 | 6/2021 | Roh |
| 11,033,731 B2 | 6/2021 | Jeffery et al. |
| 11,033,736 B2 | 6/2021 | Edgerton et al. |
| 11,058,867 B2 | 7/2021 | Nathan et al. |
| 11,077,300 B2 | 8/2021 | McBride |
| 11,077,301 B2 | 8/2021 | Creasey et al. |
| 11,141,586 B2 | 10/2021 | Campean et al. |
| 11,141,587 B2 | 10/2021 | Campean et al. |
| 11,160,971 B2 | 11/2021 | Sharma et al. |
| 11,213,681 B2 | 1/2022 | Raghunathan |
| 11,224,742 B2 | 1/2022 | Burnett |
| 11,247,040 B2 | 2/2022 | Ferree et al. |
| 11,247,053 B2 | 2/2022 | Rajguru et al. |
| 11,266,836 B2 | 3/2022 | Charlesworth et al. |
| 11,331,480 B2 | 5/2022 | Hamner et al. |
| 11,344,722 B2 | 5/2022 | Wong et al. |
| 11,357,981 B2 | 6/2022 | Moaddeb et al. |
| 11,628,300 B2 | 4/2023 | Rajguru et al. |
| 2001/0020177 A1 | 9/2001 | Gruzdowich et al. |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0127939 A1 | 7/2004 | Grey et al. |
| 2004/0133249 A1 | 7/2004 | Gesotti |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0060009 A1 | 3/2005 | Geotz |
| 2005/0065553 A1 | 3/2005 | Ben Ezra et al. |
| 2005/0075502 A1 | 4/2005 | Shafer |
| 2005/0171577 A1 | 8/2005 | Cohen et al. |
| 2005/0222626 A1 | 10/2005 | DiLorenzo |
| 2005/0234309 A1 | 10/2005 | Klapper |
| 2005/0240241 A1 | 10/2005 | Yun et al. |
| 2006/0047326 A1 | 3/2006 | Wheeler |
| 2006/0052726 A1 | 3/2006 | Weisz et al. |
| 2006/0074450 A1 | 4/2006 | Boveja et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0203534 A1 | 8/2007 | Tapper |
| 2007/0207193 A1 | 9/2007 | Zasler et al. |
| 2007/0255319 A1 | 11/2007 | Greenberg et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0033259 A1 | 2/2008 | Manto et al. |
| 2008/0033504 A1 | 2/2008 | Bertolucci |
| 2008/0051839 A1 | 2/2008 | Libbus et al. |
| 2008/0051845 A1 | 2/2008 | Mentelos |
| 2008/0058773 A1 | 3/2008 | John |
| 2008/0058871 A1 | 3/2008 | Libbus et al. |
| 2008/0058893 A1 | 3/2008 | Noujokat |
| 2008/0097564 A1 | 4/2008 | Lathrop |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208282 A1 | 8/2008 | Gelfand et al. |
| 2008/0208288 A1 | 8/2008 | Podrazhansky et al. |
| 2008/0216593 A1 | 9/2008 | Jacobsen et al. |
| 2008/0243204 A1 | 10/2008 | Uthman et al. |
| 2008/0288016 A1 | 11/2008 | Amurthur et al. |
| 2008/0300449 A1 | 12/2008 | Gerber et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0105785 A1 | 4/2009 | Wei et al. |
| 2009/0112133 A1 | 4/2009 | Deisseroth et al. |

(56) References Cited

U.S. PATENT DOCUMENTS

| | | |
|---|---|---|
| 2009/0157138 A1 | 6/2009 | Errico et al. |
| 2009/0187121 A1 | 7/2009 | Evans |
| 2009/0216294 A1 | 8/2009 | Ewing et al. |
| 2009/0222053 A1 | 9/2009 | Gaunt et al. |
| 2009/0247910 A1 | 10/2009 | Klapper |
| 2009/0249617 A1 | 10/2009 | Karicherla et al. |
| 2009/0299435 A1 | 12/2009 | Gliner et al. |
| 2009/0312690 A1 | 12/2009 | Kim et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0004715 A1 | 1/2010 | Fahey |
| 2010/0010381 A1 | 1/2010 | Skelton et al. |
| 2010/0010383 A1 | 1/2010 | Skelton et al. |
| 2010/0010572 A1 | 1/2010 | Skelton et al. |
| 2010/0057154 A1 | 3/2010 | Dietrich et al. |
| 2010/0059722 A1 | 3/2010 | Copp-Howland et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0168604 A1 | 7/2010 | Echauz |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0228180 A1 | 9/2010 | Jayes et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0004268 A1 | 1/2011 | Tcheng et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0054358 A1 | 3/2011 | Kim et al. |
| 2011/0071590 A1 | 3/2011 | Mounaim et al. |
| 2011/0098780 A1 | 4/2011 | Graupe et al. |
| 2011/0112605 A1 | 5/2011 | Fahey |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0196446 A1 | 8/2011 | Wu |
| 2011/0202107 A1 | 8/2011 | Sunagawa et al. |
| 2011/0208444 A1 | 8/2011 | Solinky |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0288615 A1 | 11/2011 | Armstrong et al. |
| 2011/0301663 A1 | 12/2011 | Wang et al. |
| 2012/0010492 A1 | 1/2012 | Thramann et al. |
| 2012/0050298 A1 | 3/2012 | Hoffman |
| 2012/0053491 A1 | 3/2012 | Nathan et al. |
| 2012/0059298 A1 | 3/2012 | Hoffman et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0098493 A1 | 4/2012 | Budike |
| 2012/0101326 A1 | 4/2012 | Simon et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0211013 A1 | 8/2012 | Otis |
| 2012/0220812 A1 | 8/2012 | Mishelevich |
| 2012/0239112 A1 | 9/2012 | Muraoka |
| 2012/0245483 A1 | 9/2012 | Lundqvist |
| 2012/0259255 A1 | 10/2012 | Tomlinson et al. |
| 2012/0277621 A1 | 11/2012 | Gerber et al. |
| 2012/0289869 A1 | 11/2012 | Tyler |
| 2012/0290036 A1 | 11/2012 | Karamanoglu et al. |
| 2012/0302821 A1 | 11/2012 | Burnett |
| 2012/0310298 A1 | 12/2012 | Besio et al. |
| 2012/0310299 A1 | 12/2012 | Norbert et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0035745 A1 | 2/2013 | Ahmed et al. |
| 2013/0053817 A1 | 2/2013 | Yun et al. |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0131770 A1 | 5/2013 | Rezai |
| 2013/0158624 A1 | 6/2013 | Bain et al. |
| 2013/0158627 A1 | 6/2013 | Gozani et al. |
| 2013/0178765 A1 | 7/2013 | Mishelevich |
| 2013/0211471 A1 | 8/2013 | Libbus et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148872 A1 | 5/2014 | Goldwasser et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0200573 A1 | 7/2014 | Deem et al. |
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |

(56) References Cited

U.S. PATENT DOCUMENTS

| | | |
|---|---|---|
| 2015/0005852 A1 | 1/2015 | Hershey et al. |
| 2015/0012067 A1 | 1/2015 | Bradley et al. |
| 2015/0038886 A1 | 2/2015 | Snow |
| 2015/0042315 A1 | 2/2015 | Cen et al. |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0196767 A1 | 7/2015 | Zaghloul |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0297901 A1 | 10/2015 | Kockx |
| 2015/0321000 A1 | 11/2015 | Rosenbluth et al. |
| 2015/0335882 A1 | 11/2015 | Gross |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0120432 A1 | 5/2016 | Sridhar et al. |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0213924 A1 | 7/2016 | Coleman et al. |
| 2016/0220836 A1 | 8/2016 | Parks |
| 2016/0262685 A1 | 9/2016 | Wagner et al. |
| 2016/0263376 A1 | 9/2016 | Yoo et al. |
| 2016/0279435 A1 | 9/2016 | Hyde et al. |
| 2016/0287879 A1 | 10/2016 | Denison et al. |
| 2016/0039239 A1 | 11/2016 | Yoo et al. |
| 2016/0339239 A1 | 11/2016 | Yoo et al. |
| 2016/0375249 A1 | 12/2016 | Bonnet et al. |
| 2017/0014625 A1 | 1/2017 | Rosenbluth et al. |
| 2017/0027812 A1 | 2/2017 | Hyde et al. |
| 2017/0042467 A1 | 2/2017 | Herr et al. |
| 2017/0056238 A1 | 3/2017 | Yi et al. |
| 2017/0056643 A1 | 3/2017 | Herb et al. |
| 2017/0079597 A1 | 3/2017 | Horne |
| 2017/0080207 A1 | 3/2017 | Perez et al. |
| 2017/0095667 A1 | 4/2017 | Yakovlev et al. |
| 2017/0113045 A1 | 4/2017 | Baldassano et al. |
| 2017/0157398 A1 | 6/2017 | Wong et al. |
| 2017/0165485 A1 | 6/2017 | Sullivan et al. |
| 2017/0132067 A1 | 8/2017 | Wong et al. |
| 2017/0224991 A1 | 8/2017 | Wingeier et al. |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2017/0312512 A1 | 11/2017 | Creasey et al. |
| 2017/0361093 A1 | 12/2017 | Yoo et al. |
| 2017/0368329 A1 | 12/2017 | Tyler et al. |
| 2018/0001086 A1 | 1/2018 | Bartholomew et al. |
| 2018/0001088 A1 | 1/2018 | Tass |
| 2018/0021576 A1 | 1/2018 | Wong et al. |
| 2018/0036535 A1 | 2/2018 | Wong et al. |
| 2018/0042654 A1 | 2/2018 | Ingvarsson et al. |
| 2018/0049676 A1 | 2/2018 | Griffiths et al. |
| 2018/0064344 A1 | 3/2018 | Nguyen |
| 2018/0064362 A1 | 3/2018 | Hennings et al. |
| 2018/0064944 A1 | 3/2018 | Grill et al. |
| 2018/0116546 A1 | 5/2018 | Pastoor et al. |
| 2018/0132757 A1 | 5/2018 | Kong et al. |
| 2018/0140842 A1 | 5/2018 | Olaighin et al. |
| 2018/0168905 A1 | 6/2018 | Goodall et al. |
| 2018/0169400 A1 | 6/2018 | Wong et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0236217 A1 | 8/2018 | Hamner et al. |
| 2018/0264263 A1 | 9/2018 | Rosenbluth et al. |
| 2018/0345020 A1 | 12/2018 | Ironi et al. |
| 2019/0001117 A1 | 1/2019 | Ben-David et al. |
| 2019/0001129 A1 | 1/2019 | Rosenbluth et al. |
| 2019/0001139 A1 | 1/2019 | Mishra et al. |
| 2019/0126047 A1 | 5/2019 | Kassiri Bidhendi et al. |
| 2019/0134393 A1 | 5/2019 | Wong et al. |
| 2019/0143098 A1 | 5/2019 | Kaplan et al. |
| 2019/0143111 A1 | 5/2019 | Hamner et al. |
| 2019/0143113 A1 | 5/2019 | Wong et al. |
| 2019/0167976 A1 | 6/2019 | Byers et al. |
| 2019/0269914 A1 | 9/2019 | Moaddeb et al. |
| 2019/0298998 A1 | 10/2019 | Coleman et al. |
| 2019/0321636 A1 | 10/2019 | Law et al. |
| 2019/0343462 A1 | 11/2019 | Grant et al. |
| 2019/0374771 A1 | 12/2019 | Simon et al. |
| 2020/0023183 A1 | 1/2020 | Ollerenshaw et al. |
| 2020/0038654 A1 | 2/2020 | Doskocil et al. |
| 2020/0046968 A1 | 2/2020 | Herr et al. |
| 2020/0061378 A1 | 2/2020 | Ganguly et al. |
| 2020/0093400 A1 | 3/2020 | Hamner et al. |
| 2020/0139118 A1 | 5/2020 | John et al. |
| 2020/0147373 A1 | 5/2020 | Tamaki et al. |
| 2020/0155847 A1 | 5/2020 | Perez |
| 2020/0171269 A1 | 6/2020 | Hooper et al. |
| 2020/0171304 A1 | 6/2020 | Simon et al. |
| 2020/0179687 A1 | 6/2020 | Wong et al. |
| 2020/0197707 A1 | 6/2020 | Covalin |
| 2020/0215324 A1 | 7/2020 | Mantovani et al. |
| 2020/0221975 A1 | 7/2020 | Basta et al. |
| 2020/0254247 A1 | 8/2020 | Brezel et al. |
| 2020/0254251 A1 | 8/2020 | Wong et al. |
| 2020/0269046 A1 | 8/2020 | Page et al. |
| 2020/0276442 A1 | 9/2020 | Owen |
| 2020/0282201 A1 | 9/2020 | Doskocil |
| 2020/0289813 A1 | 9/2020 | Ito et al. |
| 2020/0289814 A1 | 9/2020 | Hamner et al. |
| 2020/0297999 A1 | 9/2020 | Pal |
| 2020/0316379 A1 | 10/2020 | Yoo et al. |
| 2020/0324104 A1 | 10/2020 | Labuschagne et al. |
| 2020/0338348 A1 | 10/2020 | Honeycutt et al. |
| 2020/0367775 A1 | 11/2020 | Buckley et al. |
| 2020/0405188 A1 | 12/2020 | Sharma et al. |
| 2020/0406022 A1 | 12/2020 | Sharma et al. |
| 2021/0016079 A1 | 1/2021 | Ekelem et al. |
| 2021/0031026 A1 | 2/2021 | Simon et al. |
| 2021/0031036 A1 | 2/2021 | Sharma et al. |
| 2021/0052883 A1 | 2/2021 | Wong et al. |
| 2021/0052897 A1 | 2/2021 | Bhadra et al. |
| 2021/0052900 A1 | 2/2021 | Pepin et al. |
| 2021/0060337 A1 | 3/2021 | Wybo et al. |
| 2021/0069507 A1 | 3/2021 | Gozani et al. |
| 2021/0100999 A1 | 4/2021 | Rosenbluth et al. |
| 2021/0101007 A1 | 4/2021 | Hamner et al. |
| 2021/0113834 A1 | 4/2021 | Wong et al. |
| 2021/0162212 A1 | 6/2021 | Kern et al. |
| 2021/0169684 A1 | 6/2021 | Black et al. |
| 2021/0187279 A1 | 6/2021 | Bouton et al. |
| 2021/0205619 A1 | 7/2021 | Wong et al. |
| 2021/0213283 A1 | 7/2021 | Yoo et al. |
| 2021/0220650 A1 | 7/2021 | Kassiri Bidhendi et al. |
| 2021/0244940 A1 | 8/2021 | Liberatore et al. |
| 2021/0244950 A1 | 8/2021 | Ironi et al. |

(56) References Cited

U.S. PATENT DOCUMENTS

| | | |
|---|---|---|
| 2021/0252278 A1 | 8/2021 | Hamner et al. |
| 2021/0260379 A1 | 8/2021 | Charlesworth et al. |
| 2021/0266011 A1 | 8/2021 | Chen et al. |
| 2021/0283400 A1 | 9/2021 | Hamner et al. |
| 2021/0289814 A1 | 9/2021 | Roubos-Van den Hil et al. |
| 2021/0299445 A1 | 9/2021 | Rajguru et al. |
| 2021/0308460 A1 | 10/2021 | Wong et al. |
| 2021/0330547 A1 | 10/2021 | Moaddeb et al. |
| 2021/0330974 A1 | 10/2021 | Wong et al. |
| 2021/0353181 A1 | 11/2021 | Roh |
| 2021/0379374 A1 | 12/2021 | Hamner et al. |
| 2021/0379379 A1 | 12/2021 | Campean et al. |
| 2021/0402172 A1 | 12/2021 | Ross et al. |
| 2022/0001164 A1 | 1/2022 | Sharma et al. |
| 2022/0016413 A1 | 1/2022 | John et al. |
| 2022/0031245 A1 | 2/2022 | Bresler |
| 2022/0054820 A1 | 2/2022 | Turner |
| 2022/0054831 A1 | 2/2022 | McBride |
| 2022/0088373 A1 | 3/2022 | Burnett |
| 2022/0126095 A1 | 4/2022 | Rajguru et al. |
| 2022/0212007 A1 | 7/2022 | Rajguru et al. |
| 2022/0218991 A1 | 7/2022 | Moaddeb et al. |
| 2022/0233860 A1 | 7/2022 | Hamner et al. |
| 2022/0266011 A1 | 8/2022 | Hamner et al. |
| 2022/0266012 A1 | 8/2022 | Hamner et al. |
| 2023/0009158 A1 | 1/2023 | Liberatore |
| 2023/0201584 A1 | 6/2023 | Rajguru et al. |

FOREIGN PATENT DOCUMENTS

| | | |
|---|---|---|
| CN | 101115524 | 1/2008 |
| CN | 101365373 | 2/2009 |
| CN | 101687093 | 3/2010 |
| CN | 102089031 | 6/2011 |
| CN | 103517732 | 1/2014 |
| CN | 103889503 | 6/2014 |
| CN | 104144729 | 11/2014 |
| DE | 10 2008042373 | 4/2010 |
| DE | 10 2009004011 | 7/2010 |
| EP | 0000759 | 2/1979 |
| EP | 0725665 | 1/1998 |
| EP | 1062988 | 12/2000 |
| EP | 1558333 | 5/2007 |
| EP | 1727591 | 4/2009 |
| EP | 2383014 | 11/2011 |
| EP | 2291115 | 9/2013 |
| EP | 2801389 | 11/2014 |
| EP | 3020448 | 5/2016 |
| EP | 2029222 | 3/2017 |
| EP | 2780073 | 9/2017 |
| EP | 1951365 | 10/2017 |
| EP | 3154627 | 4/2018 |
| EP | 2827771 | 5/2018 |
| EP | 3184143 | 7/2018 |
| EP | 3075412 | 12/2018 |
| EP | 3349712 | 7/2019 |
| EP | 3503960 | 3/2020 |
| EP | 3352846 | 7/2020 |
| EP | 3493874 | 8/2020 |
| EP | 3409200 | 9/2020 |
| EP | 3427793 | 11/2020 |
| EP | 3758595 | 1/2021 |
| EP | 3641876 | 4/2021 |
| EP | 3679979 | 6/2021 |
| EP | 3402404 | 7/2021 |
| EP | 3562541 | 7/2021 |
| EP | 3675795 | 8/2021 |
| EP | 3100765 | 1/2022 |
| EP | 4108292 | 12/2022 |
| ES | 2222819 | 3/2006 |
| ES | 2272137 | 6/2008 |
| GB | 2496449 | 5/2013 |
| JP | 2010-527256 | 1/1900 |
| JP | 63-500644 | 3/1988 |
| JP | 2002-200178 | 7/2002 |
| JP | 2003-501207 | 1/2003 |
| JP | 2003-533299 | 11/2003 |
| JP | 2004-512104 | 4/2004 |
| JP | 2006-503658 | 2/2006 |
| JP | 2008-018235 | 1/2008 |
| JP | 2009-034328 | 2/2009 |
| JP | 2009-512516 | 3/2009 |
| JP | 2009-529352 | 8/2009 |
| JP | 2010-506618 | 3/2010 |
| JP | 2010-512926 | 4/2010 |
| JP | 2010-246745 | 11/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 5439921 | 3/2014 |
| JP | 2015-514460 | 5/2015 |
| JP | 2016-511651 | 4/2016 |
| JP | 2018-038597 | 3/2018 |
| KR | 20130104446 | 9/2013 |
| WO | WO 1987/01024 | 2/1987 |
| WO | WO 1994/000187 | 1/1994 |
| WO | WO 1994/017855 | 8/1994 |
| WO | WO 1996/032909 | 10/1996 |
| WO | WO 1998/043700 | 10/1998 |
| WO | WO 1999/019019 | 4/1999 |
| WO | WO 2000/015293 | 3/2000 |
| WO | WO 2000/076436 | 12/2000 |
| WO | WO 2001/087411 | 11/2001 |
| WO | WO 2002/017987 | 3/2002 |
| WO | WO 2002/034327 | 5/2002 |
| WO | WO 2004/037344 | 5/2004 |
| WO | WO 2004/108209 | 12/2004 |
| WO | WO 2005/007029 | 5/2005 |
| WO | WO 2005/122894 | 12/2005 |
| WO | WO 2006/102724 | 10/2006 |
| WO | WO 2007/092290 | 8/2007 |
| WO | WO 2007/112092 | 10/2007 |
| WO | WO 2008/045598 | 4/2008 |
| WO | WO 2008/062395 | 5/2008 |
| WO | WO 2009/153730 | 12/2009 |
| WO | WO 2010/111321 | 9/2010 |
| WO | WO 2010/141155 | 12/2010 |
| WO | WO 2011/119224 | 9/2011 |
| WO | WO 2011/144883 | 11/2011 |
| WO | WO 2011/149656 | 12/2011 |
| WO | WO 2012/040243 | 3/2012 |
| WO | WO 2013/071307 | 5/2013 |
| WO | WO 2013/074809 | 5/2013 |
| WO | WO 2013/173727 | 11/2013 |
| WO | WO 2014/043757 | 3/2014 |
| WO | WO 2014/053041 | 4/2014 |
| WO | WO 2014/089549 | 6/2014 |
| WO | WO 2014/093964 | 6/2014 |
| WO | WO 2014/113813 | 7/2014 |
| WO | WO 2014/146082 | 9/2014 |
| WO | WO 2014/151431 | 9/2014 |
| WO | WO 2014/153201 | 9/2014 |
| WO | WO 2014/207512 | 12/2014 |
| WO | WO 2015/033152 | 3/2015 |
| WO | WO 2015/039206 | 3/2015 |
| WO | WO 2015/039244 | 3/2015 |
| WO | WO 2015/042365 | 3/2015 |
| WO | WO 2015/079319 | 6/2015 |
| WO | WO 2015/085880 | 6/2015 |
| WO | WO 2015/095880 | 6/2015 |
| WO | WO 2015/128090 | 9/2015 |
| WO | WO 2015/164706 | 10/2015 |
| WO | WO 2015/187712 | 12/2015 |
| WO | WO 2016/007093 | 1/2016 |
| WO | WO 2016/019250 | 2/2016 |
| WO | WO 2016/094728 | 6/2016 |
| WO | WO 2016/102958 | 6/2016 |
| WO | WO 2016/110804 | 7/2016 |
| WO | WO 2016/128985 | 8/2016 |
| WO | WO 2016/149751 | 9/2016 |
| WO | WO 2016/166281 | 10/2016 |
| WO | WO 2016/179407 | 11/2016 |

(56) References Cited

FOREIGN PATENT DOCUMENTS

| | | |
|---|---|---|
| WO | WO 2016/189422 | 12/2016 |
| WO | WO 2016/195587 | 12/2016 |
| WO | WO 2016/201366 | 12/2016 |
| WO | WO 2017/004021 | 1/2017 |
| WO | WO 2017/010930 | 1/2017 |
| WO | WO 2017/023864 | 2/2017 |
| WO | WO 2017/044904 | 3/2017 |
| WO | WO 2017/053847 | 3/2017 |
| WO | WO 2017/062994 | 4/2017 |
| WO | WO 2017/086798 | 5/2017 |
| WO | WO 2017/088573 | 6/2017 |
| WO | WO 2017/132067 | 8/2017 |
| WO | WO 2017/199026 | 11/2017 |
| WO | WO 2017/208167 | 12/2017 |
| WO | WO 2017/209673 | 12/2017 |
| WO | WO 2017/210729 | 12/2017 |
| WO | WO 2017/221037 | 12/2017 |
| WO | WO 2018/009680 | 1/2018 |
| WO | WO 2018/028170 | 2/2018 |
| WO | WO 2018/028220 | 2/2018 |
| WO | WO 2018/028221 | 2/2018 |
| WO | WO 2018/039458 | 3/2018 |
| WO | WO 2018/093765 | 5/2018 |
| WO | WO 2018/106839 | 6/2018 |
| WO | WO 2018/112164 | 6/2018 |
| WO | WO 2018/187241 | 10/2018 |
| WO | WO 2019/005774 | 1/2019 |
| WO | WO 2019/014250 | 1/2019 |
| WO | WO 2019/028000 | 2/2019 |
| WO | WO 2019/046180 | 3/2019 |
| WO | WO 2019/082180 | 6/2019 |
| WO | WO 2019/143790 | 7/2019 |
| WO | WO 2019/169240 | 9/2019 |
| WO | WO 2019/202489 | 10/2019 |
| WO | WO 2019/213433 | 11/2019 |
| WO | WO 2020/006048 | 1/2020 |
| WO | WO 2020/068830 | 4/2020 |
| WO | WO 2020/069219 | 4/2020 |
| WO | WO 2020/086726 | 4/2020 |
| WO | WO 2020/131857 | 6/2020 |
| WO | WO 2020/185601 | 9/2020 |
| WO | WO 2021/005584 | 1/2021 |
| WO | WO 2021/055716 | 3/2021 |
| WO | WO 2021/062345 | 4/2021 |
| WO | WO 2021/127422 | 6/2021 |
| WO | WO 2021/228128 | 11/2021 |
| WO | WO 2021/236815 | 11/2021 |
| WO | WO 2021/252292 | 12/2021 |
| WO | WO 2022/221858 | 10/2022 |
| WO | WO 2023/283568 | 1/2023 |

OTHER PUBLICATIONS

U.S. Appl. No. 15/354,943, filed Nov. 17, 2016, Wong et al.
U.S. Appl. No. 15/580,631, filed Dec. 7, 2017, Wong et al.
U.S. Appl. No. 15/721,475, filed Sep. 29, 2017, Wong et al.
U.S. Appl. No. 15/721,480, filed Sep. 29, 2017, Wong et al.
U.S. Appl. No. 15/748,616, filed Jan. 29, 2018, Hamner et al.
U.S. Appl. No. 15/762,043, filed Mar. 21, 2018, Hamner et al.
U.S. Appl. No. 16/071,056, filed Jul. 18, 2018, Wong et al.
U.S. Appl. No. 16/241,846, filed Jan. 7, 2019, Wong et al.
U.S. Appl. No. 16/242,983, filed Jan. 8, 2019, Wong et al.
U.S. Appl. No. 16/247,310, filed Feb. 22, 2019, Wong et al.
U.S. Appl. No. 16/327,780, filed Feb. 22, 2019, Hamner et al.
U.S. Appl. No. 16/780,758, filed Feb. 3, 2020, Hamner et al.
U.S. Appl. No. 16/792,100, filed Feb. 14, 2020, Hamner et al.
U.S. Appl. No. 16/833,388, filed Mar. 27, 2020, Hamner et al.
U.S. Appl. No. 16/962,810, filed Jul. 16, 2002, Hamner et al.
U.S. Appl. No. 16/993,085, filed Aug. 13, 2020, Balbaky et al.
U.S. Appl. No. 17/013,396 filed Sep. 4, 2020, Wong et al.
U.S. Appl. No. 17/052,483, filed Nov. 2, 2020, Liberatore et al.
U.S. Appl. No. 17/061,231, filed Oct. 1, 2020, Yu.
U.S. Appl. No. 17/080,544, filed Oct. 26, 2020, Wong et al.
U.S. Appl. No. 17/633,004, filed May 11, 2020, Wong et al.
U.S. Appl. No. 17/633,010, filed May 11, 2022, Wong et al.
Amarenco et al. "Urondynamic Effect of Acute Transducteaneous Posterior Tibial Nerve Stimulation in Overactive Bladder" Journal of Urology vol. 169, 2210-2215 (Jun. 2003).
Apartis; Clinical neurophysiology in movement disorders. Handb Clin Neurol; 111; Pediatric Neurology Pt. 1; pp. 87-92;Apr. 2013.
Barath et al., 2020, Brain metabolic changes with longitudinal transcutaneous afferent patterned stimulation in essential tremor subjects, Tremor and Other Hyperkinetic Movements, 10(1):52, pp. 1-10.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation.; Plos One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brillman et al., 2022, Real-world evidence of transcutaneous afferent patterned stimulation for essential tremor, Tremor and Other Hyperkinetic Movements, 12(1):27, pp. 1-11.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006.
Buschbacher et al.; Manual of nerve conduction series; 2nd edition; Demos Medical Publishing, LLC; 2006 (part 2, p. 143 to 299).
Cagnan et al.; Phase dependent modulation of tremor amplitude in essential tremor through thalamic stimulation; Brain; 136(10); pp. 3062-3075; Oct. 2013.

(56) References Cited

OTHER PUBLICATIONS

Campero et al.; Peripheral projections of sensory fascicles in the human superficial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congress on Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; 1998.
Di Giovangiulio et al.; The Neuromodulation of the intestinal immune system and its relevance in inflammatory bowel disease; Frontier's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Biosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Ferreira et al., 2019, MDS evidence-based review of treatments for essential tremor, Movement Disorders, 34(7):950-958.
Fiorentino et al., 2011, Self calibrating wearable active running asymmetry measurement and correction, Journal of Control Engineering and Applied Informatics, 13(2):3-8.
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; Real-time estimation of pathological tremor parameters from gyroscope data.; Sensors; 10(3); pp. 2129-2149; Mar. 2010.
Gallego et al.; A soft wearable robot for tremor assessment and suppression; 2011 IEEE International Conference on Robotics and Automation; Shanghai International Conference Center; pp. 2249-2254; May 9-13, 2011.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagal afferent nerve stimulation in migraine patients; Pain; International Association for the Study of Pain; 2017.
Garcia-Rill, E., et al. "Arousal, motor control, and Parkinson's disease." Translational neuroscience 6.1 pp. 198-207 (2015).

Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulation of innervated muscle; Archives of Physical Medicine and Rehabilitation; 56(6); pp. 243-249; Jun. 1975.
Gupta et al., 2021, Exploring essential tremor: results from a large online survey, Clinical Parkinsonism & Related Disorders, 5:100101, 4 pp.
Haeri et al.; Modeling the Parkinson's tremor and its treatments; Journal of Theoretical Biology; 236(3); pp. 311-322; Oct. 2005.
Halonen et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Haubenberger et al., 2018, Essential Tremor, The New England Journal of Medicine, 378:1802-1810 and Supplementary Appendix.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Hellwig et al., Feb. 17, 2001, Tremor-correlated cortical activity in essential tremor, The Lancet, 357:519-523.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170·175.
Hernandez-Martin et al., 2021, High-fidelity transmission of high-frequency burst stimuli from peripheral nerve to thalamic nuclei in children with dystonia, Scientific Reports, 11:8498, 9 pp.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heartrate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurology and urodynamics 30.8 (2011): 1467-1472.
Inoue et al. "Stretchable human interface using a conductive silicone elastomer containing silver fillers." Consumer Electronics, 2009. ISCE'09. IEEE 13th International Symposium on. IEEE, 2009.
International Search Report and Written Opinion dated Apr. 12, 2019, in application No. PCT/US2019/013966.
Isaacson et al., 2020, Prospective home-use study on non-invasive neuromodulation therapy for essential tremor, Tremor and Other Hyperkinetic Movements, 10(1):29, pp. 1-16.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.

(56) References Cited

OTHER PUBLICATIONS

Krauss et al.; Chronic spinal cord stimulation in medically intractable orthostatic tremor; J Neurol Neurosurg Psychiatry; 77(9); pp. 1013-1016; Sep. 2006.

Krishnamoorthy et al., 2008, Gait Training After Stroke: A Pilot Study Combining a Gravity-Balanced Orthosis, Functional Electrical Stimulation, and Visual Feedback, Journal of Neurologic Physical Therapy, 32(4):192-202.

Kuhn et al.; Array electrode design for transcutaneous electrical stimulation a simulation study; Medical Engineering & Physics; 31 (8); pp. 945-951; Oct. 2009.

Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.

Kunz, Patrik, et al. "5 kHz transcranial alternating current stimulation: lack of cortical excitability changes when grouped in a theta burst pattern." Frontiers in Human Neuroscience 10 (2016): 683.

Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.

Laroy et al.; The sensory innervation pattern of the fingers; J. Neurol.; 245 (5); pp. 294-298; May 1998.

Lee et al.; Resetting of tremor by mechanical perturbations: A comparison of essential tremor and parkinsonian tremor; Annals of Neurology; 10(6); pp. 523-531; Dec. 1981.

Legon et al.; Pulsed ultrasound differentially stimulates somatosensory circuits in humans as indicated by EEG and fMRI; Plos One; 7(12); e51177; 14 pgs.; Dec. 2012.

Liao, Wen-Chien, et al. "A noninvasive evaluation of autonomic nervous system dysfunction in women with an overactive bladder." International Journal of Gynecology & Obstetrics 110.1 (2010): 12-17.

Lin et al., 2018, Noninvasive neuromodulation inessential tremor demonstrates relief in a sham-controlled pilot trial, Movement Disorders, 33(7):1182-1183.

Llinas et al., Dec. 21, 1999, Thalamocortical dysrhythmia: a neurological and neuropsychiatric syndrome characterized by magnetoencephalography, PNAS, 96(26):15222-15227.

Lourenco et al.; Effects produced in human arm and forearm motoneurons after electrical stimulation of ulnar and median nerves at wrist level; Experimental Brain Research; 178(2); pp. 267-284; Apr. 2007.

Lyons et al., 2021, Essential tremor in adult patients, International Essential Tremor Foundation, 16 pp.

Malek et al.; The utility of electromyography and mechanomyography for assessing neuromuscular function: a noninvasive approach; Phys Med Rehabil in N Am; 23(1); pp. 23-32; Feb. 2012.

Mamorita et al.; Development of a system for measurement and analysis of tremor using a three-axis accelerometer; Methods Inf Med; 48(6); pp. 589-594; epub Nov. 2009.

Maneski et al.; Electrical Stimulation for suppression of pathological tremor; Med Biol Eng Comput; 49(10); pp. 1187-1193; Oct. 2011.

Marsden et al.; Coherence between cerebellar thalamus, cortex and muscle in man; Brain; 123; pp. 1459-1470; Jul. 2000.

Marshall, Ryan, et al. "Bioelectrical stimulation for the reduction of inflammation in inflammatory bowel disease." Clinical Medicine Insights: Gastroenterology 8 (2015): CGast-S31779.

McAuley et al.; Physiological and pathological tremors and rhythmic central motor control; Brain; 123(Pt 8); pp. 1545-1567; Aug. 2000.

McIntyre et al.; Finite element analysis of current-density and electric field generated by metal microelectrodes; Annals of Biomedical Engineering; 29(3); pp. 227-235; Mar. 2001.

Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.

Mehnert, Ulrich, et al. "Heart rate variability: an objective measure of autonomic activity and bladder sensations during urodynamics." Neurology and urodynamics 28.4 (2009): 313-319.

Miguel et al.; Alcohol consumption and the incidence of Parkinson's disease; Ann. Neurol.; 54(2); pp. 170-175; May 15, 2003.

Miller et al.; Multiplexed microneedle-based biosensor array for characterization of metabolic acidosis; Talanta; 88; pp. 739-742; Jan. 2012 (author manuscript; 13 pgs.).

Miller et al.; Neurostimulation in the treatment of primary headaches; Pract Neurol; Apr. 11, 2016;16:pp. 362-375.

Milne et al.; Habituation to repeated in painful and non-painful cutaneous stimuli: A quantitative psychophysical study; Experimental Brain Research; 87(2); pp. 438-444; Nov. 1991.

Mommaerts et al.; Excitation and nerve conduction; in Comprehensive Human Physiology; Springer Berlin Heidelberg; Chap. 13; pp. 283-294; Mar. 1996.

Mones et al.; The response of the tremor of patients with Parkinsonism to peripheral nerve stimulation; J Neurology, Neurosurgery, and Psychiatry; 32(6); pp. 512-518; Dec. 1969.

Morgante et al.: How many parkinsonian patients are suitable candidates for deep brain stimulation of subthalamic nucleus?; Results of a Questionnaire, Parkinsonism Relat Disord; 13; pp. 528-531; Dec. 2007.

Munhoz et al.; Acute effect of transcutaneous electrical nerve stimulation on tremor; Movement Disorders; 18(2); pp. 191-194; Feb. 2003.

Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.

Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.

Pahwa et al., 2018, An acute randomized controlled trial of noninvasive peripheral nerve stimulation in essential tremor, Neuromodulation, 22:537-545.

Peng et al., 2015, Flexible dry electrode based on carbon nanotube/polymer hybrid micropillars for biopotential recording, Sensor and Actuatora A: Physical, 235:48-65.

Perez et al.; Patterned Sensory Stimulation Induces Plasticity in Reciprocal la Inhibition in Humans; The Journal of Neuroscience; 23(6); pp. 2014-2018; Mar. 2003.

Perez-Reyes, Jan. 2003, Molecular physiology of low-voltage-activated T-type calcium channels, Physiol. Rev. 83:117-161.

Perlmutter et al.; Deep brain stimulation; Ann Rev Neurosci; 29; pp. 229-257; Jul. 2006.

Popovi Maneski et al.; Electrical stimulation for the suppression of pathological tremor; Medical & Biological Engineering & Computing; 49(10); pp. 1187-1193; Oct. 2011.

Popovic-Bijelic et al. "Multi-field surface electrode for selective electrical stimulation." Artificial organs 29.6 (2005): 448-452.

Prochazka et al.; Attenuation of pathological tremors by functional electrical stimulation I: Method; Annals of Biomedical Engineering; 20(2); pp. 205-224; Mar. 1992.

Pulliam et al.; Continuous in-home monitoring of essential tremor; Parkinsonism Relat Disord; 20(1); pp. 37-40; Jan. 2014.

Quattrini et al.; Understanding the impact of painful diabetic neuropathy; Diabetes/Metabolism Research and Reviews; 19, Suppl. 1; pp. S2-8; Jan-Feb. 2003.

Rocon et al.; Design and validation of a rehabilitation robotic exoskeleton for tremor assessment and suppression; IEEE Trans Neural Sys and Rehab Eng.; 15(3); pp. 367-378; Sep. 2007.

Sigrist et al., 2012. Augmented visual, auditory, haptic, and multimodal feedback in motor learning: A review. Psychonomic Bulletin & Review, 20(1):21-53.

Silverstone et al.; Non-Invasive Neurostimulation In The Control of Familial Essential Tremor Using The Synaptic Neuromodulator; Conference Proceedings, International Functional Electrical Stimulation Society (IFES); Ed. Paul Meadows; 3 pgs.; May 1999.

(56) References Cited

OTHER PUBLICATIONS

Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Solomonow et al., 1998, Studies toward spasticity suppression with high frequency electrical stimulation, Orthopedics, 7(8):1284-1288.
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained after effects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Biol Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Tolosa et al.; Essential tremor: treatment with propranolol; Neurology; 25(11); pp. 1041; Nov. 1975.
Tracey; The inflammatory reflex; Nature; vol. 420; pp. 853-859; Dec. 19/26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecal Incontinence in inflammatorybowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wallerberger, Apr. 4, 2019, Efficient Estimation of Autocorrelation Spectra, ArXiv.org, https://arxiv.org/abs/1810.05079.
Wardman et al.; Subcortical, and cerebellar activation evoked by selective stimulation of muscle and cutaneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh et al., "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.

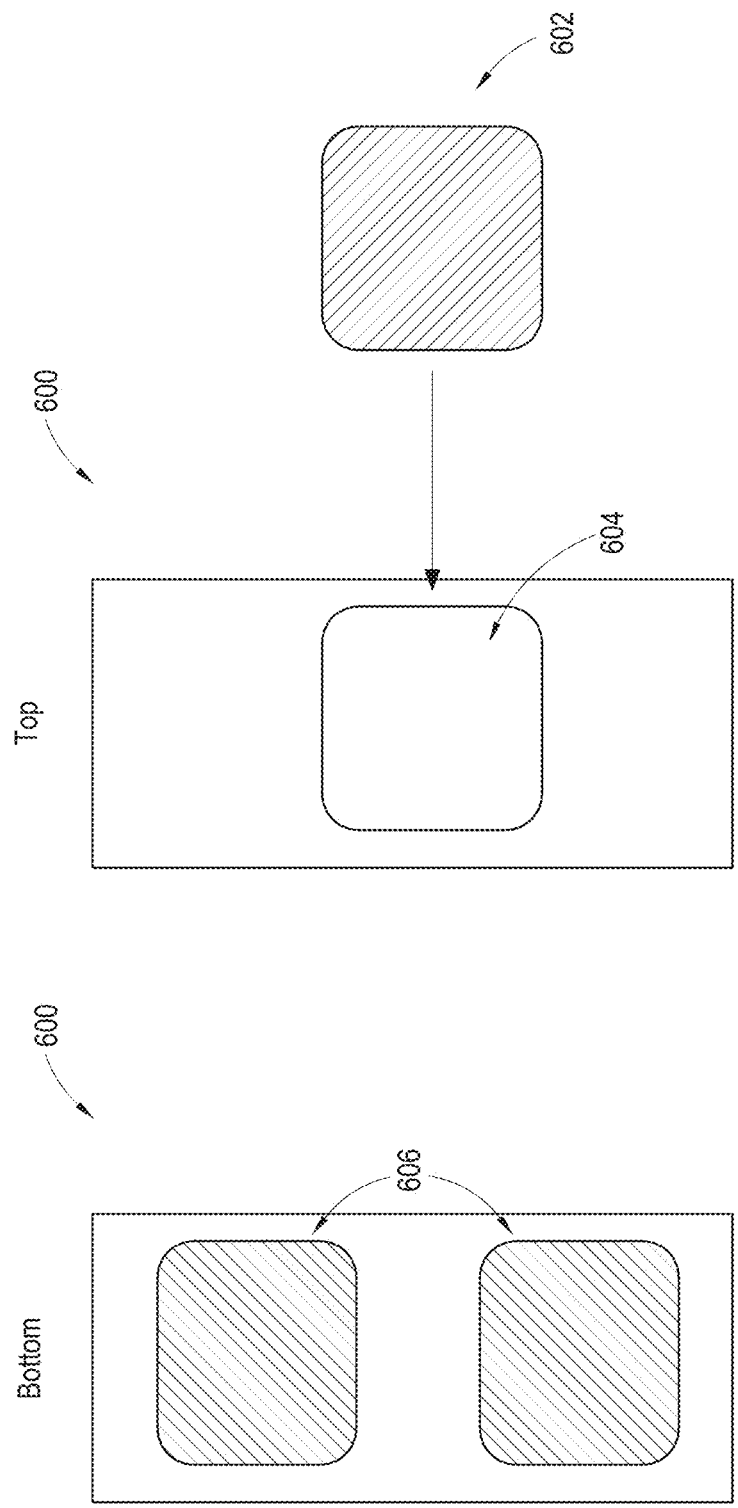

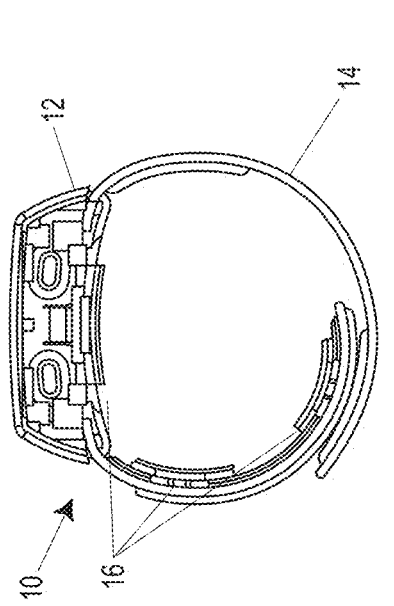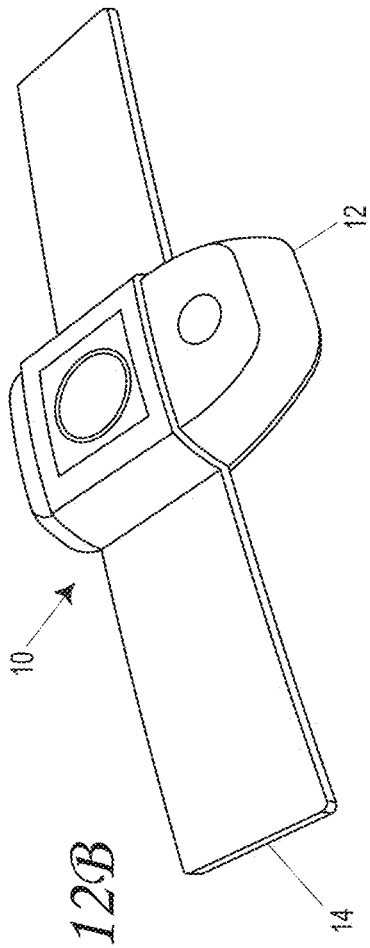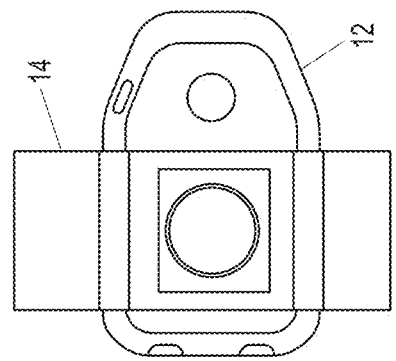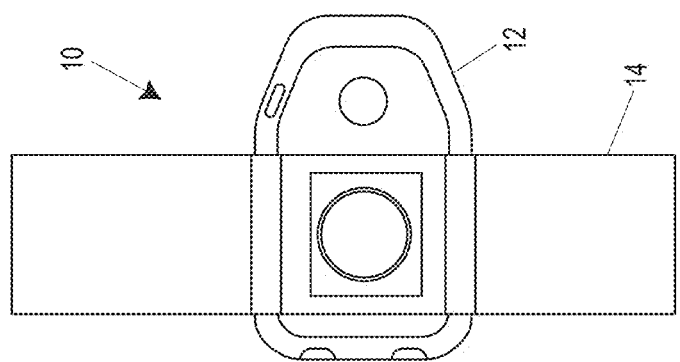

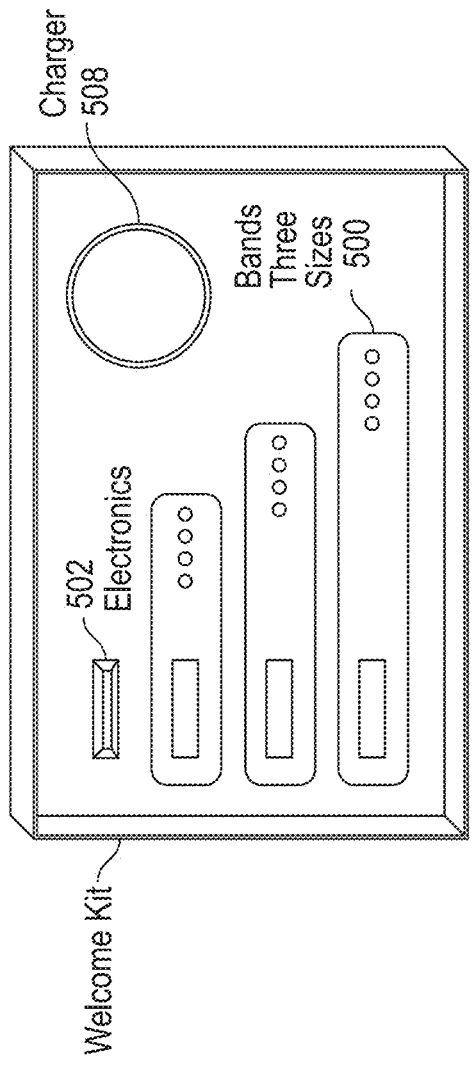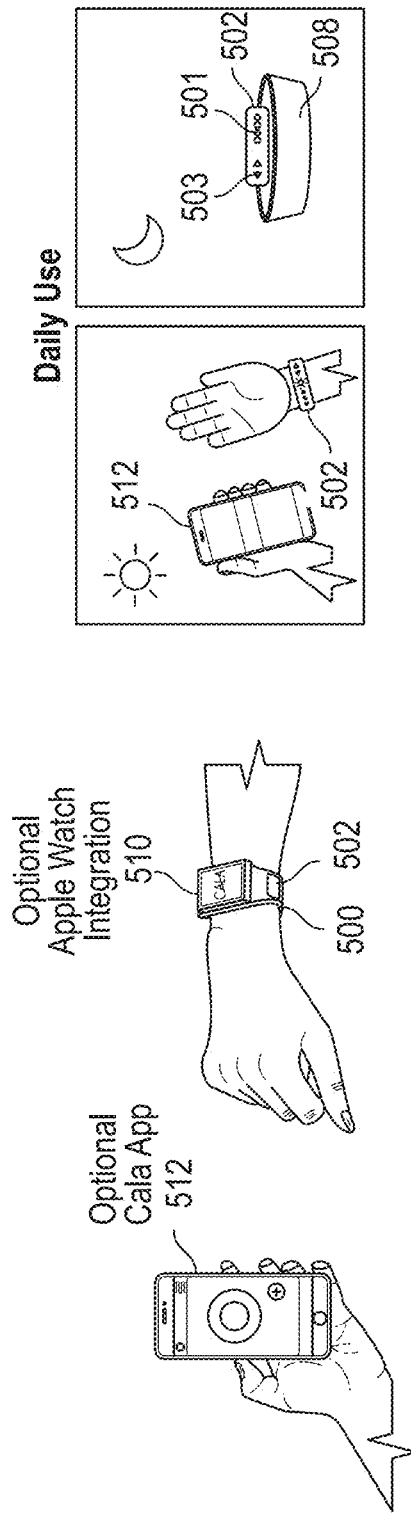

SYSTEMS AND METHODS FOR TREATING INFLAMMATORY BOWEL DISEASE THROUGH PERIPHERAL NERVE STIMULATION

INCORPORATION BY REFERENCE TO ANY PRIORITY APPLICATIONS

This application is the U.S. National Stage of PCT App. No. PCT/US2019/013966 filed on Jan. 17, 2019, which in turn claims the benefit under 35 U.S.C. § 119(e) as a nonprovisional application of U.S. Pat. App. No. 62/618,557 filed on Jan. 17, 2018, which is hereby incorporated by reference in its entirety. Any and all applications for which a foreign or domestic priority claim is identified in the Application Data Sheet as filed with the present application are hereby incorporated by reference under 37 CFR 1.57. Further form factors, stimulation features, targets, and indications, and methods that can be used with systems and methods as disclosed herein can be found, for example, in U.S. Pat. No. 9,452,287 to Rosenbluth et al., U.S. Pat. No. 9,802,041 to Wong et al., PCT Pub. No. WO 2016/201366 to Wong et al., PCT Pub. No. WO 2017/132067 to Wong et al., PCT Pub. No. WO 2017/053847 to Hamner et al., PCT App. No. PCT/US2017/040920 to Wong et al., and PCT App. No. PCT/US2017/048424 to Rosenbluth et al. filed on Aug. 24, 2017, each of which is hereby incorporated by reference in their entireties.

BACKGROUND

Field of the Invention

Some embodiments of the invention relate generally to the treatment of inflammatory diseases, including those of the gastrointestinal tract such as inflammatory bowel disease (e.g., Crohn's disease, microscopic colitis, or ulcerative colitis), celiac sprue, primary biliary cirrhosis, primary sclerosing cholangitis, autoimmune hepatitis, and the like; or systemic or other local inflammatory disease such as rheumatoid arthritis, systemic lupus erythematosis, systemic sclerosis, and Sjogren's syndrome through neuromodulation (such as noninvasive peripheral nerve stimulation).

Description of the Related Art

Inflammatory bowel disease (IBD) is a group of organic diseases, classically divided into Crohn's disease (CD) and ulcerative colitis (UC), involving the gastrointestinal (GI) tract, particularly the colon and small intestine for CD, starting early in life (between 15 and 30 years) and evolving by alternating periods of flares and remissions of variable duration. Symptoms are characterized by abdominal pain, diarrhea, fever, weight loss and extra-intestinal (skin, eyes, joints) manifestations. IBD is conventionally treated by various pharmacologic therapies, including non-steroidal anti-inflammatory agents, steroids, monoclonal antibodies, and other immunomodulators, all of which carry the risk of potential side effects. New therapies that may have increased efficacy and/or decreased side effects are needed.

SUMMARY

Some embodiments of the present invention relate generally to the treatment of inflammatory diseases, autoimmune diseases, and/or diseases involving the gastrointestinal tract, and in some cases specifically to systems and methods of treating inflammatory bowel diseases, including but not limited to ulcerative colitis, Crohn's disease, and microscopic colitis, through neuromodulation (such as noninvasive peripheral nerve stimulation). Microscopic colitis includes, for example, collagenous colitis and lymphocytic colitis.

In some embodiments, other gastrointestinal-related diseases including irritable bowel syndrome, autoimmune gastrointestinal dysmotility (AGID), esophagitis, gastritis, duodenitis, ischemic colitis, celiac sprue, Whipple's disease, peptic ulcer disease, pancreatitis, hepatitis including autoimmune hepatitis, non-alcoholic steatohepatitis (NASH), cholecystitis, primary biliary cirrhosis, primary sclerosing cholangitis, hemochromatosis, and Wilson's disease can be treated using systems and methods as disclosed herein.

Inflammation of the gastrointestinal tract (e.g., colon and/or small intestine, including the duodenum, jejunum, and ileum; stomach; and/or the esophagus) is treated in several embodiments. In some embodiments, gastric acid and/or bile secretion and/or absorption is regulated via neuromodulation to, for example, beneficially affect intestinal inflammation and/or motility. In some embodiments, pancreatic enzyme secretion is altered to treat IBD, IBS and other GI conditions such as disclosed herein. In some embodiments neuromodulation as disclosed herein can modulate (increase or decrease) the release or effects of a GI-related hormone, peptide, chemical, or other agent including but not limited to bile acid, pancreatic enzyme, gastrin, secretin, cholecystokinin (CCK), vasointestinal peptide (VIP), enterocrinin, motilin, vilikinin, somatostatin, and/or gastric acid, by about or at least about 5%, 10%, 15%, 20%, 25%, 30%, 35%, 40%, 45%, 50%, 60%, 70%, 80%, 90%, 100%, or more, or incorporating two of the aforementioned values. In some embodiments, neuromodulation can treat or prevent fecal incontinence, or increase or decrease GI motility to treat, for example, gastroparesis, ileus, large or small bowel obstruction, constipation, or diarrhea.

In some embodiments, systems and methods as disclosed herein can treat systemic autoimmune diseases, including but not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Degos disease, dermatomyositis, juvenile dermatomyositis, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin dependent diabetes (Type I), juvenile rheumatoid arthritis (JRA), Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In some embodiments, disclosed herein is a system for treating inflammatory bowel diseases in a patient. The system can include a peripheral nerve stimulator including a pulse generator and at least two, three, or more electrodes configured to deliver electrical stimulation to one, two, three, or more nerves, acupressure points, or meridians in the patient's limbs, and spaced apart from the patient's abdomen and related GI organs. The stimulation can be sufficient in some embodiments to change, e.g., reduce or improve one or more of: mRNA proinflammatory cytokines (e.g., IL-1, IL-2, IL-6, IL-8, TNFα), myeloperoxidase activity (MPOA), macroscopic index of colitis, clinical disease index, endoscopic index, erythrocyte sedimentation rate (ESR), C-reactive protein, fecal calprotectin, symptoms such as pain (such as abdominal pain or cramping), nausea, vomiting, diarrhea, constipation, or gastrointestinal transit. In some embodiments, inflammatory cytokines, biomarkers, or other indexes including those noted above are reduced or improved post-treatment with the devices disclosed herein by at least about 5%, 10-20%, 20-40%, 40-60% or more (including overlapping ranges therein) compared to pre-treatment.

The method can include, in some embodiments, any number of the following: positioning a first peripheral nerve effector on the patient's skin to stimulate a first peripheral nerve target of the patient; positioning a second peripheral nerve effector on the patient's skin to stimulate the a second nerve target of the patient; delivering a first electrical nerve stimulation signal transcutaneously to the first nerve through the first peripheral nerve effector; delivering a second electrical nerve stimulation signal transcutaneously to the second nerve through the second peripheral nerve effector; receiving an input relating to autonomic nervous system activity of the patient; and modifying at least one brain, brain stem, or spinal cord autonomic circuit relating to the inflammation response of a patient based on the input to balance parasympathetic and sympathetic nervous system activity of the patient. In some embodiments, the first nerve can be the tibial nerve, and the second nerve can be the saphenous nerve. In other embodiments, the first nerve can be the auricular vagus nerve and the second nerve can be the median nerve. In some embodiments, the method does not utilize any implantable components, and only involves transcutaneous stimulation. The first electrical stimulation signal can be different from the second electrical stimulation signal. The first electrical stimulation signal can have a first frequency different from a second frequency of the second electrical stimulation signal. The first electrical stimulation signal can have an amplitude different from the second electrical stimulation signal. The first or second frequency can be, for example, from about 5 Hz to about 20 Hz. The first or second frequency can be, for example, from about 10 Hz to about 100 Hz. Receiving an input relating to autonomic nervous system activity of the patient can include any number of the following: receiving data from a sensor that measures autonomic nervous system activity of the patient; receiving data from a sensor that measures heart rate variability of the patient; receiving heart rate variability data from an optical sensor measuring blood flow characteristics and disposed proximate a vessel proximate a wrist, knee, ankle, or ear of the patient; receiving data from a sensor that measures galvanic skin response of the patient; receiving data relating to inflammatory symptoms of the patient; and/or receiving data relating to bowel events of the patient, which can include bowel movements, urgency, and incontinence events. In some embodiments, stimulation, e.g., transcutaneous stimulation of a plurality of peripheral nerves that are remote from the abdomen and/or do not directly innervate the GI tract, e.g., stomach or intestines can surprisingly and unexpectedly treat inflammatory bowel disease, other inflammatory diseases, and other medical conditions as disclosed elsewhere herein.

In some embodiments, disclosed herein is a method of treating symptoms associated with inflammatory bowel diseases in a patient. The method can include any number of the following: positioning a first electrode at a first location on a skin surface relative to a first afferent peripheral nerve; positioning a second electrode at a second location on the skin surface relative to a second afferent peripheral nerve; positioning a third electrode at a third location on the skin surface spaced apart from the first electrode and the second electrode; delivering a first stimulus to the first peripheral nerve through the first electrode; and delivering a second stimulus to the second peripheral nerve through the second electrode. In some embodiments, the third electrode is a single common return electrode to the first electrode and the second electrode. In some embodiments, the first electrode, second electrode, and third electrode are positioned such that electric fields between the first electrode and the third electrode pass through the first afferent peripheral nerve, and electric fields between the second electrode and the third electrode pass through the second afferent peripheral nerve. The first stimulus and the second stimulus can modify at least one brain, brain stem, or spinal cord autonomic circuit relating to gastrointestinal function. In some embodiments, the first afferent peripheral nerve comprises the tibial nerve. In some embodiments, the second afferent peripheral nerve comprises the saphenous nerve. In some embodiments, the first electrode, second electrode, and third electrode are all connected on a wearable device and positioned on the calf proximate to, and distal to the patient's knee, ankle, and/or foot; or positioned on the wrist or arm.

In some embodiments, disclosed herein is a method of treating symptoms associated with inflammatory bowel diseases in a patient. The method can include any number of the following: positioning a first pair of electrodes comprising an anode and a cathode at a first location on a skin surface relative to a first peripheral nerve; positioning a second pair of electrodes comprising an anode and a cathode at a second location on the skin surface relative to a second peripheral nerve; delivering a first stimulus to the first peripheral nerve through the first pair of electrodes; and delivering a second stimulus to the second peripheral nerve through the second pair of electrodes. In some embodiments, the first pair of electrodes and second pair of electrodes are positioned such that electric fields between the first pair of electrodes pass through the first peripheral nerve, and electric fields between the second pair of electrodes pass through the second peripheral nerve. The first stimulus and the second stimulus can modify at least one brain or spinal cord autonomic feedback loop relating to a particular physiologic function, such as immune system regulation for example.

In some embodiments, disclosed herein is a wearable device for treating gastrointestinal symptoms in a patient. The device can include any number of the following: a controller; a first peripheral nerve effector, comprising at least one stimulation electrode configured to be positioned to transcutaneously modulate a first afferent nerve pathway associated with the inflammation response of a patient; and a second peripheral nerve effector, comprising at least one stimulation electrode configured to be positioned to transcutaneously modulate a second afferent nerve pathway associated with the inflammation response of a patient; and at least one input source configured to provide feedback information. The controller can include a processor and a memory for receiving the real-time feedback information from the input source that, when executed by the processor, cause the device to adjust one or more parameters of a first electrical stimulus based at least in part on the feedback information; adjust one or more parameters of a second electrical stimulus based at least in part on the feedback information independent from the first electrical stimulus; deliver the first electrical stimulus to a first afferent nerve pathway through the first peripheral nerve effector to reduce gastrointestinal symptoms by modifying a first brain, brain stem, or spinal cord autonomic circuit relating to gastrointestinal function; and deliver the second electrical stimulus to a second afferent nerve pathway through the second peripheral nerve effector to reduce gastrointestinal symptoms by modifying a second brain, brain stem, or spinal cord autonomic circuit relating to gastrointestinal function. Adjusting the one or more parameters of the first electrical stimulus and the second electrical stimulus can contribute to balancing sympathetic and parasympathetic nervous system activity.

In some embodiments, systems and methods can include a wearable device with an electrically conductive skin interface that excite the underlying nerves from a transcutaneous surface stimulator. The device may be sized for a range of user sizes with stimulation electrodes positioned to target the appropriate nerves, as in the device described in, for example, U.S. Pat. No. 9,452,287 to Rosenbluth et al., U.S. Pat. No. 9,802,041 to Wong et al., PCT Pub. No. WO 2016/201366 to Wong et al., PCT Pub. No. WO 2017/132067 to Wong et al., PCT Pub. No. WO 2017/053847 to Hamner et al., PCT App. No. PCT/US2017/040920 to Wong et al., and PCT App. No. PCT/US2017/048424 to Rosenbluth et al. filed on Aug. 24, 2017, each of which is incorporated by reference in their entireties.

Some embodiments include a wearable system that uses transcutaneous sensory stimulation in order to improve symptoms of inflammatory bowel disease and/or fecal incontinence. In some embodiments, key factors of this system enable chronic, home-use to improve the efficacy of peripheral nerve stimulation by avoiding the inconvenience of frequent office visits and invasive aspects of using percutaneous or implanted nerve stimulation. Some embodiments can advantageously utilize transcutaneous neuromodulation of peripheral afferent nerve pathways to non-invasively affect brain, brain stem, or spinal cord pathways associated with the inflammation response in a patient.

Chronic peripheral nerve stimulation in a wearable form that can be integrated into activities of daily living, allowing full mobility and ease of use, can improve the efficacy of neuromodulation. However, home use of a percutaneous system can be inconvenient and technically difficult for the patient. Transcutaneous neuromodulation is a more suitable modality for home use but is currently limited by the form factor depending on the needs for chronic daily use. Furthermore, adding aspects of responsiveness and more frequent use could greatly improve the effectiveness and comfort of such a chronic use device.

The effects of peripheral nerve stimulation on inflammatory response and gastrointestinal function may occur only during the period of active stimulation or may outlast the stimulation period after stimulation has ceased. Different mechanisms such as the modulation of spinal reflexes or induction of brain or spinal plasticity can be responsible for these experimental and clinical observations. Furthermore, the onset of the effects of stimulation may occur acutely (e.g., during or immediately following therapy) or only after several stimulation sessions in a chronic manner. For example, the effect of transcutaneous tibial nerve stimulation on patient related outcomes is estimated at 4-6 weeks after the initiation of weekly stimulation sessions. Depending on the underlying mechanisms and the time course of beneficial effects, stimulation may require delivery in a continuous fashion such as in sacral nerve stimulation, in discrete scheduled sessions or in an on-demand, conditional manner.

In some embodiments, disclosed herein is a wearable device for inducing neural plasticity in a user with transcutaneous electrical stimulation of an afferent peripheral nerve. The device can include any number of a controller; a first peripheral nerve effector, comprising at least one stimulation electrode configured to be positioned to transcutaneously modulate a first afferent peripheral nerve; and at least one biomedical sensor or data input source configured to provide feedback information. The controller can include a processor and a memory for receiving the feedback information from the sensor, that when executed by the processor, cause the device to adjust one or more parameters of a first electrical stimulus based at least in part on the feedback information; and/or deliver the first electrical stimulus to the first afferent peripheral nerve to the first peripheral nerve effector. The first electrical stimulus can include patterned, such as burst (e.g., theta burst) electrical stimulation configured to induce neural plasticity. The stimulation can be continuous, intermittent, or intermediate theta burst stimulation in some embodiments. The device can also be configured to deliver a priming electrical nerve stimulation signal prior to the first electrical stimulation signal, which can be a non-theta burst stimulation signal. The device can further include a second peripheral nerve effector, including at least one stimulation electrode configured to be positioned to transcutaneously modulate a second afferent peripheral nerve, and is configured to deliver a second electrical nerve stimulation signal transcutaneously to the afferent peripheral nerve of the user. The signal can include, for example, electrical theta burst stimulation.

Also disclosed herein is a method for treating inflammatory bowel disease, that can include assessing at least one of sympathetic and parasympathetic activity of a subject and determining the presence of sympathetic or parasympathetic overactivity or underactivity in the subject; and stimulating a first peripheral nerve sufficient to have a therapeutic effect on the inflammatory response of a patient if abnormal sympathetic activity is present; and/or stimulating the a second peripheral nerve sufficient to have a therapeutic effect on inflammatory bowel disease if abnormal parasympathetic activity is present. In some embodiments, stimulating comprises only electrical transcutaneous stimulation. The stimulation can include inhibiting or exciting nerve activity of one, two, three or more peripheral nerve targets. Sympathetic and parasympathetic activity of a subject can include measuring heart rate variability (HRV), such as via a wrist-worn device. Other parameters such as heart rate and electrodermal activity can be measured in addition or alternatively. HRV can be measured during a predefined period of time, such as 24 hours, either prior to and/or after the initial stimulation.

Also disclosed herein in some embodiments is a method for treating inflammatory bowel disease, that can include electrically stimulating a first nerve associated with inflammatory response in a patient; assessing at least one of sympathetic and parasympathetic activity of a subject and determining the presence or absence of sympathetic or parasympathetic overactivity in the subject; assessing symptomatology of inflammatory bowel disease; and adjusting the electrical stimulation based upon assessing the at least one of sympathetic and parasympathetic activity and the symptomatology of inflammatory bowel disease. Adjusting the electrical stimulation can include, for example, identifying sympathetic or parasympathetic overactivity in the patient, and adjusting the frequency of stimulation of the first nerve; and/or discontinuing electrical stimulation of the first nerve associated with inflammatory response in a patient; and initiating electrical stimulation of a second nerve associated with inflammatory response in a patient. In some embodiments, current level can be held constant as frequency is adjusted to maximize activation. In some embodiments, pulse width can be held constant as frequency is adjusted to maximize activation. In some embodiments, current level and pulse width can be held constant as frequency is modified to maximize activation. In some embodiments, targeting afferent fibers, current or voltage level may be determined by finding a minimum sensory threshold for each individual or before each stimulation session. In some embodiments, targeting efferent fibers, current or voltage level may be determined by finding a muscle contraction threshold for each nerve on each individual or before each stimulation session.

In some embodiments, the neuromodulation device (e.g., the neurostimulator) is placed proximate the wrist, arm, foot, ankle, calf, thigh, and/or ear of the patient.

According to several embodiments, the neurostimulation embodiments described herein work synergistically with pharmacological agents. In light of the already sensitive and inflamed digestive system of many patients with inflammatory bowel diseases and other gastrointestinal conditions, this synergy is particularly beneficial because the patient, in one embodiment, will need an overall lower dosage of the pharmacological agent to achieve an efficacy comparable (or better) to that achieved without neurostimulation. This results in fewer undesired side effects in several embodiments.

In some embodiments, disclosed herein is a method for treating symptoms of an inflammatory gastrointestinal disease in a patient with transcutaneous stimulation of a peripheral nerve. The method can include any number of the following: positioning a first peripheral nerve effector on the patient's skin to stimulate the peripheral nerve of the patient; delivering a first electrical nerve stimulation signal transcutaneously to the peripheral nerve through the first peripheral nerve effector; receiving an input relating to activation of the first peripheral nerve; calculating one or more features from the input relating to activation at least based in part on a nerve conduction velocity of the first peripheral nerve; adjusting an electrical stimulation parameter based on one or more features of the nerve conduction velocity of the first peripheral nerve to maximize activation of a first preselected nerve fiber type, and modifying at least one brain or spinal cord autonomic feedback loop relating to release of neurotransmitters from the autonomic nervous system that modulate synthesis of inflammatory biomarkers and reduce inflammation relating to the inflammatory gastrointestinal disease.

The method can also include any number of positioning a second peripheral nerve effector on the patient's skin to stimulate a second peripheral nerve of the patient; delivering a second electrical nerve stimulation signal transcutaneously to a second peripheral nerve through the second peripheral nerve effector; adjusting an electrical stimulation parameter based on one or more features of a nerve conduction velocity of the second peripheral nerve to maximize activation of a second preselected nerve fiber type, and modifying at least one brain or spinal cord autonomic feedback loop relating to release of neurotransmitters from the autonomic nervous system that modulate synthesis of inflammatory biomarkers and reduce inflammation relating to the inflammatory gastrointestinal disease. The preselected nerve fiber type can be, for example, A-alpha, A-beta, A-delta, A-gamma, and B fibers. Adjusting the electrical stimulation parameter can include adjusting at least one of a pulse width or a pulse duration of the electrical stimulation to within about 10%, within about 5%, or about the chronaxie of the first preselected nerve fiber type. Adjusting the electrical stimulation parameter can include adjusting at least one of a pulse width or a pulse duration of the electrical stimulation to about the chronaxie of the first preselected nerve fiber type. The nerve conduction velocity could be measured orthodromically and/or antidromically.

In some embodiments, the first peripheral nerve and the second peripheral nerve do not directly innervate abdominal organs, including but not limited to the esophagus, stomach, small intestines, large intestines, liver, spleen, pancreas, and/or gallbladder. In some embodiments, the first peripheral nerve and the second peripheral nerve are not within the abdomen. In some embodiments, the first peripheral nerve and the second peripheral nerve are not a branch of the vagus nerve, or not a cervical branch of the vagus nerve.

In some embodiments, disclosed herein is a wearable device for treating symptoms of an inflammatory gastrointestinal disease in a patient with transcutaneous stimulation of one or more peripheral nerves. The device can include a controller. The device can also include a first peripheral nerve effector, including at least one, two, or more stimulation electrodes configured to be positioned on the skin to stimulate a first peripheral nerve of the patient. The device can also include a first sensor or data input source, including at least one sensing electrode configured to be positioned on the skin to measure activity of the first peripheral nerve. The controller can include a processor and a memory for receiving the feedback information from one or more sensors that, when executed by the processor, cause the device to calculate one or more features of nerve conduction velocity of the first peripheral nerve based at least in part on the feedback information of the first sensor; adjust one or more parameters of a first electrical stimulus based at least in part one or more features of nerve conduction velocity to maximize activation of a preselected fiber type in the first peripheral nerve, and/or deliver a first electrical stimulus to a first peripheral nerve through the first peripheral nerve effector to modify at least one brain or spinal cord autonomic feedback loop relating to release of neurotransmitters from the autonomic nervous system that modulate synthesis of inflammatory biomarkers and reduce inflammation relating to the inflammatory gastrointestinal disease.

In some embodiments, a device can also include a second peripheral nerve effector, including at least one stimulation electrode configured to be positioned on the skin to stimulate a second peripheral nerve of the patient; and a second sensor or data input source, including at least one sensing electrode configured to be positioned on the skin to measure activity of the second peripheral nerve. The controller can include a processor and a memory for receiving the feedback information from one or more sensors that, when executed by the processor, cause the device to: calculate one or more features of nerve conduction velocity of the second peripheral nerve based at least in part on the feedback information of the second sensor; adjust one or more parameters of a second electrical stimulus based at least in part one or more features of nerve conduction velocity to maximize activation of a preselected fiber type in the second peripheral nerve, and/or deliver a second electrical stimulus to a second peripheral nerve through the second peripheral nerve effector to modify at least one brain or spinal cord autonomic feedback loop relating to release of neurotransmitters from the autonomic nervous system that modulate synthesis of inflammatory biomarkers and reduce inflammation relating to the inflammatory gastrointestinal disease.

The preselected nerve fiber type can be, for example, A-alpha, A-beta, A-delta, A-gamma, and B fibers. The device can be configured to adjust the electrical stimulation by adjusting at least one of a pulse width or a pulse duration of the electrical stimulation to within about 10%, within about 5%, or about the chronaxie of the first preselected nerve fiber type. Adjusting the electrical stimulation parameter can include adjusting at least one of a pulse width or a pulse duration of the electrical stimulation to about the chronaxie of the first preselected nerve fiber type. The nerve conduction velocity could be measured orthodromically and/or antidromically.

In some embodiments, the device is configured such that the first peripheral nerve and the second peripheral nerve do not directly innervate abdominal organs, including but not limited to the esophagus, stomach, small intestines, large intestines, liver, spleen, pancreas, and/or gallbladder. In some embodiments, the first peripheral nerve and the second peripheral nerve are not within the abdomen. In some embodiments, the first peripheral nerve and the second peripheral nerve are not a branch of the vagus nerve, or not a cervical branch of the vagus nerve.

BRIEF DESCRIPTION OF THE DRAWINGS

FIGS. 6B and 6C illustrate views of stimulation devices with sticky electrodes, according to some embodiments of the invention.

FIGS. 6I-6K schematically illustrates a flow chart incorporating a stimulation protocol, according to some embodiments of the invention, including a sample diagnosis, prescription, and usage workflow.

FIGS. 6L-6N illustrate non-limiting embodiments of potential electrode placement locations for nerve stimulation.

FIGS. 6O and 6P illustrate embodiments of stimulation systems with at least three electrodes that can be configured to independently stimulate a plurality of nerves.

FIG. 10A illustrates how inflammatory products produced in damaged tissues activate afferent neural pathways that signal the nucleus tractus solitarius; subsequent activation of vagus efferent fibers inhibits cytokine synthesis through a cholinergic anti-inflammatory pathway. FIG. 10A also illustrates a neural pathway where activation of sympathetic outflow can increase local concentrations of adrenaline and noradrenaline, which can suppress inflammation further. FIG. 10B illustrates a neural pathway signaling efferent activity in the vagus nerve that leads to acetylcholine (ACh) release in organs of the reticuloendothelial system, including the liver, heart, spleen and gastrointestinal tract. Acetylcholine interacts with α-bungarotoxin-sensitive nicotinic receptors (ACh receptor) on tissue macrophages, which inhibit the release of TNF, IL-1, HMGB1 and other inflammatory cytokines.

FIGS. 12A-12D illustrate various views of an embodiment of a device and system that provides peripheral nerve stimulation, targeting individual nerves, to prevent or treat inflammatory bowel disease or other inflammatory conditions.

FIGS. 14A-14E illustrate another embodiment of a wearable therapy system.

DETAILED DESCRIPTION

Figure 1:
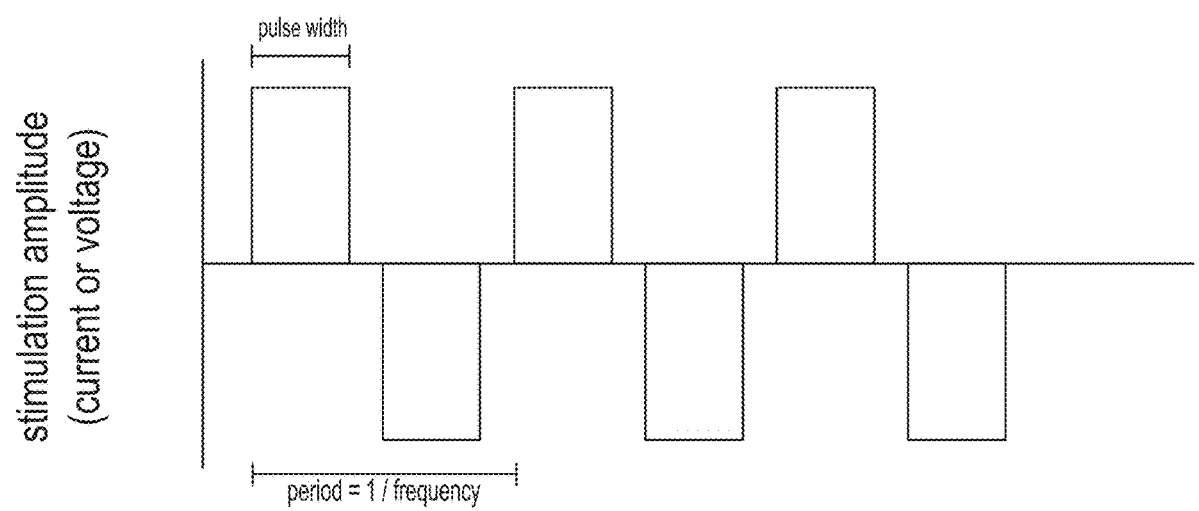
FIG. 1 illustrates various views of an embodiment of a device and system that provides peripheral nerve stimulation, targeting individual nerves, to reduce inflammation of the GI tract and other symptoms associated with inflammatory bowel disease.

Several embodiments of the invention relate generally to the treatment of inflammatory bowel diseases and chronic inflammation of the digestive tract which may be due to an autoimmune response, including ulcerative colitis, Crohn's disease, microscopic colitis, and irritable bowel syndrome, and more specifically to systems and methods of treating inflammatory bowel diseases, including ulcerative colitis, Crohn's disease, and microscopic colitis through noninvasive peripheral nerve stimulation. Other non-limiting examples of indications for systems and methods as disclosed herein are also disclosed. Not to be limited by theory, some mechanism of actions including pathways that can be utilized by systems and methods as disclosed herein will now be described. Stimulation of peripheral nerves, such as, for example, vagus, median, radial, ulnar, tibial, sacral, or saphenous nerve can modulate autonomic tone. In some embodiments, there can be a synergistic effect of modulating both the parasympathetic and sympathetic nervous systems in activating the anti-inflammatory pathway. Activation of parasympathetic outflow can inhibit cytokine synthesis by release of acetylcholine, which bind to microphages in the blood stream to inhibit the release of TNF. Activation of the sympathetic outflow can increase local concentrations of adrenaline and noradrenaline, which can suppress inflammation further by inhibiting the release of TNF.

In some embodiments and not to be limited by theory, stimulation of specific peripheral nerves such as, for example, the vagus and/or tibial nerves can modulate parasympathetic tone; the saphenous nerve, among others can modulate sympathetic tone. Some nerves, such as, for example, the median, radial, or ulnar nerves can modulate sympathetic and parasympathetic tone, depending on the parameters of the electrical waveform used to stimulate the nerve.

Not to be limited by theory, stimulation of peripheral nerves can enhance maintenance of homeostasis of the autonomic nervous system. For example, a change of sympathetic outflow can trigger a subsequent change of the parasympathetic outflow to maintain homeostasis of the autonomic nervous system. Thus, acute, repeated increases in sympathetic outflow by stimulation of peripheral nerves may also increase parasympathetic outflow, which then increases release of acetylcholine and inhibition of cytokine synthesis to reduce symptoms associated with chronic inflammation. In another example, a change in parasympathetic outflow can trigger a subsequent change of sympathetic outflow. Thus, acute, repeated, increases in parasympathetic outflow by stimulation of peripheral nerves may also increase sympathetic outflow. In some embodiments, stimulation of peripheral nerves may increase or decrease sympathetic and parasympathetic activity, which increases or decreases overall autonomic tone but maintains homeostasis.

In some embodiments, sympathetic and parasympathetic activity can be measured with body-worn sensors, including but not limited to pulse or heart rate, heart rate variability, electrocardiogram (ECG or EKG), electrodermal activity or galvanic skin response, blood pressure, skin temperature, pupil dilation. Pulse, heart rate, or electrocardiogram sensors can measure changes in electrical activity when worn on the hand, wrist or chest, typically with multiple leads, or can use optical sensors as part of a photoplethysmogram system that measure changes in blood flow to calculate heart rate. Electrodermal activity or galvanic skin response, signal that reflects the action of sympathetic nerve traffic on eccrine sweat glands, measures changes in electrical properties of the skin, such as resistance, in the presence of a small electrical current or differences in the electrical potential between different parts of the skin. Blood pressure measurement devices measure changes in blood pressure during cardiac activity using an inflatable cuff, typically placed on the arm, wrist or fingers. Blood pressure can also be measured with other sensors placed on the skin, such as accelerometers or strain sensors that measure displacement of blood vessels. Skin temperature can be measured with a thermistor, thermocouple, or temperature sensor placed on the skin. Pupil dilation can be measured optically with image processing of video data, where for example, the video camera is disposed in a wearable set of eye glasses.

The vagus nerve is the longest nerve in the body and innervates numerous organs, including the organs within the gastrointestinal tract. The vagus nerve is the major neural pathway for the parasympathetic branch of the autonomic nervous system and is a mixed nerve that includes approximately 80% afferent fibers and 20% efferent fibers. The efferent fibers of the vagus nerve contribute to control of GI motility and secretion.

Afferent vagus nerve fibers synapse bilaterally on the Nucleus Tractus Solitarius (NTS) in the dorsal medulla. The NTS sends information to efferent (e.g., 30 premotor) parasympathetic nuclei located in the medulla. These efferent regions include the dorsal motor nucleus of the vagus (DMNX) and the nucleus ambiguus (NAmb), and outflow from these regions course through efferent fibers of the vagus nerve. The NTS also transfers information to the parabrachial nucleus (PBN) in the pons, which then relays signals to the visceral primary sensorimotor cortex. Moreover, the DMNX, NAmb, and NTS further communicate with a set of brain regions including the Locus coeruleus (LC, noradrenergic), rostral Ventromedial Medulla (rVMM, serotoninergic), midbrain periaqueductal gray (PAG), hypothalamus, amygdala, and dorsomedial prefrontal and anterior cingulate cortices. Thus, the NTS connects with a diffuse system of brain regions. Thus, stimulation of vagal afferents induces vagal outflow, such as though NTS/NAmb connectivity.

The auricular vagus nerve is a branch of the vagus nerve that innervates the ear in the area of the cymba concha, cavum, and/or tragus. The auricular vagus is accessible for electrical stimulation by transcutaneous or percutaneous electrodes.

Generally, the GI tract is innervated by the sacral parasympathetic fibers through the pelvic nerves originating in the S2 to S4 spinal segments, and lumbothoracic sympathetic fibers originating in the T11 to L2 segments of the spinal cord. The sympathetic fibers travel through the hypogastric nerve and inferior mesenteric ganglia, while the parasympathetic fibers travel in the pelvic nerves and plexus. Any number of the foregoing nerves, among others, can be modulated with systems and methods as disclosed herein. In some cases, effective frequency band for parasympathetic modulation can be, for example, around the frequency band of 10 to 20 Hz, while the frequency band for sympathetic modulation can be, in some cases, as high as 30 Hz or as low as 5 Hz. In a further embodiment, current level can be held constant as frequency is adjusted to maximize activation, or vice versa (frequency held constant, current level adjusted). In an additional embodiment, pulse width can be held constant as frequency is adjusted to maximize activation. In an additional further embodiment, current level and frequency can be held constant as pulse width is modified to maximize efficacy. In an additional further embodiment, current level and pulse width can be held constant as frequency is modified to maximize activation. In a further embodiment targeting afferent fibers, current or voltage level may be determined by finding a minimum sensory threshold for each individual or before each stimulation session. In a further embodiment targeting efferent fibers, current or voltage level may be determined by finding a muscle contraction threshold for each nerve on each individual or before each stimulation session.

In some embodiments, systems and methods can involve stimulation parameters including frequency and spatial selectivity on the surface of the distal limb to selectively modulate and balance the sympathetic and parasympathetic system.

Not to be limited by theory, stimulation of a first target nerve, such as the saphenous nerve can provide sympathetic modulation of the anti-inflammatory pathway. Specifically, electrical stimulation tuned to excite large myelinated fibers in a target nerve, e.g., the saphenous nerve can provide somatic afferent input to the lumbar plexus, mediating the sympathetic input to the GI tract via the hypogastric nerve. Sympathetic nerves increase local concentrations of adrenaline and noradrenaline, which can suppress inflammation in the GI tract by inhibiting the release of TNF. Stimulation of a second target nerve, e.g., the tibial nerve can provide parasympathetic modulation of the anti-inflammatory pathway. Specifically, electrical stimulation tuned to excite large myelinated fibers in the tibial nerve provides somatic afferent input to sacral plexus, mediating parasympathetic input to the GI tract via the pelvic nerves via release of cholinergic transmitters that bind to microphages in the blood stream to inhibit the release of TNF.

In general, stimulation of superficial and/or cutaneous afferent and/or efferent nerves can prevent an inflammatory response by inhibiting the nucleus of the solitary tract and vagal nuclei. Stimulation of deep afferent and/or efferent nerves can prevent an inflammatory response by exciting the arcuate nucleus-ventral periaqueductal gray-nuclei raphe pathway, inhibiting the rostral ventrolateral medulla (rVLM) and thereby the sympathetic outflow. Superficial fibers are finer (e.g., smaller diameter) afferents that relay sensory information to the superficial dorsal horn, which is a distinct region of the dorsal horn and spinal gray matter; deep fibers are thicker (e.g., larger diameter) afferents that relay sensory information to the deep dorsal horn.

Transcutaneous stimulation of one, two, or more target nerves of interest, e.g., the saphenous, tibial, median and/or vagus nerve stimulation can be effective. However, in some embodiments, transcutaneous stimulation can be preferred. The feasibility of home-based stimulation has been limited by device form factor and limited programming flexibility of current devices.

In some embodiments, more continuous stimulation at can potentially improve the efficacy of peripheral nerve stimulation for conditions such as, for example, inflammatory bowel disease. An implanted, transcutaneous, and/or percutaneous nerve stimulator can be efficacious and safe. Some embodiments can use frequencies of, for example, between about 1 kHz and about 100 kHz, 1 Hz and about 100 Hz, between about 1 Hz and about 50 Hz, between about 5 Hz and about 30 Hz, or between about 10 Hz and about 20 Hz stimulation for a specified period of time, such as about, at least about, or no more than about 20, 30, 40, 50 or 60, 90, 120, or 240 minutes at a sensory or sub-sensory threshold or below motor contraction threshold that is tolerable to the patient. Varying the regularity of stimulation and the frequency of the stimulation waveform may improve tolerance or efficacy in some cases. An increased frequency of stimulation may be more effective but could require a more chronic at-home portable system to provide continuous transcutaneous stimulation throughout the day. In some embodiments, stimulation of a target nerve can utilize a frequency of between about 5 Hz and about 200 Hz, between about 2 Hz and about 150 Hz, or about 2 Hz, 5 Hz, 10 Hz, 20 Hz, 30 Hz, 40 Hz, 50 Hz, 60 Hz, 70 Hz, 80 Hz, 90 Hz, 100 Hz, 110 Hz, 120 Hz, 130 Hz, 140 Hz, 150 Hz, 160 Hz, 170 Hz, 180 Hz, 190 Hz, 200 Hz, or ranges including any two of the foregoing values. In some embodiments, the target nerve is the tibial nerve or the saphenous nerve. In some embodiments, the target nerve is the median nerve or the ABVN.

Stimulating at intensities below the sensory threshold or with high frequencies (e.g., between about 1 kHz to about 100 kHz) can avoid the discomfort (tingling, numbness, pain) that can be associated with peripheral nerve stimulation. Because the exact electrode position, size and surface contact can have a large effect on the stimulation level and the anatomical structures that receive the stimulation, the sensory threshold may need to be calibrated for each patient and even for each session. This calibration may be done by the user manually setting the stimulation parameters or otherwise indicating their sensory threshold. Another possible embodiment is for the device to automatically sweep through a range of stimulation parameters and the patient chooses the most comfortable set of parameter values. Another possible embodiment is for the patient to choose from among a set of previously chosen parameter values that provided effective and comfortable stimulation.

The stimulation waveforms described herein can be applied continuously to target nerves, or can be provided in a manner that is adaptive in applying stimulation of various durations or by adjusting properties of the stimulation waveform to maximize efficacy, including but not limited to current or voltage amplitude, frequency, and pulse width, in response to different inputs in the system. In some embodiments, the system could include closed loop control, using one or more signals measured by the device or feedback input into the device by the patient or physician to modulate the stimulation to improve efficacy. The signals or input could include, for example, any number of the following: sensors on-board the device or sensor in other devices with data stored in a remote server via wireless communicates (e.g., data stored in a cloud server via cellular connection) or sensors in other devices in direct communication with the stimulator, either wired or wirelessly; evaluation of autonomic function, reflex loop integrity, or excitability using heart rate variability, galvanic skin response, or pupil dilation, measuring muscle sympathetic nerve activity (MSNA), and/or measuring h-reflex by sending a stimulation signal and measure response with EMG. In some embodiments, the signals or input can also include sleep sensor sets, including but not limited to accelerometers, gyroscopes, infrared based motion sensors, and/or pressure sensors under a mattress, to measure night time motion as a measure of night time bowel events. For example, patients may wear a stimulator while sleeping and therapy can be triggered by night time restlessness, which is an indicator of an upcoming event. An EEG headband could be used to measure different sleep states. Patient and/or physician input can provide feedback on the effectiveness of and/or satisfaction with the therapy into the device or into another connected device. Also, usage of the stimulation device can be tracked; and specific stimulation programs (e.g., a specified set of stimulation parameters) can be changed based on symptoms presented by the patient or outcomes of the therapy. In a further embodiment, current level can be held constant as frequency is adjusted to maximize efficacy. In an additional embodiment, pulse width can be held constant as frequency is adjusted to maximize efficacy, or vice versa (pulse width adjusted, frequency held constant). In an additional further embodiment, current level and pulse width can be held constant as frequency is modified to maximize efficacy. In an additional further embodiment, current level and frequency can be held constant as pulse width is modified to maximize efficacy.

In some embodiments, a stimulator can be part of a system with sensors to assess the state of sleep and modulate stimulation based on the wearer's sleep state. Sensors could include motion sensors (e.g., body worn accelerometers and gyroscopes, or wireless motion tracking via video or infrared), temperature sensors to measure body temperature, pressure sensor under the mattress to measure movement, heart rate sensors to measure HRV, other sensors to measure sympathetic and parasympathetic activity, and/or EEG sensors to measure brain activity to assess the wearer's sleep state. For example, if night time events occur during slow wave sleep when parasympathetic activity can be elevated, stimulation parameters are modulated to affect parasympathetic activity, and vice-versa for sympathetic activity.

In some embodiments, a first stimulation frequency can be provided for short term benefit, and a second stimulation frequency different (e.g., higher or lower) from the first stimulation frequency can be provided for long-term benefit. For example, 10 Hz stimulation can provide a short term benefit and 20 Hz stimulation can provide a long term benefit in some cases. As one example, 10 Hz stimulation can be provided in an initial period with the therapy (e.g., 3 weeks) for acute therapy, then 20 Hz stimulation can be provided for long term maintenance or condition therapy, or vice versa depending on the desired clinical result. In some embodiments, particular sympathetic and/or parasympathetic nervous system targets and circuits can be specifically targeted to modulate upward or downward sympathetic and/or parasympathetic nervous system activity depending on the patient's underlying autonomic nervous system activity. Utilization of data and/or sensors directly or indirectly measuring sympathetic and/or parasympathetic nervous system activity as disclosed, for example, elsewhere herein can be utilized as closed loop feedback inputs into a hardware and/or software controller to modify stimulation parameters, including on a near real-time basis.

In some embodiments, the therapy (e.g., stimulation) can be applied for about, at least about, or no more than about 5 minutes, 10 minutes, 15 minutes, 30 minutes, 45 minutes, 1 hour, 2 hours, 3 hours, 4 hours, 5 hours, 6 hours, or more a day. In some embodiments, the patient is treated nocturnally, such as during sleep, and/or during waking hours. The treatment can be repeated 1, 2, 3, 4, 5, or more times daily or weekly, every other day, every third day, weekly, or other interval depending on the desired clinical result.

In some embodiments, the responsiveness could be dependent on different times of day. In some embodiments, stimulation schemes are applied to restore autonomic dysregulation based on natural diurnal patterns of sympathetic or parasympathetic activity. Treatment could also occur at irregular intervals that are human-entered or predicted by machine learning from previous days' voiding incidents. In some embodiments, a first frequency (e.g., 10 Hz or 20 Hz) therapy can be applied in the morning for acute day time relief, and a second different higher or lower frequency (e.g., 20 Hz or 10 Hz) therapy can be provided before bed for longer night time relief.

In some embodiments, specific fiber types within a nerve or nerves can be selectively activated (e.g., create action potentials in such specific fiber types) to restore autonomic balance by specifically modulating sympathetic and parasympathetic limbs of the autonomic nervous system (e.g., selectively only one, or more than one of A-alpha, A-beta, A-delta, B, and/or C fibers; afferent fibers or efferent fibers, sympathetic or parasympathetic). In some embodiments, systems and methods do not stimulate or substantially stimulate A-alpha, A-beta, A-delta, B fibers, or C fibers.

Some embodiments can include preferential stimulation of cutaneous fibers (e.g., A-alpha, A-beta, A-delta, and/or C; afferent or efferent, sympathetic or parasympathetic) fibers to inhibit sympathetic activity of via the stellate ganglion. Stimulation of select cutaneous fibers at the wrist can carry sensory information by way of the medial cutaneous nerve and the medial cord of the brachial plexus, which innervates the spinal cord at the level of C8-T1; stimulation in turn modulates sympathetic activity by way of the stellate or cervicothoracic ganglion, which are a collection of sympathetic nerves at the level of C7-T1.

Some embodiments can include preferential stimulation of efferent or afferent fibers of vagus nerve or other peripheral nerves to modulate systemic inflammation via the cholinergic parasympathetic system. For example, efferent stimulation of the vagus nerve may facilitate lymphocyte release from thymus through a nicotinic acetylcholine receptor response, and nicotine administration can be effective for treating some cases of inflammatory bowel disease. In some embodiments, afferent or efferent nerves may be preferentially stimulated by delivering stimulation at a level above or below the motor threshold (e.g., threshold of electrical potential required to active a nerve).

Not to be limited by theory, peripheral nerve fibers are classified based on the diameter, nerve conduction velocity, and the amount of myelination on the axons. These classifications apply to afferent and efferent fibers. Fibers of the A group have a large diameter, high conduction velocity, and are myelinated. The A group is further subdivided into four types: A-alpha (primary receptors of the muscle spindle and golgi tendon organ), A-beta (secondary receptors of the muscle spindle and cutaneous mechanoreceptors), A-delta (free nerve endings that conduct sensory stimuli related to pressure and temperature), and A-gamma (typically efferent neurons that control the activation of the muscle spindle) fibers. Fibers of the B group are myelinated with a small diameter and have a low conduction velocity. The primary role of B fibers is to transmit autonomic information. Fibers of the C group are unmyelinated, have a small diameter, and low conduction velocity. The lack of myelination in the C group is the primary cause of their slow conduction velocity. Additionally, for example, the vagus nerve consists of between 80-90% afferent fibers.

Some embodiments can include preferential stimulation of sympathetic or parasympathetic fibers of vagus nerve or parasympathetic nerves or fibers, sympathetic nerves or fibers, and/or other peripheral nerves to modulate systemic inflammation via the cholinergic parasympathetic system or sympathetically-driven release of adrenaline and noradrenaline, respectively. Preferential stimulation can be enabled by stimulating nerves within specific ranges of one or more electrical waveform parameters, including but not limited to current or voltage level, pulse width, stimulation frequency, inter-pulse spacing, waveform shape, and/or bursting frequency. In some embodiments, afferent fibers of a mixed peripheral nerve can be preferentially stimulated by adjusting the stimulation current or voltage to a level that does not induce muscle contraction, and thus is activating little to no efferent fibers. In another embodiment, larger diameter fibers at the same level of depth as other nerve fibers may be preferentially stimulated by adjusting voltage or current levels that are high enough to activate A-fibers, but not B- or C-fibers; or activate A- and B-fibers, but not C-fibers; or activate A-alpha and A-beta fibers, and A-delta fibers but not A-gamma, B-, or C-fibers.

Figure 17:
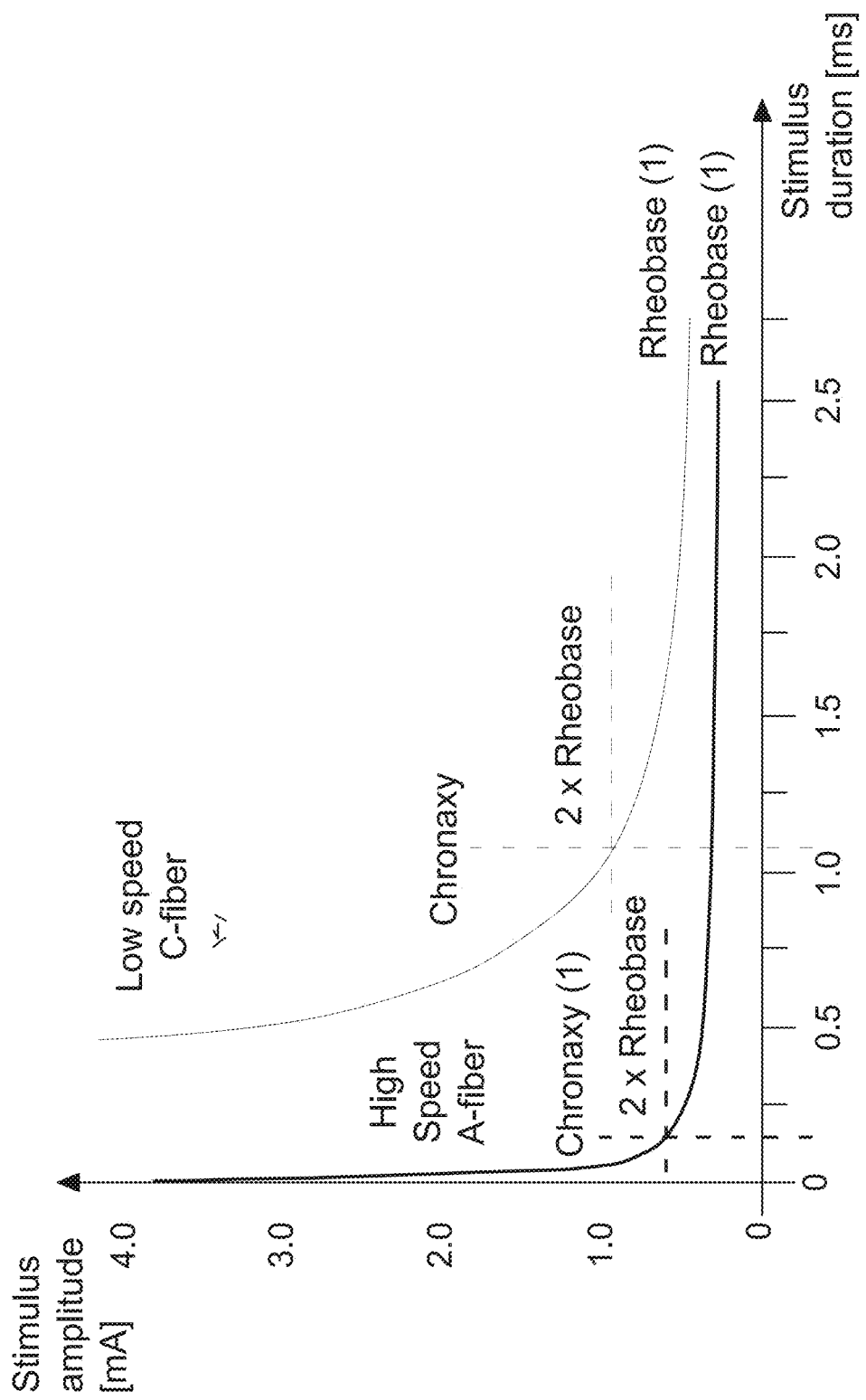
FIG. 17 illustrates preferential fiber activation of an A-fiber with respect to a C-fiber of a nerve.

Not to be limited by theory, chronaxie (chronaxy) is the minimum time required for an electric current, double the strength of the rheobase, to stimulate a nerve. Rheobase is the lowest current or voltage level, assuming an indefinite pulse width, required to stimulate a nerve or neuron. Chronaxie is dependent on the density of voltage-gated sodium channels in the cell, which affect that cell's excitability. Chronaxie varies across different nerves, neurons, and nerve fiber types. Stimulation pulse width (or pulse duration, depending on the shape of the waveform) can be modified to maximize activation of targeted neurons, nerves or nerve fibers based on the average chronaxie of the targeted nerve, neuron, or nerve fiber. In some embodiments, electrical pulses with the pulse width or pulse duration equal or nearly equal to the chronaxie are most effective (at relatively low amplitudes) to elicit action potentials. For example, Aα fibers can be activated at short pulse durations, such as about 0.1 ms, at relatively low current amplitudes while avoiding the stimulation of C-type pain fibers (FIG. 17). Typical chronaxie durations vary by fiber type, for example about 50-100 µs (Aα fibers), about 170 µs (Aδ fibers), and about 400 µs or greater (C fibers). In some embodiments, afferent fibers of various diameters or types can be preferentially stimulated by adjusting pulse width and/or frequency to deliver energy at a rate that maximized activation based on the average chronaxie dynamics of the specific neuron, nerve, or nerve fiber type targeted to be stimulated. In a further embodiment, current level can be held constant as pulse width and frequency are modified to maximize activation. In an additional embodiment, current level and frequency can be held constant as pulse width is modified to maximize activation. In an additional embodiment, current level and pulse width can be held constant as frequency is modified to maximize activation. In some embodiments, current level may be determined by finding a minimum sensory threshold for each individual or before each stimulation session. In a further embodiment of the system, one or more additional sensing electrodes can be placed along the pathway of the target nerve being stimulated that measure conduction velocity of the stimulated nerve to assess engagement of specific fiber types; pulse width can be modified to maximize activation of a specific fiber type corresponding to the measured conduction velocity. In some embodiments, stimulation can occur within about 25%, 20%, 15%, 10%, 9%, 8%, 7%, 6%, 5%, 4%, 3%, 2%, 1%, or less of the chronaxie, or ranges including any two of the foregoing values.

In another embodiment, afferent or efferent fibers can be preferentially stimulated by adjusting pulse width. For example, not to be limited by theory, shorter pulse widths (e.g., less than 200 µs) can preferentially activate efferent fibers, and longer pulse widths (e.g., greater than 500 µs) can preferentially activate afferent fibers. In some embodiments, the pulse width could be between about 50 µs and about 400 µs, such as about 50 µs, 100 µs, 150 µs, 200 µs, 250 µs, 300 µs, 350 µs, 400 µs, 450 µs, 500 µs, or ranges including any two of the foregoing values.

In a further embodiment, current level can be held constant as pulse width is modified to maximize activation. In an additional embodiment, frequency can be held constant as pulse width is modified to maximize activation. In an additional further embodiment, current level and frequency can be held constant as pulse width is modified to maximize activation. In a further embodiment targeting afferent fibers, current or voltage level may be determined by finding a minimum sensory threshold for each individual or before each stimulation session. In a further embodiment targeting efferent fibers, current or voltage level may be determined by finding a muscle contraction threshold. In a further embodiment of the system, one or more additional sensing electrodes can be placed along the pathway of the target nerve being stimulated that measure conduction velocity of the stimulated nerve to assess engagement of specific fiber types; pulse width can be modified to maximize activation of a specific fiber type corresponding to the measured conduction velocity.

In some embodiments, an electrical stimulation and sensing device can comprise a stimulation pulse generator configured to deliver an electrical stimulation to a patient, the electrical stimulation comprising a stimulation pulse delivered to a peripheral nerve of the patient via a first peripheral nerve effector placed on the patient's skin adjacent to the peripheral nerve. The first electrical stimulation pulse can be delivered to activate the peripheral nerve and evoke an action potential. The device can further comprise a sensor configured to measure the action potential evoked in the peripheral nerve by the first electrical stimulation pulse via a second peripheral nerve effector placed on the patient's skin, and a processor configured to adjust one or more parameters of the electrical stimulation, including but not limited to current or voltage intensity, pulse width (or pulse duration), and frequency, based on a predetermined feature of the sensed action potential, including but not limited to nerve conduction velocity. In some embodiments, the sensing peripheral nerve effector can be placed orthodromically or antidromically with respect to the stimulation adjacent to the stimulated peripheral nerve. In an additional embodiment, the system can have a single sensing effector placed in a location that can measure nerve activity of the first stimulated peripheral nerve and the second stimulated peripheral nerves, only when the two nerves are not stimulated simultaneously. For example, a single sensing effector could be place adjacent to the brachial plexus to measure stimulated nerve activity of both the radian and medial nerves, only when they are not stimulated simultaneously.

In a further embodiment, an electrical stimulation and sensing device can comprise a stimulation pulse generator configured to deliver an electrical stimulation to a patient. The electrical stimulation can comprise a first stimulation pulse delivered to a first peripheral nerve of the patient via a first peripheral nerve effector placed on the patient's skin adjacent to the first peripheral nerve and a second stimulation pulse delivered to a second peripheral nerve of the patient via a second peripheral nerve effector placed on the patient's skin adjacent to the second peripheral nerve. The first electrical stimulation pulse can be delivered to activate the first peripheral nerve and evoke a first action potential and the second electrical stimulation pulse can be delivered to activate the second peripheral nerve and evoke a second action potential. The device can further comprise a first sensor configured to measure the first action potential evoked in the first peripheral nerve by the first electrical stimulation pulse via a third peripheral nerve effector placed on the patient's skin, and a second sensor configured to measure the second action potential evoked in the second peripheral nerve by the second electrical stimulation pulse via a fourth peripheral nerve effector placed on the patient's skin, and a processor configured to adjust one or more parameters of the electrical stimulation, including but not limited to current or voltage intensity, pulse width (or pulse duration), and frequency, based on a predetermined feature of the sensed action potential. In some embodiments, the sensing peripheral nerve effectors can be placed adjacent to the stimulated peripheral nerve either orthodromically or antidromically with respect to the stimulating peripheral nerve effector.

In some embodiments, the device further comprises an additional set of sensors configured to measure action potentials of the stimulated nerve both orthodromically and antidromically with respect to the stimulating peripheral nerve effector(s).

In a further embodiment, the device includes a processor configured to adjust one or more parameters of the electrical stimulation based on one or more predominant features of nerve conduction velocity derived from the sensed action potential. The derived features can be associated with a preferential activation of specific fiber type(s).

In another embodiment, afferent or efferent fibers can be preferentially stimulated by adjusting pulse width. For example, not to be limited by theory, shorter pulse widths (e.g., less than 200 μs) can preferentially activate efferent fibers, and longer pulse widths (e.g., greater than 500 μs) can preferentially activate afferent fibers. In a further embodiment, current level can be held constant as pulse width is modified to maximize activation. In an additional embodiment, frequency can be held constant as pulse width is modified to maximize activation. In an additional further embodiment, current level and frequency can be held constant as pulse width is modified to maximize activation. In a further embodiment targeting afferent fibers, current or voltage level may be determined by finding a minimum sensory threshold for each individual or before each stimulation session. In a further embodiment targeting efferent fibers, current or voltage level may be determined by finding a muscle contraction threshold. In a further embodiment of the system, one or more additional sensing electrodes can be placed along the pathway of the target nerve being stimulated that measure conduction velocity of the stimulated nerve to assess engagement of specific fiber types; pulse width can be modified to maximize activation of a specific fiber type corresponding to the measured conduction velocity.

In some embodiments, peripheral nerve effectors can be positioned on the patient's skin such as on the medial side of the forearm as to stimulate the median cutaneous nerve but not stimulate or not substantially stimulate the median, radial, or ulnar nerves, or at least stimulate the medial cutaneous nerve preferentially. In some embodiments, the lateral cutaneous nerve and/or musculocutaneous nerve, or specific fibers thereof can be preferentially or specifically stimulated. In some embodiments, only a single type of nerve fiber is activated, while other types are not activated.

Selective activation of various nerve fiber types can be accomplished in various ways. In some embodiments, stimulation parameters such as pulse width of a biphasic square wave (shown schematically in FIG. 1) can be controlled to selectively activate specific fiber types (e.g., without activating other fiber types). For example, pulse widths of about 50-100 μs can selectively stimulate larger A-alpha fibers; pulse widths of about 150-200 μs can selectively stimulate smaller A-delta fibers; and pulse widths of about 300-400 μs can selectively stimulate even smaller C fibers.

Figure 2:
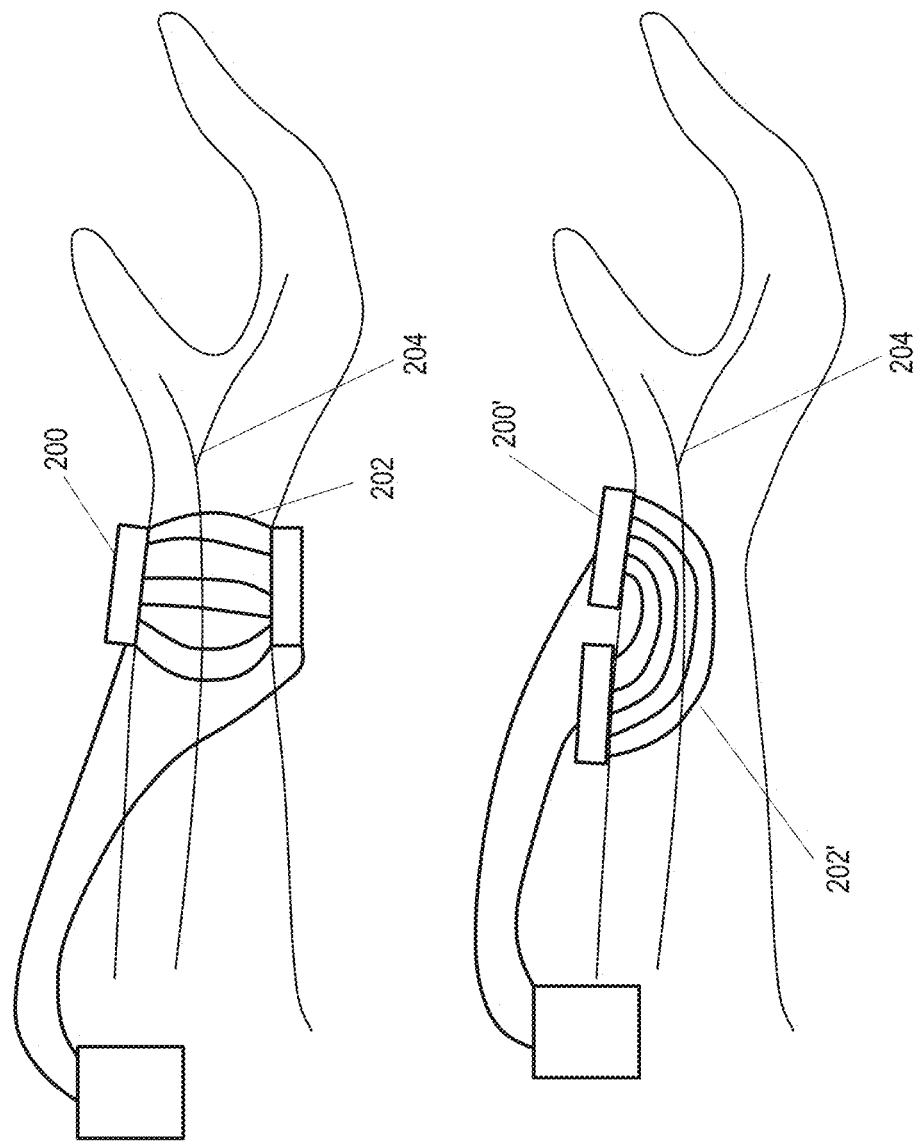
FIGS. 2A and 2B illustrate an embodiment of peripheral nerve stimulation, where the median nerve is stimulated by electrodes placed longitudinally along the nerve (FIG. 2B) versus excitation by an array of electrodes circumferentially distributed around the wrist (FIG. 2A).

In some embodiments, a device can include electrodes configured to selectively stimulate superficial nerve fibers (e.g., fibers closer to the surface of the skin) by aligning the electrodes along the length of the nerve axon. FIG. 2A previously described schematically illustrates an example on the wrist. In some embodiments, electrodes of a device can be selectively configured to selectively stimulate deep nerve fibers (e.g., fibers further away from the surface of the skin) by transversely aligning the electrodes across the limb. FIG. 2B previously described schematically shows an example on the wrist.

In some embodiments, stimulation systems and methods can be configured to increase blood flow at a target region (e.g., in the gut) to improve clearance of inflammatory biomarkers (e.g., cytokines).

In some embodiments, noninvasive neuromodulation for autonomic regulation for IBD and other diseases can be performed.

Autonomic nervous system imbalance with a dominant activation of the sympathetic nervous system and inadequate parasympathetic tone may have a key role in the pathogenesis of various immune related disorders including IBD. In some embodiments, increased local blood flow can improve cytokine (or other inflammatory marker) clearance from the GI tract. Anatomical studies have shown large amounts of sympathetic adrenergic/noradrenergic fibers innervate both into the dome region of the follicles where fibers are in direct contact with lymphoid cells and in the lamina propria where fibers are mainly associated with blood vessels. Non-invasive nerve stimulation can regulate blood flow changes and inflammatory marker clearance. In some embodiments, tibial stimulation can tap into the enteric nervous system via the pelvic nerve, modulating transmucosal fluid fluxes, local blood flow and other functions.

In some embodiments, systems and methods as disclosed herein can increase blood flow to a target region of the anatomy by at least about, about, or no more than about 5%, 10%, 15%, 20%, 25%, 30%, 40%, 50%, 60%, 70%, 80%, 90%, 100%, or more, or ranges including any of the aforementioned values.

The enteric nervous system (ENS) is a major division of the autonomic nervous system with a mesh-like system of nerves that regulates the gastrointestinal (GI) tract, which includes the splanchnic organs like stomach, small intestines, and large intestines. Splanchnic circulation, or circulation of the GI tract, is composed of gastric, small intestinal, colonic, pancreatic, hepatic, and splenic circulations, arranged in parallel with one another. The three major arteries that supply the splanchnic organs, celiac and superior and inferior mesenteric, give rise to smaller arteries that anastomose extensively. The circulation of some splanchnic organs is complicated by the existence of an intramural circulation, and redistribution of total blood flow between intramural vascular circuits may be as important as total blood flow. Numerous factors influence the splanchnic circulation, including external factors such as activity of the autonomic nervous system, the state of the cardiovascular system, and concentrations of neurohormones circulating in the blood.

Blood flow rate in vessels is governed primarily by the arterial-to-venous pressure gradient and the mechanical resistance to the flow of blood along the vessel. Small changes in the vascular smooth muscle tone can alter the diameter of the vessel. The vascular resistance is inversely related to the fourth power of the radius of the vessel, thus a small change in internal diameter will produce a large change in resistance and blood flow. For example, a small decrease in diameter of a blood vessel would produce a large increase in resistance and thus a large decrease in blood flow, and vice-versa. Blood vessels that provide the greatest changes in resistance to blood flow, like small arteries and arterioles, are densely innervated by the sympathetic nervous system.

The splanchnic organs are innervated by the autonomic nervous system, including the sympathetic and parasympathetic limbs. Activation of parasympathetic fibers modulate secretion and motility that lead to metabolic and mechanical changes that affect blood flow. Postganglionic sympathetic fibers innervate and act directly on the vascular smooth muscle, and activation leads to changes in vessel diameter, tone, and thus blood flow. Generally, stimulation of the sympathetic fibers increases vascular tone and decreases blood flow to the splanchnic organs. Acute sympathetic stimulation contract venous smooth muscle and expels a large volume of pooled blood from the splanchnic venous system and into systemic circulation. Sustained sympathetic stimulation or activity leads to a decrease in blood flow mainly in the superior mesenteric and hepatic arteries. Additionally, sympathetic stimulation causes the release of neurohormones like epinephrine and norepinephrine that also alter vascular resistance and decrease blood flow.

Insufficient blood flow within the enteric system can also lead to the further release of inflammatory cytokines, including interleukin 1, tumor necrosis factor, interleukin 6, and interleukin 8, and others. Thus, mechanisms that increase splanchnic circulation can improve symptoms associated with immune related disorders, including inflammatory bowel diseases, by reducing the release of inflammatory cytokines or other markers and/or by increasing the clearance of inflammatory cytokines or other markers in circulation via the liver, spleen, and/or kidneys.

Not to be limited by theory, stimulation of a first target nerve, such as the saphenous nerve can provide sympathetic modulation to reduce sympathetic tone and increase blood flow. Specifically, electrical stimulation tuned to excite large myelinated fibers in a target nerve, e.g., the saphenous nerve can provide somatic afferent input to the lumbar plexus, mediating the sympathetic input to the GI tract via the hypogastric nerve. Stimulation of a second target nerve, e.g., the tibial nerve can provide parasympathetic modulation of the enteric nervous system. Specifically, electrical stimulation tuned to excite large myelinated fibers in the tibial nerve provides somatic afferent input to sacral plexus, mediating parasympathetic input to the GI tract via the pelvic nerves to modulate secretion and motility that lead to metabolic and mechanical changes that increase blood flow.

In another embodiment, stimulation of a first target nerve, such as the auricular vagus nerve, can provide modulation of vagal tone and reduction of sympathetic activity to increase blood vessel dilation, modulate secretion and motility, and thus increase blood flow.

Figure 3:
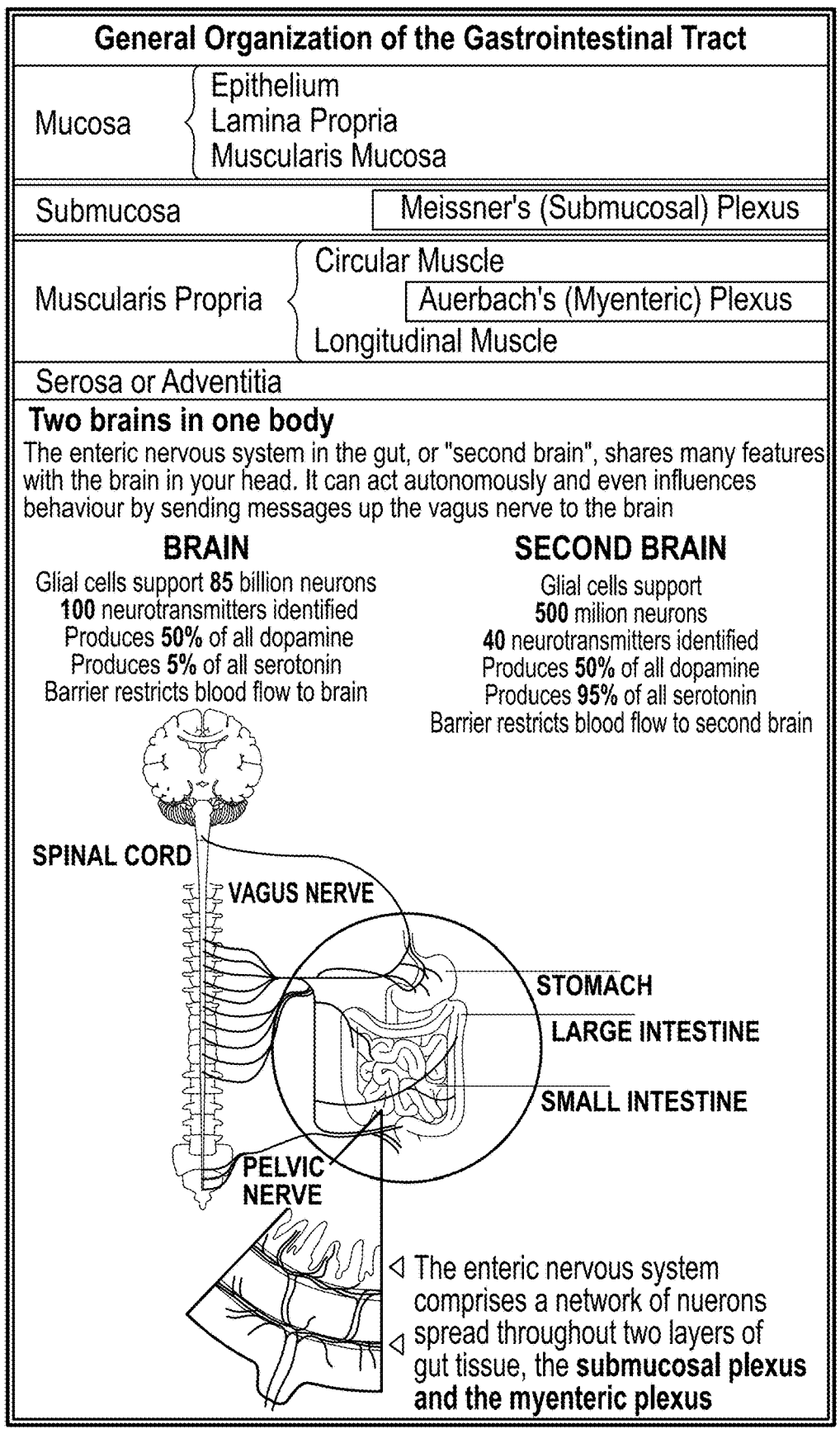
FIG. 3 schematically illustrates layers of the gastrointestinal tract, as well as certain autonomic innervation.

In another embodiment, stimulation of a first target nerve, such as the sacral parasympathetic fibers of the pelvic nerves, originating in the S2 to S4 spinal segments, can be stimulated directly by electrodes placed over the sacral region. Electrodes can be transcutaneous, percutaneous, and/or implanted. Stimulation of a second target nerve, such as the lumbothoracic sympathetic fibers originating in the T11 to L2 segments of the spinal cord, can be stimulated directly by electrodes placed over the lumbar region. FIG. 3 schematically illustrates layers of the gastrointestinal tract, as well as certain autonomic innervation.

In some embodiments, systems and methods can include monitoring skin turgor and/or electrodermal activity as a marker of inflammation and hydration status using, for example, a galvanic coupling method.

The etiology and pathogenesis of inflammatory bowel disease (IBD) has not yet been elucidated, yet many environmental factors are suspected to contribute to the development of IBD, including diet and hydration levels. Studies have shown negative correlations between total fluid consumption in a person's diet and the risk for developing IBD. Thus, preventing dehydration in people with or at risk of developing IBD can be important for preventing or alleviating symptoms by reducing the expression of inflammatory markers, such as cytokines.

Some embodiments can involve a closed-loop approach to treating IBD and other diseases that involves using a galvanic coupling method to identify changes in hydration status with immediate or near real-time feedback to the subject to encourage hydration while also administering therapy via electrical stimulation.

The system may target other nerves or dermatomes that modulate the parasympathetic and/or sympathetic nervous system, including but not limited to, the median nerve, ulnar, or radial nerve in the wrist, the lumbothoracic region, the sacral region, the stomach, and/or the foot including the bottom of the foot.

Dehydration can be assessed by various methods, including but not limited to a skin turgor assessment, which evaluates the level of skin elasticity, and galvanic skin response, which measures skin impedance by passing small amount of current between two electrodes. Some embodiments describe a system that incorporates a wearable sensor to measure body hydration levels, store this data over time, provide feedback to the wearer and/or adjust stimulation parameters to improve therapeutic benefit of the stimulation.

In one embodiment, the wearable system includes a sensor for detecting galvanic skin response, memory for storing data from the sensor, a computational unit for assessing sensor data, a feedback device, such as a display or haptic motor to display sensor output or trigger the wearer, and/or controller unit to control output of stimulation. The galvanic skin response sensor can be embedded in a device that is placed transcutaneously on the surface of the skin in locations including, but not limited to, the wrist, arm, leg, chest, or abdomen. The sensor may be disposed in an adhesive patch placed anywhere on the body, or disposed in an enclosure that houses all parts of the system. In some embodiments, the sensor may be a separate device from the stimulation and is in wireless or wired communication with the stimulator. In some embodiments, the sensor data is transmitted to an external computational device or transmitted wirelessly to a database (e.g., the cloud) for further processing.

In one embodiment, the wearable system includes a sensor for detecting skin elasticity. Skin elasticity can be measured mechanically by stretching the skin and measuring the resistive force during stretching. A device may house effector end points connected to electric motors that stretch the skin in a linear or rotational motion and measure the resistive force due to the stretching. The ratio of the amount of skin stretch to resistive force can be calculated to assess skin elasticity.

Figure 4:
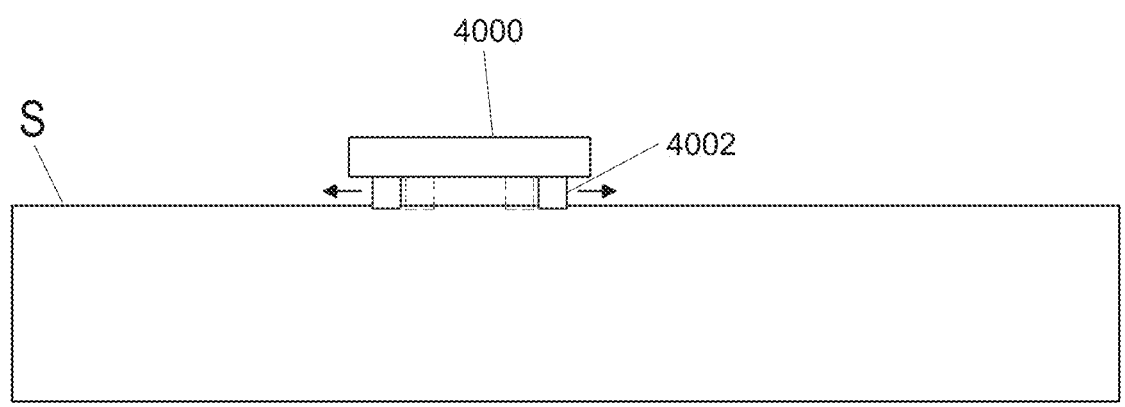
FIG. 4 schematically illustrates a skin stretch sensor that moves effectors in a linear motion to measure displacement and force (e.g., elasticity) which can be utilized to correlate to the subject's hydration status.

FIG. 4 schematically illustrates a skin stretch sensor 4000 that moves effectors 4002 in a linear motion on the skin S to measure displacement and force (e.g., elasticity) which can be utilized to correlate to the subject's hydration status.

Figure 5:
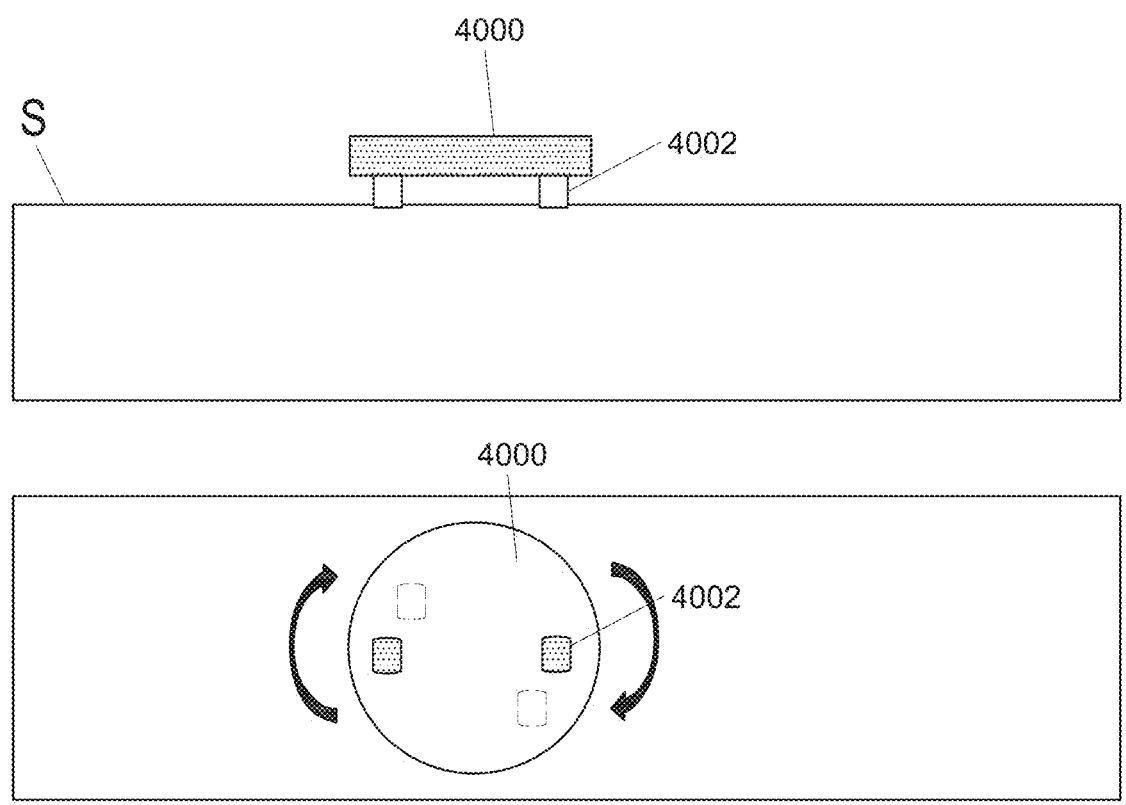
FIG. 5 schematically illustrates a skin stretch sensor that moves effectors in a rotational motion to measure displacement and force which can be utilized to correlate to the subject's hydration status.

FIG. 5 schematically illustrates a skin stretch sensor that moves effectors in a rotational motion on the skin S to measure displacement and force which can be utilized to correlate to the subject's hydration status.

Figure 6:
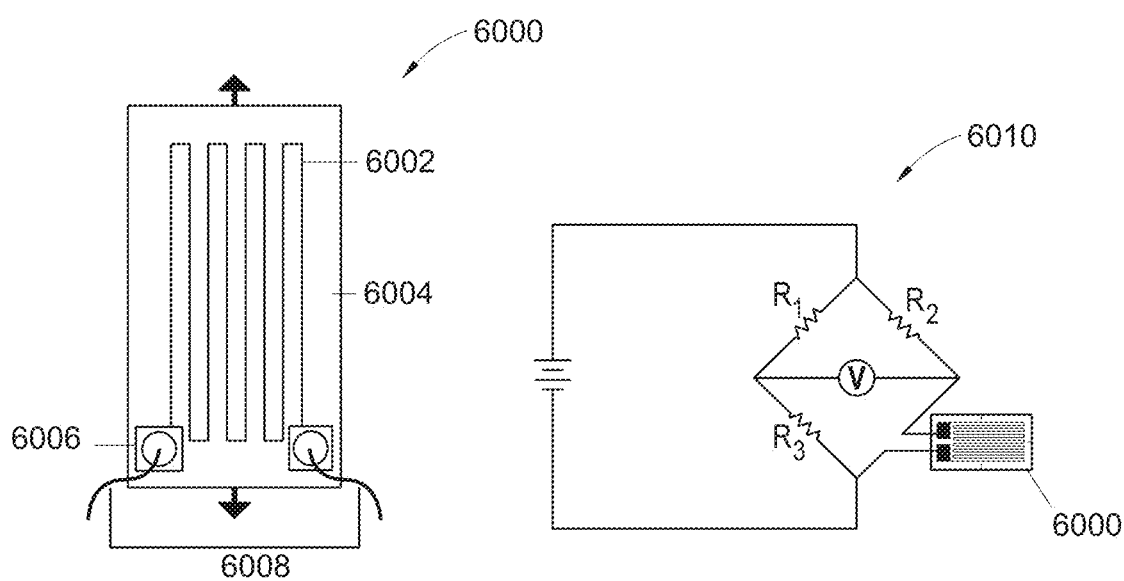
FIG. 6 schematically illustrates a strain gauge circuit that can include a metal foil. A quarter bridge circuit can be used to measure a resistance change in the gauge.

In another embodiment, the sensor for detecting skin elasticity can be an adhesive patch with strain sensors that measure strain due to skin stretch during normal or directed motions. Strain sensors measure strain of an object by measuring the change in electrical resistivity of the sensor as it is deformed, and strain is a measure of deformation representing the displacement between particles in the body relative to a reference length. Strain measurements can be stored over time to assess the state of skin elasticity and correlate the measure to the wearer's level of dehydration. FIG. 6 schematically illustrates a strain gauge circuit 6000 that can include an etched metal foil 6002, backing material 6004, solder terminals 6006, and connecting wires (leads) 6008. Arrows illustrate schematically a direction of strain. A quarter bridge circuit 6010 can be used to measure a resistance change in the strain gauge 6000.

In some embodiments, not to be limited by theory, alternating bursting stimulation on two or more different nerves, e.g., the medial, radial, and/or ulnar nerves can prevent or reduce an inflammatory response by having a synergistic effect that increases input to stellate ganglion via the brachial plexus to inhibit sympathetic activity or modulate vagal tone via the carotid sinus nerve.

In some embodiments, a system can include a plurality of stimulators that communicate with each other wirelessly and provided a synchronized continuous or patterned stimulation, and/or synchronize the timing of different stimulations. In some embodiments, multiple stimulators may be in electrical connection with multiple electrode pairs to stimulate multiple nerves simultaneously. Each stimulator in the system can communicate with each other via a wired or wireless connection. Multiple stimulators can provide synchronized stimulation to the multiple nerves. Stimulation may be, for example, burst, offset, or alternating between the multiple nerves. In some embodiments, a stimulation system with a plurality of stimulator housings that can include or be operably connected to a patch having electrodes and a skin-contacting surface. Each individual stimulator can be placed, for example, transcutaneously just below the knee and/or just above the ankle as illustrated. The stimulators can be placed sufficient to stimulate the saphenous and/or tibial nerves. The stimulators can be placed in some cases between the knee and the ankle, such as in the proximal calf (such as within the most 25% proximal section of the calf, or between the 25% and 50% most proximal section of the calf), distal calf (such as the most 25% distal section of the calf or between the 25% and 50% most distal section of the calf), or combinations thereof. The stimulators can be physically discrete for each other, or combined into a single housing such as a calf band or other form factor as described elsewhere herein.

Figure 6A:
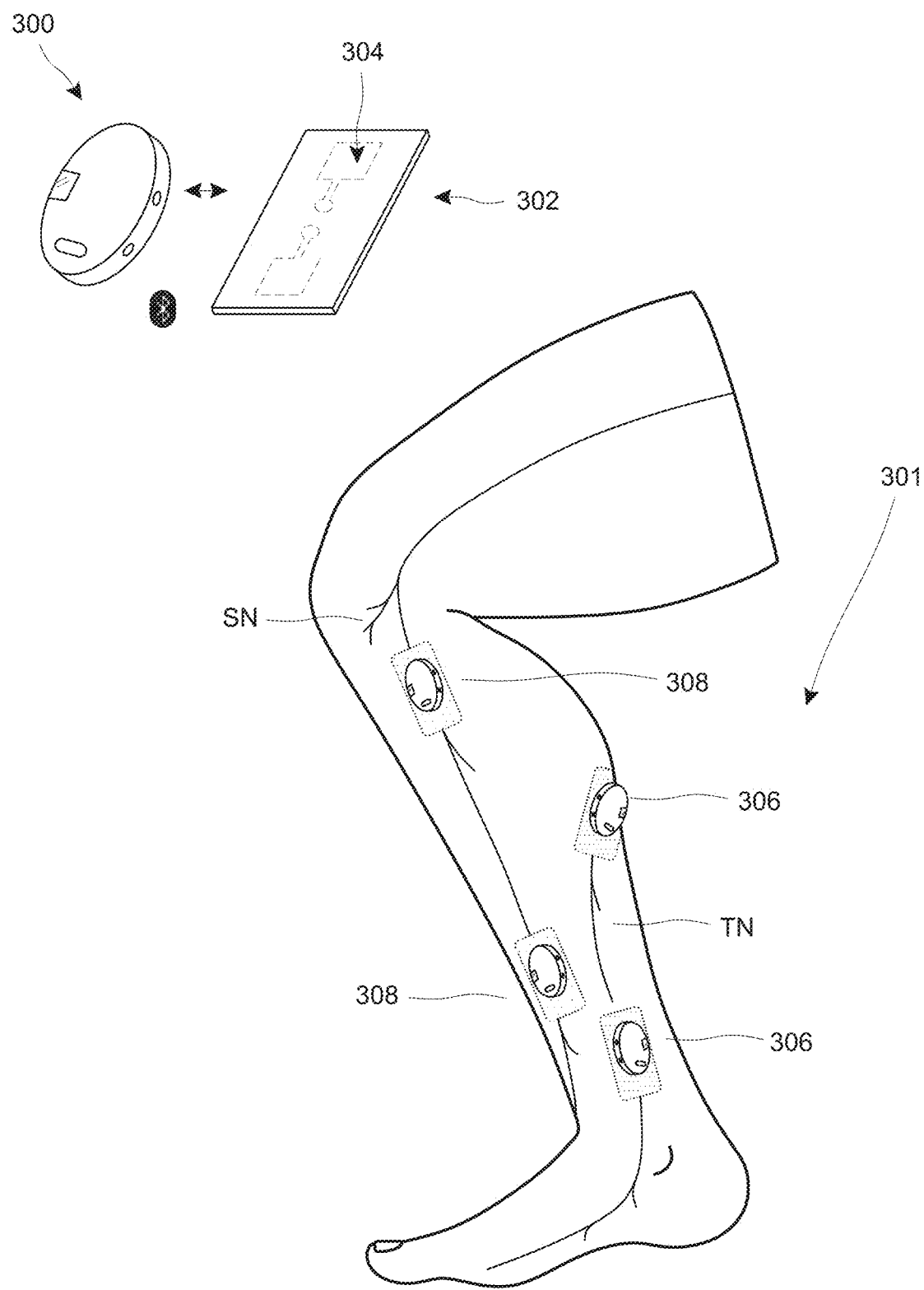
FIG. 6A schematically illustrates a stimulation system with a plurality of stimulator housings that can include or be operably connected to a patch having electrodes and a skin contacting surface.
Figure 6D:
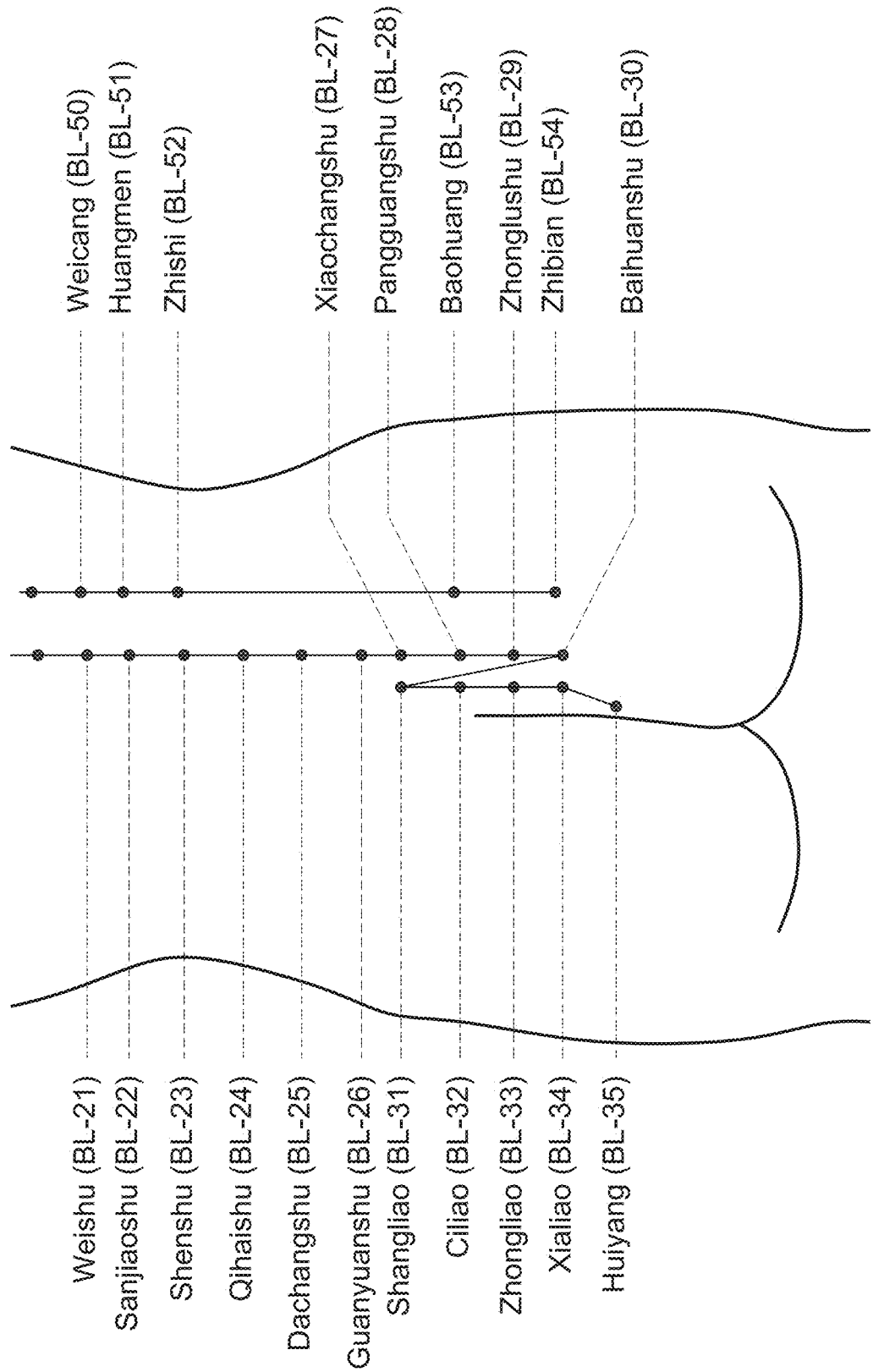
FIGS. 6D-6H illustrate non-limiting examples of potential acupuncture points that can be stimulated, in accordance with some embodiments of the invention.
Figure 6E:
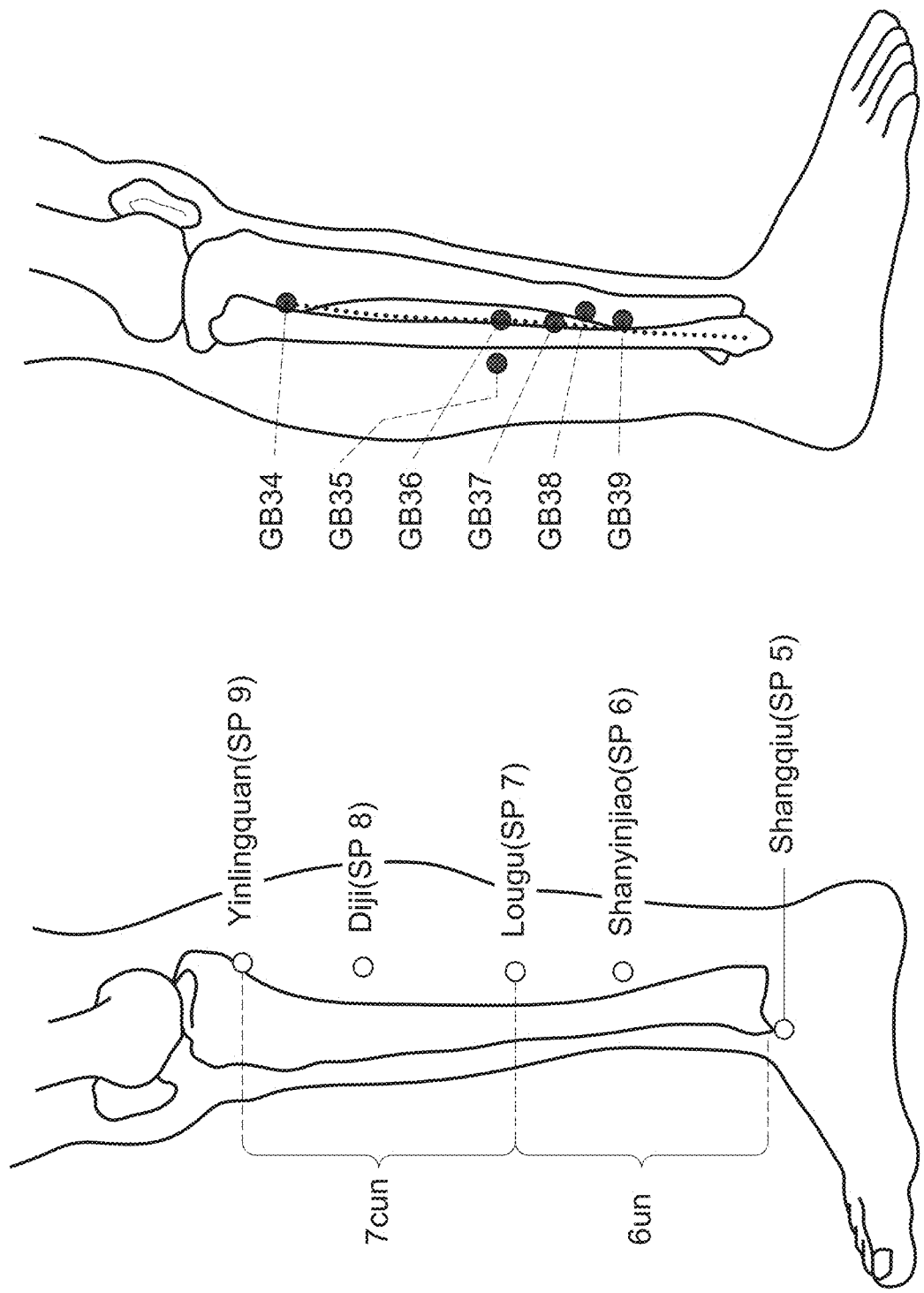
Figure 6F:
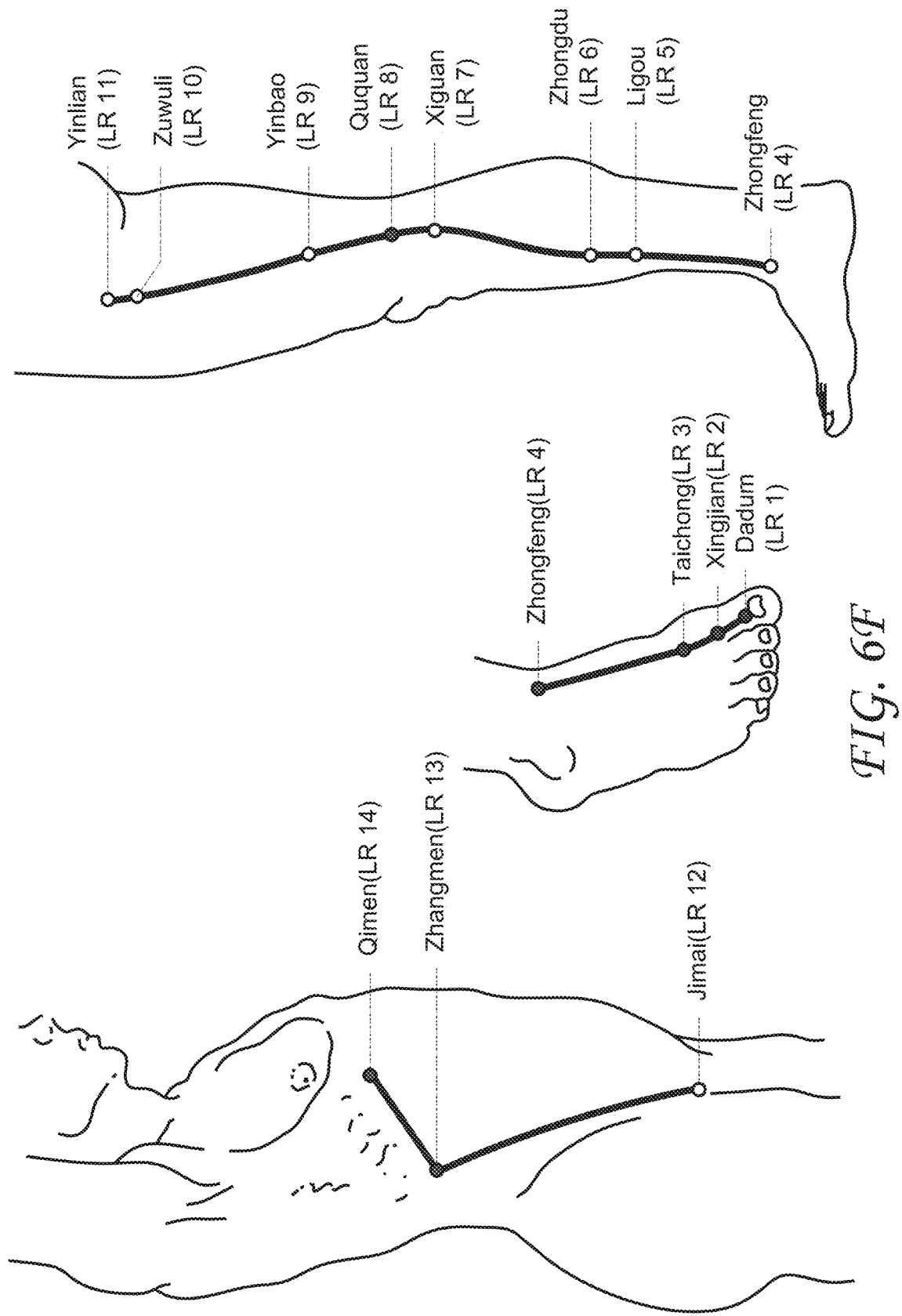
Figure 6G:
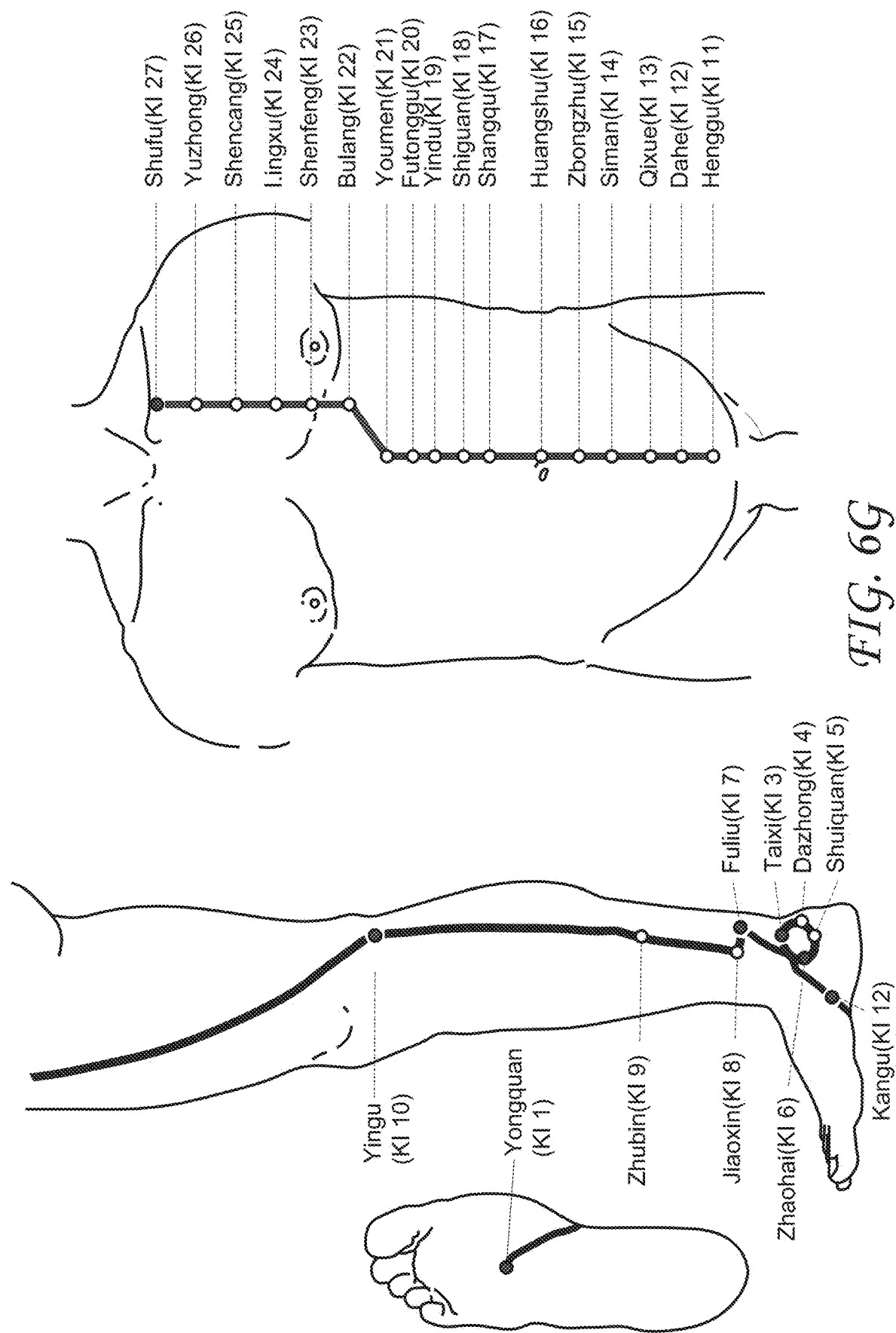
Figure 6H:
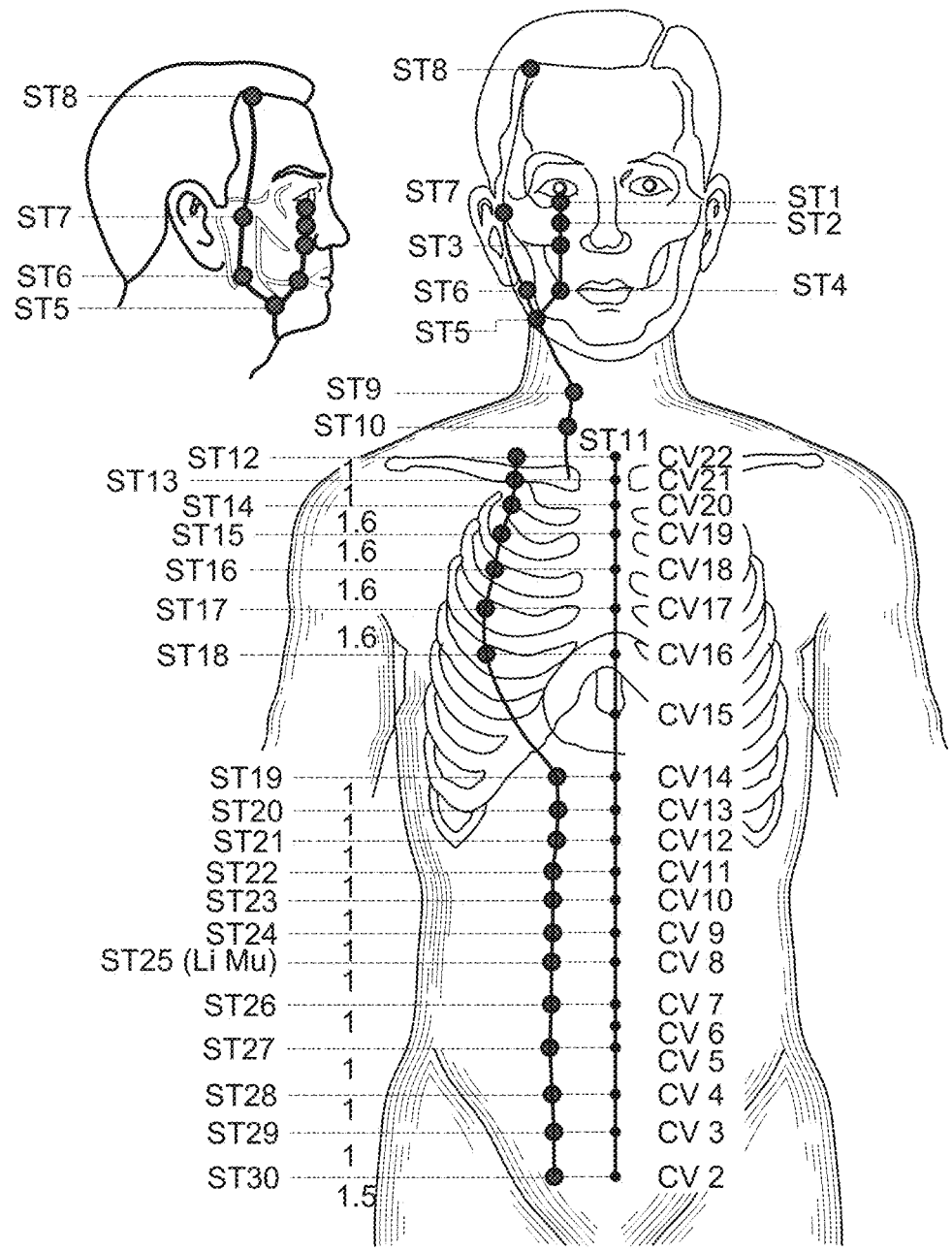
Figure 61:
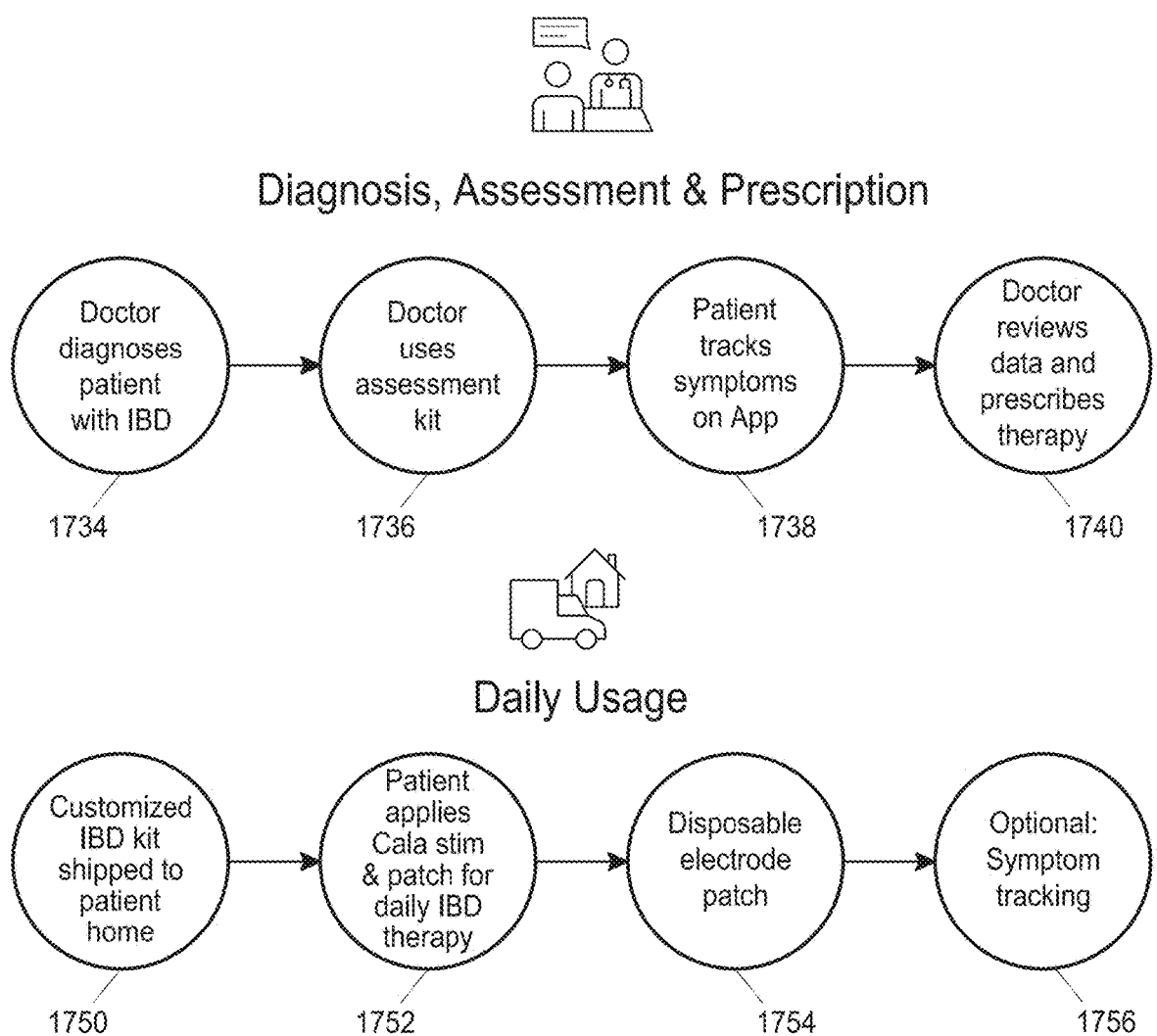

In some embodiments, the electrodes, constructed from an adhesive hydrogel, are disposed in the housing of the device allowing the device to adhere to the wearer's skin. In other embodiment, the electrodes are dry or non-adhesive and are disposed in the device with a strap to securely connect to electrodes to a limb, such as on the wrist or ankle. In some embodiments, a system can include a plurality of stimulators that communicate with each other wirelessly and provided a synchronized continuous or patterned stimulation. In some embodiments, multiple stimulators may be in electrical connection with multiple electrode pairs to stimulate multiple nerves simultaneously. Each stimulator in the system can communicate with each other via a wired or wireless connection. Multiple stimulators can provide synchronized stimulation to the multiple nerves. Stimulation may be, for example, burst, offset, or alternating between the multiple nerves. FIG. 6A schematically illustrates a stimulation system 6001 with a plurality of stimulator housings 6000 that can include or be operably connected to a patch 6002 having electrodes 6004 and a skin contacting surface. Each individual stimulator 6006 (shown positioned to stimulate the tibial nerve TN) or stimulator 6008 (shown positioned to stimulate the saphenous nerve SN) can be placed, for example, transcutaneously just below the knee and/or just above the ankle as illustrated. The stimulators can be placed sufficient to stimulate the saphenous and/or tibial nerves. The stimulators can be placed in some cases between the knee and the ankle, such as in the proximal calf (such as within the most 25% proximal section of the calf, or between the 25% and 50% most proximal section of the calf), distal calf (such as the most 25% distal section of the calf or between the 25% and 50% most distal section of the calf), or combinations thereof. The stimulators can be physically discrete for each other, or combined into a single housing such as a calf band, wrist band, in-ear electrode or other form factor as described elsewhere herein.

In some embodiments, dry electrodes can be utilized, such as dry electrodes that include a conductive backing layer (e.g., a metal foil material, such as disposed on a flexible polymer substrate) and a skin contact layer disposed on the conductive backing layer, that can include for example a polymer, plastic, or rubber material, and a conductive filler material (e.g., powder, fine particulate material, metal, carbon, mixtures thereof, or porous material treated with a conductive coating) dispersed substantially evenly throughout the silicone, plastic, or rubber material. In some embodiments, the skin contact layer has a skin facing surface that is not coated with a hydrogel or liquid. In some embodiments, the dry electrodes can be as disclosed in PCT App. No. PCT/US2017/040920, filed on Jul. 6, 2017, hereby incorporated by reference in its entirety.

In some embodiments if the electrodes are sticky, as shown in the embodiment of FIGS. 6B and 6C, a device in the form of a bandage can be made, which circumferentially or non-circumferentially envelop a portion of a body part, such as an extremity. The strip can be any shape, including an annular, square, rectangular, triangular, or other shape. In some cases, the electronics can be located inside a removable housing that can be removably attached at site from the entire device when the disposable is thrown away. FIG. 6B is a bottom view, while FIG. 6C is a top view of the device.

In some embodiments, median, radial, and/or ulnar stimulation can be combined for a synergistic effect at the brachial plexus. The median, radial, and ulnar nerves innervate different levels of the spinal cord at the brachial plexus, with pathways that proceed to different target locations and organs. Some embodiments can provide timed stimulation, either simultaneously or with a delay, to the median, radial, and/or ulnar nerves to control targeting within the brachial plexus to provide a synergistic effect of neural activation at the brachial plexus, which leads to the stellate ganglia and the sympathetic chain. This synergistic effect can provide an advantage of greater therapeutic benefit with less discomfort and less current (e.g., less power for longer battery life). Timing of the stimulation may be simultaneous, or with a delay to account for differences in conduction velocities for the different nerves such that the signals reach the brachial plexus at the same time. Not to be limited by theory, but simultaneous or near simultaneous activation of the brachial plexus can enhance stimulation through the pathway to the stellate ganglia, and increase the effect (e.g., inhibition) of the sympathetic nervous system. For example, the average conduction velocities of sensory nerves of radial, median, and ulnar nerves are about 51 m/s, 60 m/s, and 63 m/s respectively. Based on variation in nerve length from the wrist to the brachial plexus from 1st percentile female to 99th percentile male, this would require a delay in stimulation between the median and radial nerves of about 1.3 to about 1.7 milliseconds, between median and ulnar of about 0.3 and about 0.4 ms, and between radial and ulnar of about 1.6 ms and about 2.1 ms. In some embodiments the delay in stimulation between a first nerve and a second nerve can be between about 0.3 ms and about 1.7 ms, or between about 0.2 ms and about 2.0 ms, between about 1.2 ms and about 2.1 ms, or between about 1 ms and about 2 ms. Lower threshold stimulation on the median, radial, and/or ulnar nerves in combination can advantageously require lower threshold stimulation on the individual nerves with a resultant synergistic effect at the brachial plexus. In some embodiments, a system could include a nerve conduction velocity measurement by applying a stimulation source on a distal portion of the nerve(s) and a measurement electrode on a proximal portion of the nerve(s) to measure an individual's nerve conduction velocities and modify the timed delay based on the individualized measurements.

In some embodiments, a system could include an electrode configuration to stimulate nerves (e.g., radial, median, and/or ulnar) in an alternating pattern that could be rhythmic or pseudorandom. For rhythmic alternating patterns, the alternating frequency can be in a range from 1-100 Hz, which has been shown improve efficiency of therapy by promoting plasticity of corticospinal circuits. In some embodiments, a device embodiment could include an electrode configuration to alternate stimulation of nerves (e.g., radial, median, and/or ulnar) and adjust stimulation parameters (e.g., stimulation frequency, alternating frequency, duration of stimulation, stimulation time of day) based on an assessment of autonomic balance, for example, by measuring heart rate variability (HRV) and analyzing sympathovagal balance as a the ratio of absolute low frequency (LF) to absolute high frequency (HF) power, or LF/HF of measured HRV as noted elsewhere herein.

Sympathetic and parasympathetic activity can be measured through several methods, including microneurography (MSNA), catecholamine tests, heart rate, HRV, or galvanic skin response. HRV can provide a quick and effective approximation of autonomic activity in the body. HRV can be determined by analyzing the time intervals between heartbeats, also known as RR intervals. Heart rate can be accurately captured, for example, through recording devices such as chest straps or finger sensors. The differences between successive RR intervals can provide a picture of one's heart health and autonomic activity. Generally speaking, healthier hearts have more variability between successive RR intervals. This interbeat data can also be used to denote an individual's sympathetic and parasympathetic activity levels. Through frequency-domain analysis, heartbeat frequencies can be separated into distinct bands. High-frequency signals (~0.15-0.4 Hz) can almost exclusively reflect parasympathetic activity, and low-frequency signals (~0.04-0.15 Hz) can represent a mixture of sympathetic and parasympathetic activity. Therefore, taking the ratio of high frequency (HF) to low frequency (LF) signals can yield an approximation of one's sympathetic tone. In some embodiments, HRV can be analyzed, for example, under time domain, geometric domain methods in addition to frequency domain methods. In some embodiments, increased heart rate variability can signify increased parasympathetic response and/or decreased sympathetic response. Decreased heart rate variability can signify decreased parasympathetic response and/or increased sympathetic response. In some embodiments, a system can sense an increase or decrease in HRV of about or more than about 5%, 10%, 15%, 20%, 25%, 30%, 35%, 40%, 45%, 50%, 75%, 100%, or more over a baseline value (or target desired HRV value) and institute a change in one, two, or more stimulation modality parameters accordingly. In some embodiments, the one, two, or more stimulation modalities can be configured to modulate, such as increase or decrease stimulation to one or more nerves (e.g., peripheral nerves) associated with the sympathetic and/or parasympathetic nervous system, and a response to therapy can be confirmed by sensing an increase or decrease in parasympathetic or sympathetic tone, including but not limited to increase or decrease in HRV, changes in high frequency content of HRV, and changes in the ratio of high frequency and low frequency content of HRV. In some embodiments, balance of parasympathetic and sympathetic activity of the inflammatory response reflex loop can be assessed with frequency analysis of heart rate variability measured with pulsed plethysmography with an LED light source and optical sensor disposed in the device that measures fluctuations in light level due to blood flow that target one of the major blood vessels around the knee, which could include one or more of the following, femoral, popliteal, tibial, posterior tibial, anterior tibial, and/or descending genicular arteries or veins, or vessels around the wrist, or in the arm or neck or ear in other embodiments. In some embodiments, heart rate could be measured using accelerometer-based sensors or with electrical-based sensors, similar to single or multiple-lead ECG monitors.

A large source of error in optical measurements of heart rate is motion artifacts due to relative motion between the optical sensor and the blood vessel being measured. In some embodiments, the optical heart rate sensor has an adhesive on the side of housing that contacts the wearer's skin to reduce relative motion between the sensor and the target blood vessel. In some embodiments, one, two, or more additional sensors are disposed in the device, including electrical sensors in contact with the wearer's skin to measure cardiac activity or pressure sensors to measure changes in blood vessels, to be used in combination with an optical sensor to improve the fidelity of heart rate measurement. In some embodiments, the system and device have memory and a processor to extract RR intervals from sensor data, calculate variability of RR intervals, transform data into frequency domain, and calculate high frequency signals, low frequency signals, and the ration of the high frequency and low frequency signals. In some embodiments, the heart rate sensor can store collected data for specified time periods to gather adequate data for heart rate variability calculation. Specified time period can range in some cases from 1-60 seconds, and may extend to 10 minutes or more.

In some embodiments, electrodermal activity, also known as galvanic skin response or skin conductance response, for example, can be measured using sensors, such as electrodes. Galvanic skin response is the change of the electrical resistance of the skin caused by emotional stress, and measurable with, e.g., a sensitive galvanometer. Not to be limited by theory, skin resistance varies with the state of sweat glands in the skin. Sweating is controlled by the sympathetic nervous system, and skin conductance can be an indication of psychological or physiological arousal. If the sympathetic nervous system is highly aroused, then sweat gland activity also increases, which in turn increases skin conductance. In this way, skin conductance can be a measure of emotional and sympathetic responses, which can be measured, and the feedback data can be sent to the controller, which will in turn modulate stimulation to, for example, decrease sympathetic nervous system activity. Other nonlimiting parameters associated with sympathetic and/or parasympathetic nervous system activity that can be sensed include, for example, sweating during particular times of the day and/or night, sleep states as detected, for example, by an EEG headband (to determine when sympathetic and/or parasympathetic activity is particularly high or low, and potentially correlating a sleep state such as stage 1, 2, 3, 4, or REM with nocturia), and/or motion. In some embodiments, a diagnostic and/or combination diagnostic/stimulation device can be configured to measure a person's heart rate and galvanic skin response for improved estimation of the person's autonomic activity. In some embodiments, a wearable device, such as a wrist-worn device can include both electrodermal activity (EDA) sensors and optical heart rate sensors. This combination of data can in some embodiments advantageously and synergistically provide improved estimation of sympathetic and parasympathetic activity than a single measure alone. In some embodiments, the system can include multiple sensors to measure electrodermal activity in conjunction with heart rate and HRV. Data from the multiple sensors can be analyzed by a hardware or software processor and combined to provide a more accurate estimation of sympathetic and/or parasympathetic activity. In some embodiments, the EDA and HR sensors can be disposed in a wrist-worn device that communicates via a wired or wireless connection to the stimulator or to send data to a centralized remote server (e.g., the cloud). Stimulation parameters, nerve target locations (e.g., tibial and/or saphenous nerves for example) or dosing regimen (e.g., duration or frequency of stimulation sessions) could be adjusted based on estimations of sympathetic and/or parasympathetic activity. Adjustments could be made in real-time, or in subsequent stimulation sessions. In some embodiments, stimulation frequency can be adjusted to either increase or decrease autonomic activity modulated by a single specific nerve, or multiple nerves. For example, in some embodiments, relatively low frequency stimulation of a target nerve (e.g., below a threshold value, e.g., about 5 Hz) can potentially inhibit the nerve and thus decreases sympathetic activity, while higher frequency stimulation (e.g., above a threshold value, e.g., about 5 Hz) can potentially excite the nerve and thus increases sympathetic activity. The same effect can occur with the same or other target nerves to regulate parasympathetic activity. In other words, in some embodiments, relatively low frequency stimulation of the target nerve (e.g., below a threshold value, e.g., about 5 Hz) can potentially inhibit the nerve and thus decreases parasympathetic activity, while higher frequency stimulation (e.g., above a threshold value, e.g., about 5 Hz) can potentially excite the nerve and thus increases parasympathetic activity. Not to be limited by theory, depending on the stimulation parameters for example, in some cases stimulating the target nerve can increase or decrease either sympathetic activity, parasympathetic activity, or both. In some embodiments, stimulation of the saphenous nerve can affect sympathetic activity, and stimulation of the tibial nerve can affect parasympathetic activity.

In some embodiments, any form of stimulation as disclosed herein can be utilized to apply stimulation to one, two, or more acupuncture points. In some embodiments, the acupuncture points to be stimulated could include any one, two, three, four, five, six, seven, eight, nine, ten, or any other number of the following: BL18 (Ganshu), BL23 (Shenshu), BL27 (Xiaochangshu); BL28 (Pangguangshu); BL32 (Ciliao); BL33 (Zhongliao); BL53 (Baohuang); CV2 (Qugu); CV3 (Zhongji); CV4 (Guanyuan); CV5 (Shinen); CV6 (Qihai); GB34 (Yanglingquan); KI7 (Fuliu); KI10 (Yingu); LR1 (Dadun); LR2 (Xingjian); LR8 (Quan); N-BW-38 (Xiajiaoshu); SP6 (Sanyinjiao); SP9 (Yinlingquan); and/or ST28 (Shuidao). In some embodiments, the points to be stimulated include BL18, BL23, BL28, and CV2. In some embodiments, the points to be stimulated include ST28, SP6, BL23, BL28, BL32, BL33, BL53, CV3, and N-BW-38. In some embodiments, the points to be stimulated include SP6, BL23, BL27, BL28, BL33, and CV4. In some embodiments, the points to be stimulated include SP9, LR1, LR2, CV4, and CV6. In some embodiments, the points to be stimulated include SP6, SP9, BL23, CV3, and CV6. In some embodiments, the points to be stimulated include SP9 and GB34. In some embodiments, the points to be stimulated include SP9, KI7, KI10, and LR8. In some embodiments, the point to be stimulated is either CV5 alone or BL39 alone, or a combination thereof. Other permutations of stimulation points are also possible, depending on the desired clinical result. FIGS. 6D-6H illustrate non-limiting examples of potential acupuncture points that can be stimulated, in accordance with some embodiments of the invention.

The system may run on a selection of pre-specified programs that vary stimulation parameters and target one or more nerves individually or in combination to improve symptoms of inflammatory bowel disease or another disease in a specific patient.

Alternatively, the system may use closed loop feedback or statistical analyses or machine learning techniques that utilize a number of parameters including: the subject's symptomatic history, including voiding events, or manually entered bowel event indicated on board the device or a secondary device; direct detection of sympathetic and parasympathetic tone in the GI tract or general circuitry, including HRV and galvanic skin response; previous usage of device, e.g., purely sympathetic excitation may be enhanced by brief periods of parasympathetic balance; medical history; medication usage; activity or steps.

Some embodiments of a system could centrally store data from a plurality of sensors worn by multiple wearers on a remote server system (e.g., the cloud), along with other relevant demographic data about each wearer, including age, weight, height, gender, ethnicity, etc. Data collected from multiple wearers can be analyzed using standard statistical analysis, machine learning, deep learning, or big data techniques, such as a logistic regression or Naive Bayes classifier (or other classifiers), to improve prediction of inflammation by determining correlations between biological measures and other recorded symptom events and inflammation events. These correlations can be used to set parameters of the stimulation waveform applied by the stimulation device, determine best time to apply stimulation therapy, and/or adapt the stimulation waveform applied by the therapy unit in real time.

In some embodiments, one, two, or more sensors can be housed in the device to collect, store, and analyze biological measures about the wearer including, but not limited to, motion (e.g., accelerometers, gyroscopes, magnetometer, bend sensors), ground reaction force or foot pressure (e.g., force sensors or pressure insoles), muscle activity (e.g., EMG), cardiovascular measures (e.g., heart rate, heart rate variability (HRV), photoplethysmography (PPG), or ventricular and/or atrial dyssynchrony using electrodes to measure ECG and/or heart rhythm abnormalities), skin conductance (e.g., skin conductance response, galvanic skin response), respiratory rate, skin temperature, pupil diameter, and sleep state (e.g., awake, light sleep, deep sleep, REM).

Using standard statistical analysis, machine learning, deep learning, or big data techniques, such as a logistical regression or a Naïve Bayesian classifier, these biological measures can be analyzed to assess the wearer's activity state, such as sedentary versus active, level of stress and the like, which in turn, can serve as a predictor of inflammation and/or GI symptoms.

FIG. 6 illustrates an embodiment of a system for treating inflammatory bowel diseases using a wearable therapy device. As described above, the therapy device may include two parts, a band 500 and a therapy unit 502. A base station 600, which may replace the charger in the kit described above, can be used to both charge the therapy device and to receive and transmit data to the therapy device and to the cloud 602. Communication between the base station 600 and the therapy device can be wireless, such as through Bluetooth and/or Wi-Fi, and communication between the base station 600 and the cloud 602 can be through a cellular network, using a 3G or 4G connection, or through a wired connection to the internet, using DSL or cable or Ethernet, for example. A physician or other user can view and/or retrieve data stored on the cloud 602 using an online portal or a physician web portal 604. In addition, the physician can prescribe and/or modify a treatment regimen on the therapy unit 502 through the cloud 602 and base station 600 using the web portal 604.

In some embodiments, the base station 600 is used to receive and transmit relatively large amounts of data that may require a high bandwidth, such as the transmission of raw data from the therapy device, which may be about or at least about 10 to 100 Mb/day, or about or at least about 10, 20, 30, 40, or 50 Mb/day. In some embodiments, the data may be stored in memory in the base station 600 and transmitted at another interval, such as weekly or twice weekly, with a scaling up of the bandwidth of transmission. The high bandwidth transmission of the raw data can occur daily while the therapy device is being charged, such as at night during a regular charging period. In some embodiments, the raw data can be processed by the cloud and/or the physician into processed data and sent back to the therapy device.

In some embodiments, the system may optionally include a portable computing device 606, such as a smart phone or tablet, to provide a secondary display and user interface for the patient and to run applications to more easily control the therapy device and view the raw and processed data. The portable computing device can be used to make patient or physician adjustments to the therapy device, such as adjusting the stimulation parameters and dosing, and can receive device state data from the therapy device, which includes data relating to the device, such as when the device was used, errors, therapy parameters such as amplitude and when they were set and delivered. In some embodiments, the portable computing device 606 can receive processed data from the cloud 602 through a cellular network and/or through an internet connection using Wi-Fi, for example.

Figure 7L:
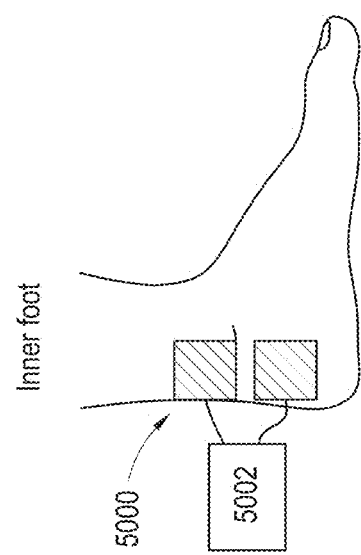
FIGS. 7A and 7B illustrate embodiments of electrode alignments for selective activation of nerve fibers.
Figure 60:
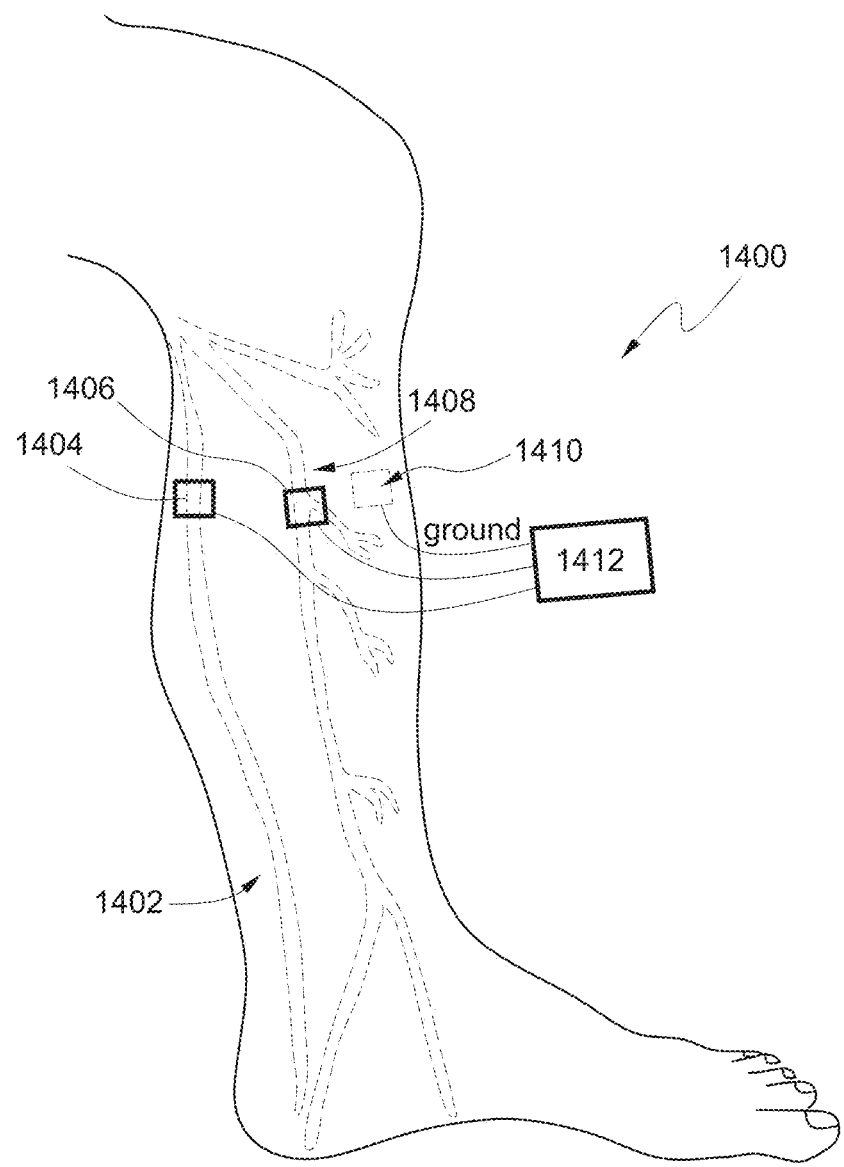

FIG. 7 illustrates the various components that can be included in a therapy unit 700, band 702, and base station 704. These components are described in detail above and also below as non-limiting embodiments. For example, the therapy unit 700 includes one or more indicators 706, which can be LEDs, and a user interface 708, which can be push buttons, for example. The therapy unit 700 can also have a stimulator 710 with stimulation electronics and may include the capability to measure current and voltage. The therapy unit 700 can also have a battery 712, which may be rechargeable and can be recharged using charging circuitry 714, which may be inductive. The therapy unit 710 may further include a processor 716 and memory 718 to store and execute programs and instructions to accomplish the functions described herein. The therapy unit 710 may also include sensors 720, such as blood pressure sensors, and a communications module 722, which may be wireless and can communicate with the base station 704 and/or a secondary display/computing device.

The band 702 can have electrodes 724 and may also include memory to store identification information or may include some other form of identifier 726 as described herein.

The base station 704 can include charging circuitry 728, which may also be inductive and can transmit power to the complementary charging circuitry 714 on the therapy unit 700. The base station 704 can also have a processor and memory for storing and executing instructions and programs. The base station 704 can further include a communication module 732, which may be cellular, to communicate with the cloud, and another communication module 734, which may be wireless and used to communicate with the therapy unit.

In some embodiments, the device can be a biological sensor, such as a heart rate or respiratory monitor worn on the body, which could include an integrated nerve stimulator. In some embodiments, the nerve stimulator and sensor device can be separate devices that communicate wirelessly. In some embodiments, the device can measure a biological measurement over the course of minutes, hours, days, weeks and/or months to determine whether the patient's condition is increasing, decreasing, or staying the same. In some embodiments, the measurements are time averaged over a window, which can be days, weeks, or months. In some embodiments, a sensor, such as a motion sensor, IMU, or GPS, can be used to detect patient activity, which can affect other measurements. In some embodiments, the sensor can be an electrode that measures galvanic skin response, which can be correlated to stress, a known trigger for inflammatory bowel disease, inflammation, or symptoms caused by other inflammatory conditions. In some embodiments, measurements are collected at the same time each day with the same conditions to improve measurement consistency and to reduce variability. In some embodiments, the stimulator is applied to one wrist or arm or ear to stimulate one peripheral nerve in the arm, such as the median nerve or ABVN, or specific nerve location, such as an acu-pressure point or meridians.

Figure 6J:
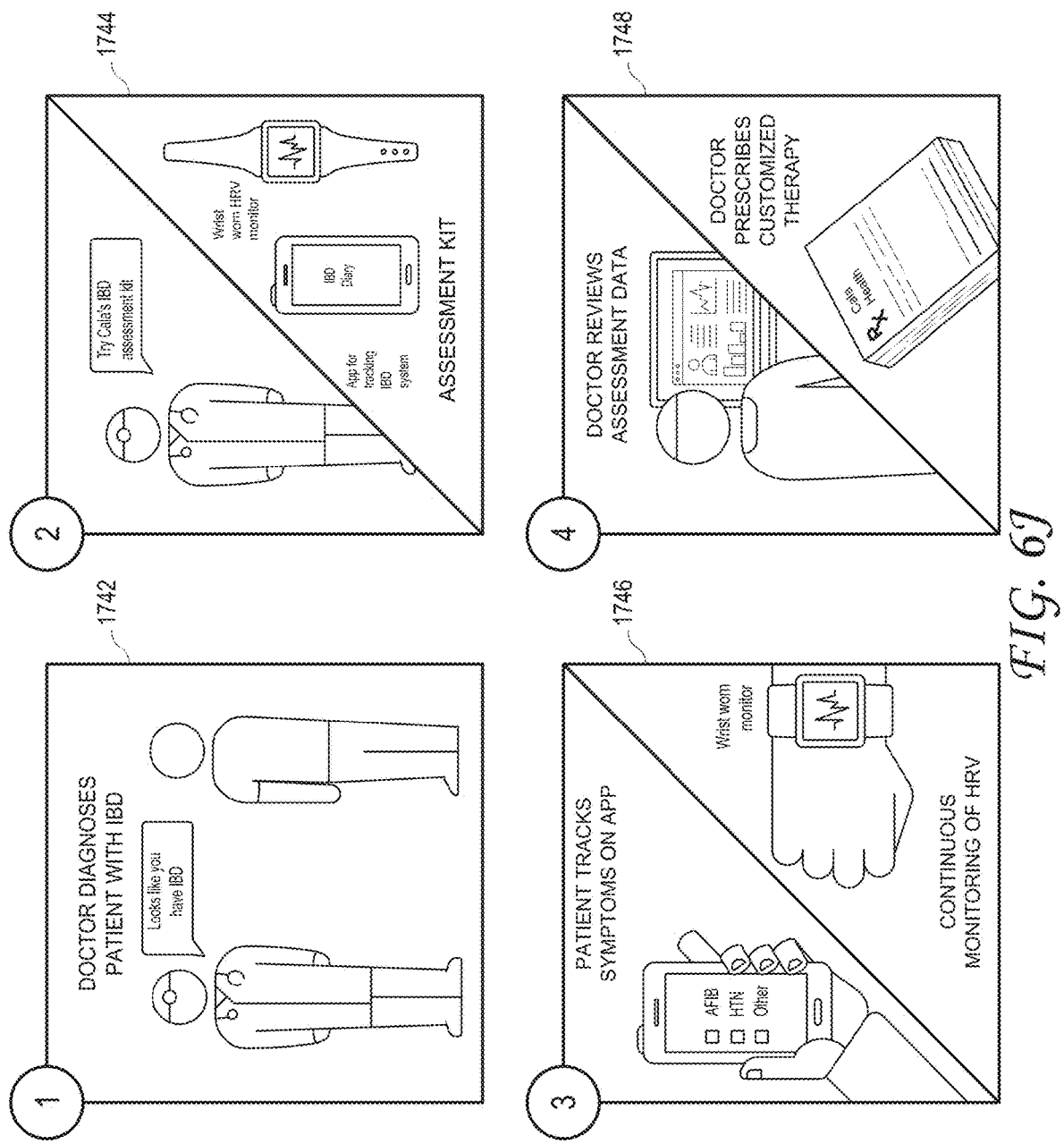
Figure 6K:
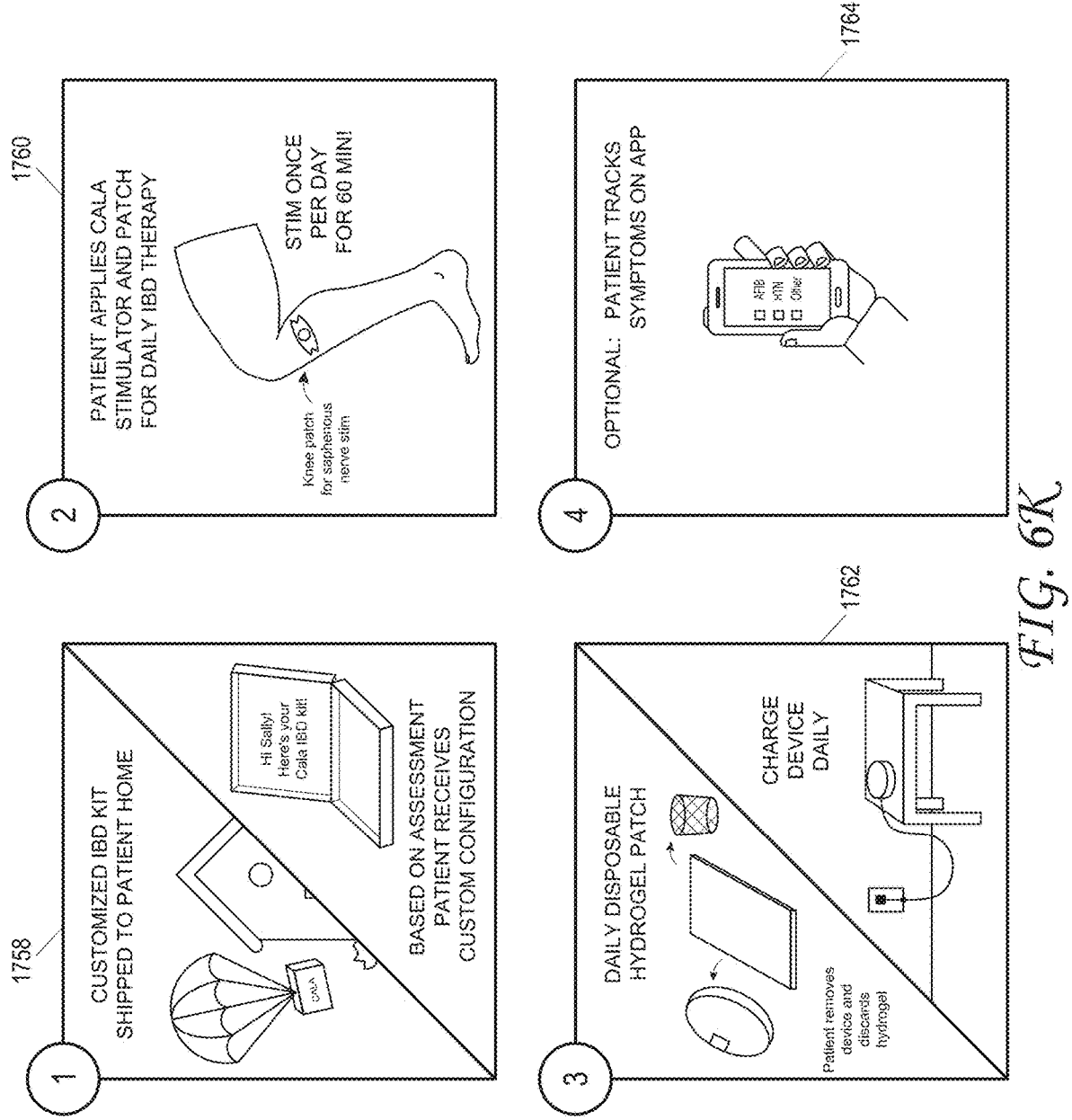

The number of episodes of symptoms such as inflammatory bowel disease could be detected in various ways to control the stimulation applied by system and devices. In some embodiments, the patient can enter events related to symptoms of inflammatory bowel disease, including but not limited to fecal voiding events, urgency events, incontinence events, or abdominal pain on a mobile device. In some embodiments, location services on the device, such as GPS, can detect when the person has entered a building or bathroom. Information regarding bowel voiding can be combined in some embodiments with an understanding of the amount of food and fluids a person has consumed in order to better apply a desired amount of treatment. For example, in days where more food and drink were consumed by an individual, more bowel voiding would be expected. FIGS. 6I-6K schematically illustrates flow charts incorporating a stimulation protocol, according to some embodiments of the invention, including a sample diagnosis, prescription, and usage workflow. A physician can diagnose a patient with a disorder, such as IBD or another disease (box

1734, 1742) as disclosed elsewhere herein for example. The physician can utilize an assessment kit (box 1736, 1744); and the patient can track symptoms on a software app or other log (box 1738, 1746), as well as via sensors, e.g., HRV or others as disclosed herein. The physician can then review the data and prescribe an appropriate therapy (box 1740, 1748). A customized IBD kit can then be provided to the patient (box 1750, 1758), who can apply the neuromodulation device (box 1752, 1760), which can be in the form on a disposable electrode patch (box 1754, 1762) in some cases. The times, amounts, and types of food ingested by a patient over the day, and/or symptom tracking (box 1756, 1764) can be recorded manually or electronically, such as in a software application. Knowing when and what was consumed can be used to predict when and how much a person's bowels should be emptied and the amount of treatment can be applied accordingly. The information regarding the processing time of a certain amount of food in the human body could be used to anticipate through literature studies with additional information from the patient (such as gender, weight, and height). This processing and consolidation of data to anticipate the amount and timing of treatment necessary can be done within a single device or utilizing another separate device, for instance a mobile phone. In this manner, stimulation can be applied accordingly based on the number of episodes a person experiences. One method of recording the times and types of food and drink consumed is through a journal or diary, for example on a smartphone, tablet, or other device.

In some embodiments, the systems and methods use one or more sensor devices to measure or detect breathing activity, heart rate, or blood flow pulsatility over time, then based on a predetermined relation of the measured activity, a stimulator is instructed to provide neurostimulation to at least one, two, or more of the nerve targets described. In some embodiments, the stimulated nerve targets may selectively activate the parasympathetic nervous system, the sympathetic nervous system, or both.

Figure 6M:
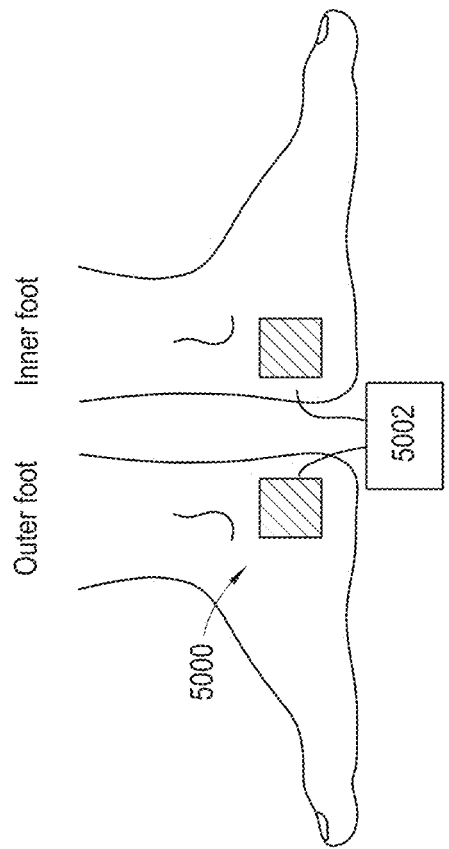
Figure 6N:
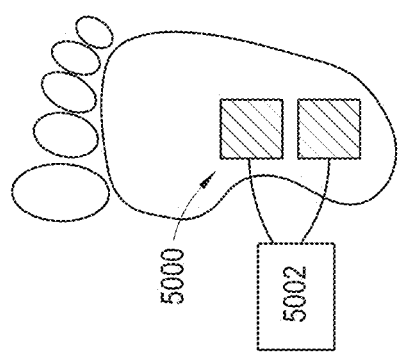

FIGS. 6L-6N illustrate non-limiting embodiments of potential electrode placement locations for nerve stimulation. The sensor systems, including those disclosed herein can communicate via wires or wirelessly to the stimulator 5002. Placement of the electrodes of the tibial stimulator could vary with electrodes 5000 placed along the tibial nerve (FIG. 6L), at the bottom of the foot (FIG. 6M), or on either side of the ankle or attached to a stimulator (FIG. 6N).

In some embodiments, disclosed herein are systems and methods for stimulating a plurality of nerves for the treatment of conditions including but not limited to IBD. Stimulation of 2, 3, or more nerves, such as the saphenous and tibial nerve could be used for the treatment of conditions such as IBD. Dual nerve stimulation can in some cases synergistically increase the effectiveness of therapy by combining synergistically the effects of, for example, saphenous and tibial nerve stimulation. In some embodiments, including those disclosed in connection with FIGS. 6O and 6P below, the system can be configured to independently control stimulation of a first target nerve (including stimulation parameters such as frequency and others listed herein) and a second target nerve respectively. In other words, the first target nerve and the second target nerve can be stimulated with either the same or different parameters, and can be stimulated simultaneously or in alternating or other fashion. In some embodiments, the stimulation systems can include a plurality of independent stimulation circuits, or a common circuit with a controller configured to switch stimulation parameters for one, two, or more nerves.

In some embodiments, as illustrated schematically in FIG. 6O, a system 1400 can utilize three electrodes: a first electrode 1404 positioned over a first nerve, e.g., the tibial nerve 1402, a second electrode 1406 positioned over a second nerve, e.g., the saphenous nerve 1408, and a third electrode 1410 positioned, for example, on the outer side of the leg, opposite to the first two electrodes 1404, 1406. This third electrode 1410 would serve as a common cathode for the other two electrodes 1404, 1406. The three electrodes 1404, 1406, 1410 can be oriented in such a way that the electric fields between each of the first two electrodes 1404, 1406 and the common cathode 1410 pass through the tibial nerve 1402 and saphenous nerve 1408, respectively.

Figure 6P:
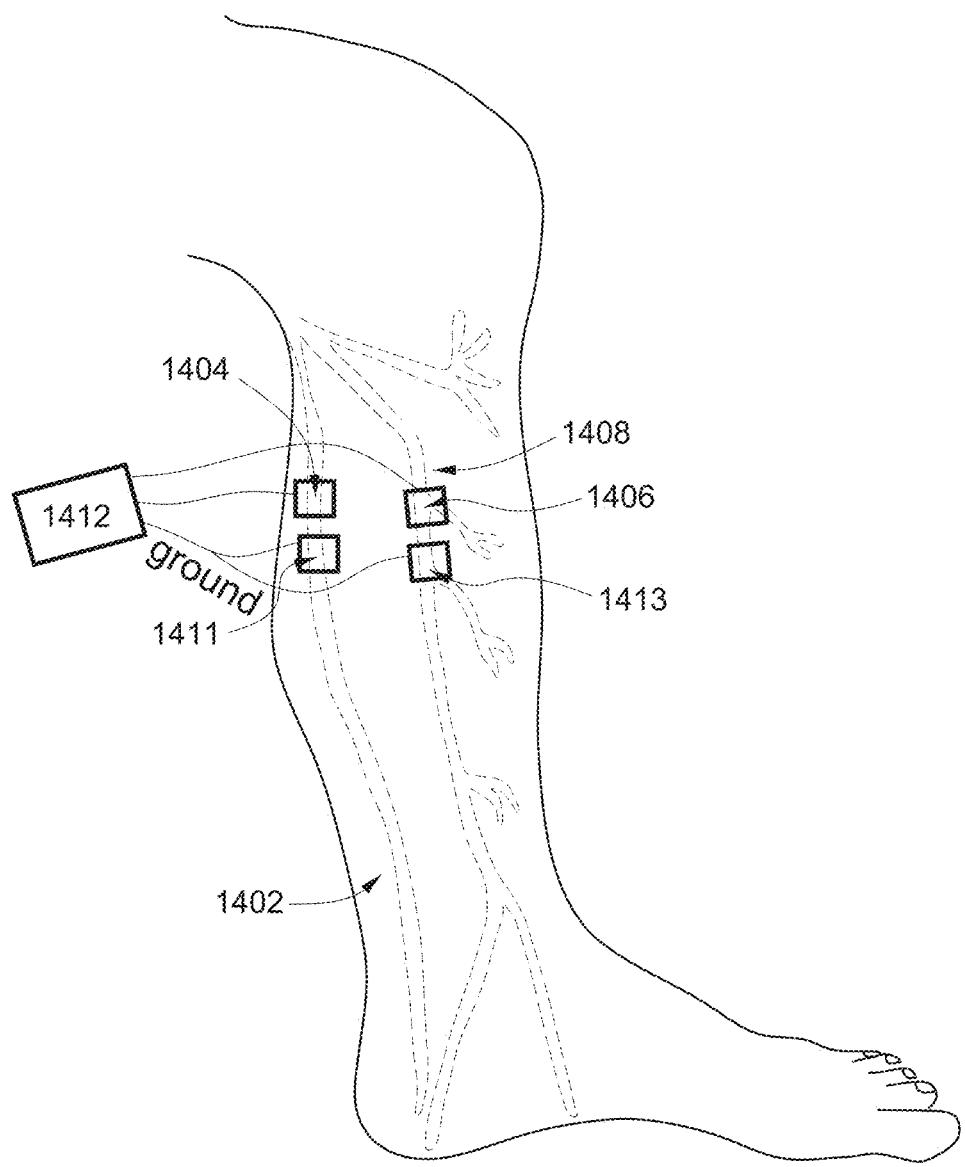

Another possible configuration shown in FIG. 6P utilizes four electrodes. Similar to the embodiment illustrated in FIG. 6O, three channels are used: a first targeting the tibial nerve 1402, a second targeting the saphenous nerve 1408, and one acting as a common cathode 1410. However, the cathode in the electronics is split between two common electrodes 1411, 1413, each serving as a cathode electrode for the other two electrodes 1404, 1406. Thus, a first electrode 1404 is positioned over the tibial nerve 1402 with a first cathode electrode 1411 positioned directly below it and a second electrode 1406 is positioned over the saphenous nerve 1408 with a second common electrode 1413 positioned directly below it. Each electrode pair 1404, 1411 and 1406, 1413 can be oriented in such a way that the electric field between the two electrodes (the electrode over the nerve and its respective common electrode) passes through the intended nerve (e.g., tibial or saphenous).

In some embodiments, stimulation can be timed to changes in heart rate and/or rhythm, as a transient tachycardia arises with every breath. A heart rate sensor could detect this rhythmic tachycardia and generate a control signal to trigger stimulation. Heart rate or rhythm sensor could be multiple or single-lead ECG sensors, wrist worn optical heart rate sensor, also known as photoplethysmograms (PPG).

In some embodiments, disclosed herein is a wearable device to deliver patterned transcutaneous electrical stimulation to peripheral nerves. In some embodiments, patterned stimulation can include one or more techniques, including but not limited to synchronizing stimulation to a phase or feature of the cardiac cycle, synchronizing stimulation to specific features of neural oscillations such as power or frequency, and alternating stimulation bilaterally across two or more nerve targets. Synchronizing stimulation to neural oscillations can promote biofeedback for the patient by promoting and reinforcing alpha wave activity in the brain, which has been shown to improve symptoms associated with inflammation. The device can include any number of a controller; a first peripheral nerve effector, comprising at least one stimulation electrode configured to be positioned to transcutaneously modulate a first afferent peripheral nerve; and at least one biomedical sensor or data input source configured to provide feedback information. The feedback information could include physiologic parameters including vital signs, measures of sympathetic or parasympathetic activity, and other information disclosed herein. The controller can include a processor and a memory for receiving the feedback information from the sensor, that when executed by the processor, cause the device to adjust one or more parameters of a first electrical stimulus based at least in part on the feedback information; and/or deliver the first electrical stimulus to the first afferent peripheral nerve to the first peripheral nerve effector. The first electrical stimulus can include patterned, such as burst (e.g., theta burst)

electrical stimulation configured to induce neural plasticity and reduce symptoms due to inflammatory diseases. The stimulation can be continuous, intermittent, or intermediate theta burst stimulation in some embodiments. The device can also be configured to deliver a priming electrical nerve stimulation signal prior to the first electrical stimulation signal, which can be a non-theta burst stimulation signal. The device can further include a second peripheral nerve effector, including at least one stimulation electrode configured to be positioned to transcutaneously modulate a second afferent peripheral nerve, and is configured to deliver a second electrical nerve stimulation signal transcutaneously to the afferent peripheral nerve of the user. The signal can include, for example, electrical theta burst stimulation.

In some embodiments, inhibition of the inflammatory response by stimulation may also reduce the symptoms of other diseases, including but not limited to, rheumatoid arthritis or other non-limiting examples disclosed herein, or acute or chronic injury/trauma. Direct stimulation could be applied to the joint in some cases. Stimulation could be gated based on swelling measured in the joint, pain or activities of daily living scores, and the like.

In some embodiments, inflammation can be assessed in a patient by a sensor or plurality of sensors to quantify the level of inflammation. Inflammation is a central component of innate (non-specific) immunity. In generic terms, inflammation is a local response to cellular injury that is marked by increased blood flow, capillary dilatation, leucocyte infiltration, and the localized production of a host of chemical mediators, which serves to initiate the elimination of toxic agents and the repair of damaged tissue. Termination of inflammation is an active process involving cytokines and other anti-inflammatory mediators, particularly lipids, rather than simply being the switching off of pro-inflammatory pathways.

Inflammation can be assessed non-invasively in some cases by ultrasound molecular imaging with a dual P- and E-selectin-targeted contrast agent.

Inflammation can also be assessed by a range of blood cellular markers (e.g. total leukocytes, granulocytes and activated monocytes) and soluble mediators (cytokines and chemokines (TNF, IL-1, IL-6, IL-8, CC chemokine ligand 2 (CCL2), CCL3, CCL5), adhesion molecules (vascular cell adhesion molecule-1, intercellular adhesion molecule-1, E-selectin), adipokines (adiponectin) and acute-phase proteins (ESR, CRP, serum amyloid A, fibrinogen)). The markers can be assessed via periodic blood draws, or indwelling biosensors in some cases. In some embodiments, disclosed herein are wearable systems and methods that can utilize transcutaneous sensory stimulation in the form of a burst pattern, e.g., a theta burst pattern to improve inflammatory bowel disease, and/or a variety of other inflammatory conditions, including but not limited to those disclosed herein. Noninvasive peripheral nerve theta burst stimulation may be effective in some cases in driving cortical or spinal plasticity more efficiently than continuous stimulation to reduce symptoms and improve an individual's quality of life.

In some embodiments, the stimulation involves patterns of electromagnetic stimulation of peripheral nerves. The patterned stimulation could be a bursting stimulation, such as an on/off pattern that repeats at regular intervals (e.g., on for 10 ms, off for 20 ms, etc.), or non-burst patterned stimulation that can be more complex in some embodiments, such as a stochastic pattern or a sinusoidal envelope for example. The electromagnetic stimulation could include, for example, electrical energy, mechanical energy (e.g., vibration), magnetic energy, ultrasound energy, radiofrequency energy, thermal energy, light energy (such as infrared or ultraviolet energy for example), and/or microwave energy, or combinations thereof. In some embodiments, the stimulation is limited to only electrical energy (e.g., no magnetic or other types of energy are applied). The peripheral stimulation could include transcutaneous, percutaneous, and/or implanted stimulation.

Some embodiments can involve rhythmic bursting on the median, radial, and/or ulnar nerves to balance sympathetic and parasympathetic tone.

Not to be limited by theory, alternating bursting stimulation on the medial, radial, and/or ulnar nerves can prevent inflammation by having a synergistic effect that increases input to the nucleus of the solitary tract (NTS) in the medulla and influences the activity of NTS neurons projecting to the inhibitory vagal efferent neurons of the dorsal vagal nucleus (DVN) and nucleus ambiguous (NA). Alternating bursting stimulation of the medial, radial, and/or ulnar nerves may also excite NTS neurons sending excitatory projections to the caudal ventrolateral medulla (CVLM). The CVLM inhibits the rostroventrolateral medulla (RVLM) which is the primary source of excitatory drive to sympathetic preganglionic neurons in the intermediolateral cell column (IML) of the spinal cord. This inhibition could decrease sympathetic activity. This stimulation pattern could improve sympathovagal balance to reduce inflammation.

Interferential Stimulation can be utilized in some cases. In some embodiments, a device can include a plurality of electrodes, e.g., four electrodes to where a first electrode pair stimulates at a specified first frequency, f Hz, and a second electrode pair stimulates at a second frequency slightly higher or lower than the first pair, f±x Hz. In some embodiments, the second frequency can be different from that of, but within about ±20%, 15%, 10%, 9%, 8%, 7%, 6%, 5%, 4%, 3%, 2%, or 1% of the first frequency. In some embodiments, stimulation does not involve interferential stimulation.

Figure 7A:
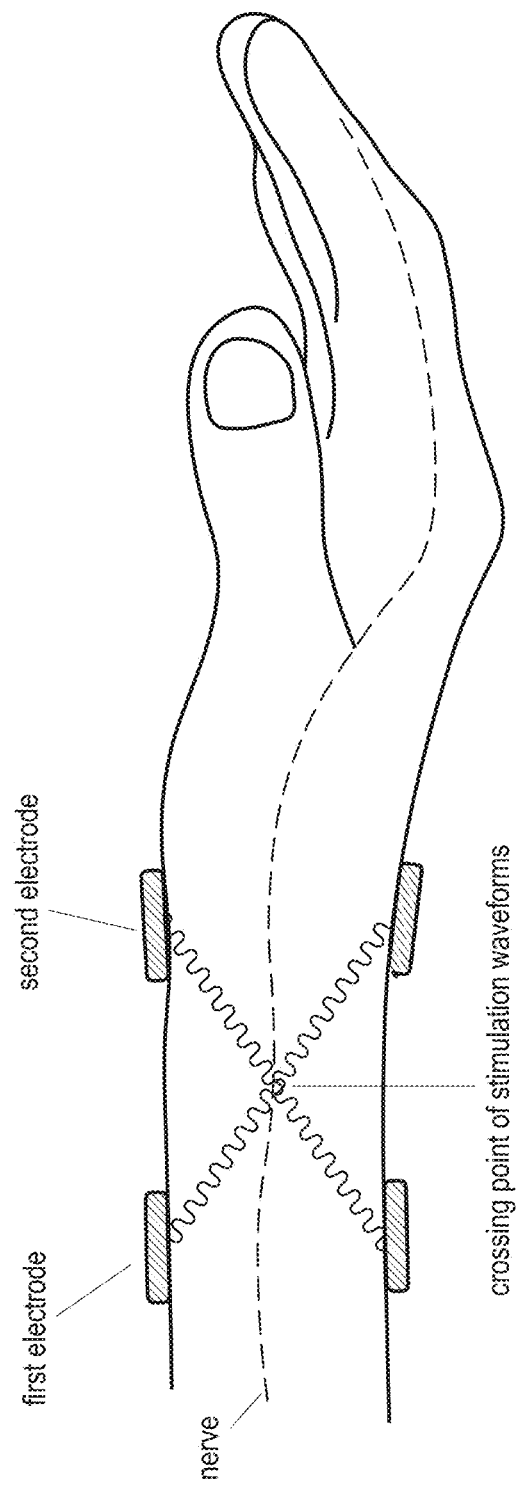
Figure 7B:
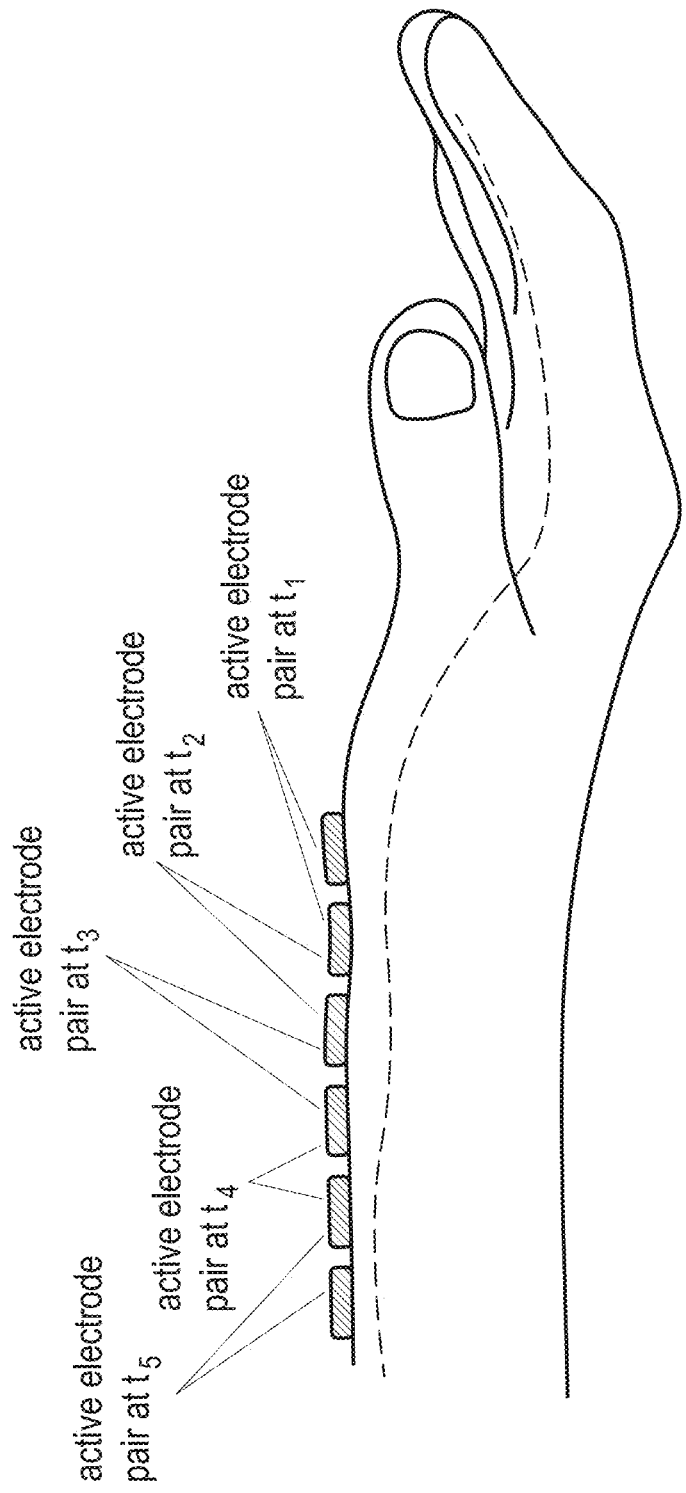

In some embodiments, the electrode pairs can be spaced on the limb, as shown in FIG. 7A, such that the stimulation waveforms combine at a specific crossing point to target deep fibers in the limb by creating an interferential pattern of stimulation with a frequency that is the difference between the frequencies of the two waveforms, e.g., x Hz.

The stimulation frequency can be varied depending on the desired clinical result. In some embodiments, a relatively higher frequency, such as between about 10 Hz and about 33 Hz, between about 10 Hz and about 30 Hz, between about 10 Hz and about 20 Hz, or between about 20 Hz and about 33 Hz, or about or at least about 10 Hz, 15 Hz, 20 Hz, 25 Hz, 30 Hz, 33 Hz, 35 Hz, or more can be used. The stimulation frequency can also be tailored to the specific nerve targeted. In some embodiments, lower stimulation rates such as 2 Hz can have an excitatory effect. However, in some embodiments, a frequency of about or no more than about 10 Hz, 9 Hz, 8 Hz, 7 Hz, 6 Hz, 5 Hz, 4 Hz, 3 Hz, 2 Hz, or 1 Hz can be utilized. In some embodiments, the stimulation frequency could be in the kHz range, such as, for example, between about 1 kHz and about 100 kHz, such as between about 10 kHz and about 50 kHz. The stimulation could be regular, irregular, or random in some embodiments. In some embodiments, a frequency or a plurality of frequencies for one, two, or more nerves could be selected from, for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 Hz. In some embodiments, two or more of the same or different frequencies or frequency ranges can be applied to the same or different target nerves.

In some embodiments, waveforms including those described herein can be modified over time in order to minimize certain effects, such as habituation. One way of decreasing habituation is to modify the frequency, pulse width, or amplitude of the stimulation. For instance, randomizing or pseudo-randomizing parameters such as, for example, the frequency or pulse width can reduce habituation. Using a Gaussian distribution for randomization can be effective in some cases, and used in such waveforms as stochastic waveforms. Another way of reducing habituation is to the lower the frequency below a certain threshold, such as, for example, no more than about 60 Hz, 55 Hz, 50 Hz, 45 Hz, or 40 Hz, in which humans tend not to habituate. Bursting to improve efficiency or efficacy of stimulation can also be used. Not to be limited by theory, bursting at a rhythmic pattern can improve efficiency of therapeutic benefit by promoting plasticity of corticospinal circuits. Rhythmic or pseudorandom bursting patterns can prevent habituation of nerves, which occurs with constant stimulation.

Some embodiments can involve stimulation patterns (e.g., bursting, pulse patterns, random, pseudo-random, or noise) selected to improve the efficiency and efficacy of stimulation. In some embodiments, as illustrated schematically in FIG. 7B, an array of electrodes can be aligned along the axon of the nerve that stimulate adjacent pairs of electrodes at regular intervals such that specific points along the nerve are stimulated at a velocity of, for example, between about 1 cm/s and about 10 cm/s. In some embodiments, stimulation can be provided in a bursting pattern where the bursting can either be rhythmic (e.g., at regular intervals) or pseudorandom. In some embodiments, a stimulation waveform can be provided that combines infraslow stimulation frequency (0.01-0.1 Hz) with a higher frequency stimulation (1-200 Hz), or lower frequency (1-200 Hz) with very high frequencies (1000-10 kHz).

In some embodiments, the stimulation involves non-invasive transcutaneous electrical patterned or burst stimulation of peripheral nerves, including afferent and/or efferent nerves. Not to be limited by theory, but burst stimulation of peripheral nerves can unexpectedly result in one or more of the following compared with conventional or continuous stimulation: greater efficacy; greater plasticity; increased tolerance or tolerability; reduced effects of habituation; increased comfort; and/or reduced treatment time required to achieve the same beneficial effects. Burst stimulation of peripheral nerves, including afferent nerves, can in some cases deliver a more efficacious therapy by remotely accelerating plasticity of one or more central nervous system (e.g., brain and/or spinal cord) circuits, in other words creating plasticity in neural circuits for a period of time that is far longer than the duration of the stimulation session, such as, for example, about or at least about 6 hours, 12 hours, 24 hours, 2 days, 3 days, 4 days, 5 days, 6 days, 7 days, 2 weeks, 3 weeks, 1 month, 2 months, 3 months, 4 months, 5 months, 6 months, 9 months, 12 months, 18 months, 24 months, 36 months, or even longer. Peripheral stimulation in some cases can be more convenient and comfortable for the user than central stimulation (e.g., transcranial stimulation and/or spinal stimulation) and can be more suitable for home and ambulatory use.

In some embodiments, the burst stimulation includes theta burst stimulation. Theta burst stimulation (TBS) is a patterned form of repetitive stimulation that uses high frequency pulses separated by varying inter-burst intervals. Originally used for the induction of long term potentiation in hippocampal learning and memory research, theta burst stimulation in the form of repetitive magnetic stimulation (rTMS) has been demonstrated to noninvasively induce plasticity in humans in the motor, sensory and visual cortex. Depending on various parameters including the duration and continuity of stimulation, a long term potentiation or depression (LTP/LTD) like effect can be observed, which are surrogate measures of synaptic efficacy. The number of sessions and the spacing interval between individual sessions of stimulation can also have an effect on the duration of the induced response. The level of muscle relaxation before or during stimulation can also affect the resulting direction or amplitude of plasticity induction suggesting that homeostatic mechanisms are in place that adjust the threshold for plasticity depending on prior synaptic activity. The effective modulation of nervous system plasticity demonstrated with theta burst stimulation can have great potential for the treatment of various neurologic disorders, and can have an effect on other central neural circuits.

Figure 8:
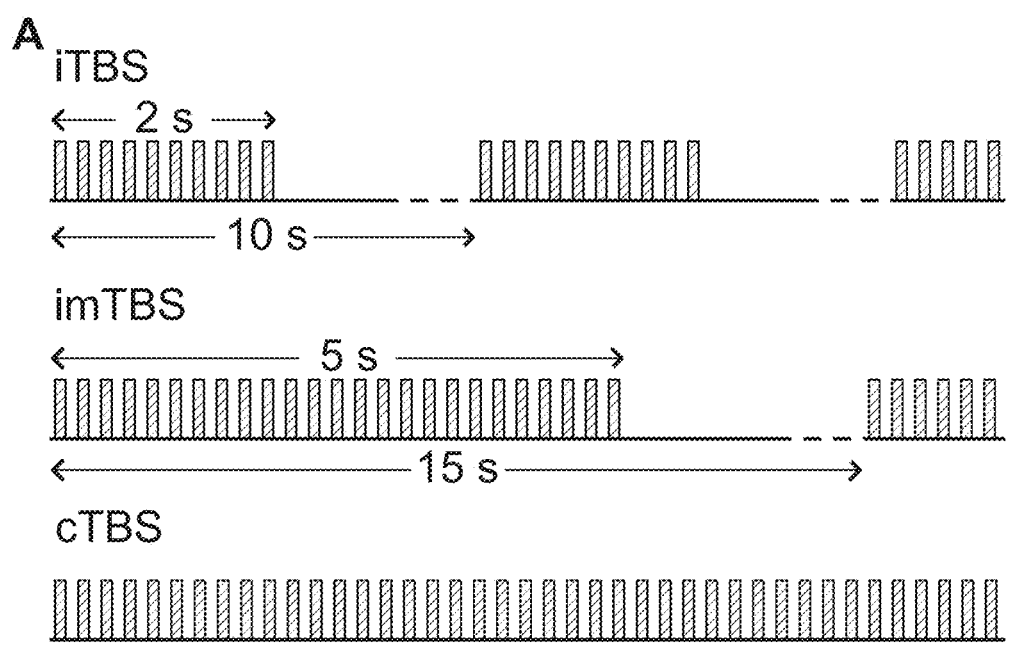
FIG. 8 illustrates non-limiting examples of iTBS, cTBS, and imTBS.

In some embodiments, theta burst stimulation can take the form of intermittent theta burst stimulation (iTBS), continuous theta burst stimulation (cTBS), and intermediate theta burst stimulation (imTBS). Non-limiting examples of iTBS, cTBS, and imTBS are illustrated in FIG. 8. Each illustrate examples of TBS including a burst of 3 stimuli at 50 Hz (20 ms between each stimulus) which was repeated at inter-burst intervals of 200 ms (5 Hz). In the iTBS example pattern, an about 2 second train of TBS is repeated about every 10 seconds for a total of 190 seconds (600 pulses). In the imTBS example pattern, an about 10 second train of TBS is repeated every 15 seconds for a total of 11 seconds (600 pulses). In the cTBS pattern, a 40 second train of uninterrupted TBS is given (600 pulses). The burst pattern (or a combination of two or more burst patterns) can be selected depending on the desired clinical result. In some cases, cTBS can be inhibitory, iTBS can be excitatory, and imTBS can be neither excitatory nor inhibitory, but this may be varied depending on the parameters. In some embodiments, inhibitory stimulation of a first nerve (e.g., the median, ulnar, or radial nerve) can be used alone or in combination with excitatory stimulation of a second nerve (e.g., the median, ulnar, or radial nerve), such as to restore or improve sympathetic and parasympathetic balance. In some embodiments, inhibitory or excitatory stimulation of a nerve can be controlled by adjusting frequency or pulse width of the stimulation waveform.

Figure 9A:
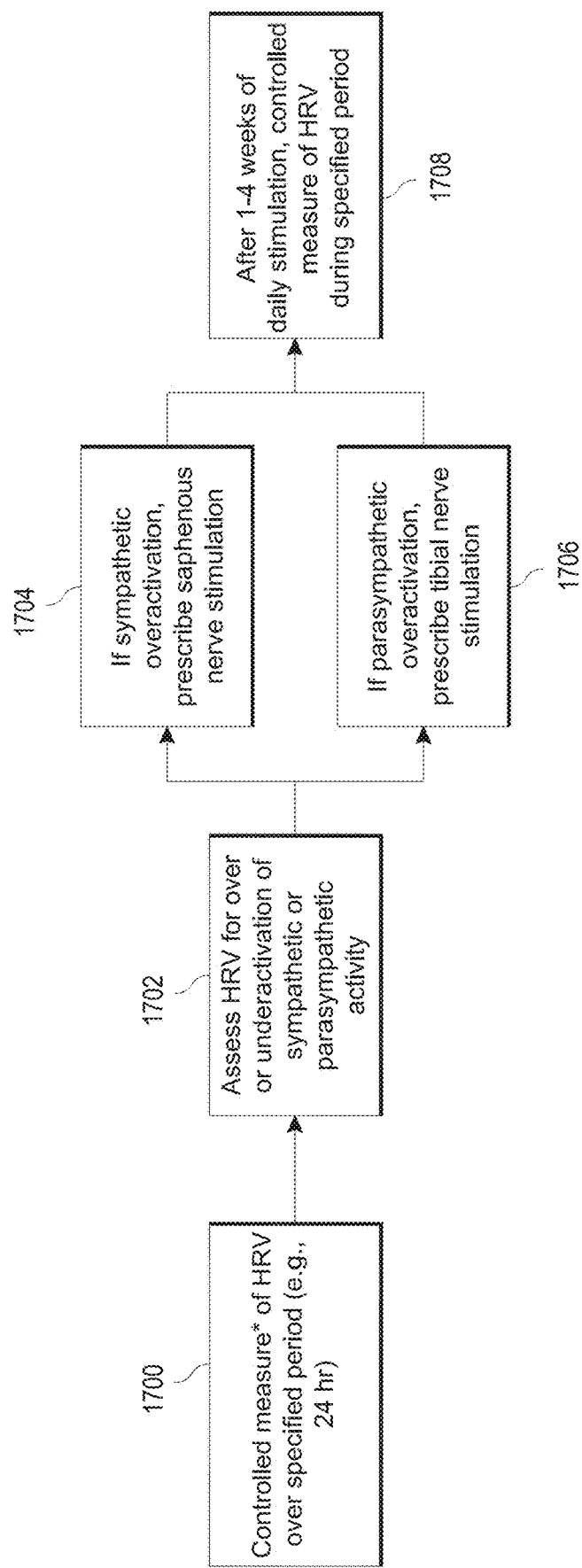
FIGS. 9A-9C illustrate flow charts relating to therapeutic methods involving stimulation for treating inflammatory disorders, according to some embodiments of the invention.

FIG. 9A illustrates a flow chart of an example of a therapeutic protocol for treating IBD or another disorder, according to some embodiments of the invention. In some embodiments, sympathetic and parasympathetic activity can be assessed during a baseline period (e.g., from about 24 hours to about 30 days in some embodiments) using sensors that measure heart rate and heart rate variability, and/or electrodermal activity 1600. Heart rate and HRV can be measured in various ways and sympathetic and/or parasympathetic overactivation or underactivation assessed 1702, including an optical sensor in a wrist worn device, a chest strap or patch that measures changes in electrical activity, a pulse oximeter worn on the finger, and the like. Sympathetic and parasympathetic activity can also be measured using electrodermal activity sensors as described elsewhere herein. In some embodiments, a single device can include both an optical heart rate sensor and electrodermal activity sensors to improve the estimation of sympathetic and parasympathetic activity. If sympathetic overactivation is identified 1704 (e.g., from HRV and/or other autonomic measurements), saphenous nerve stimulation can be initiated (e.g., saphenous nerve stimulation alone without tibial nerve stimulation). If parasympathetic overactivation is identified

1706, tibial nerve stimulation can be initiated (e.g., tibial nerve stimulation alone without saphenous nerve stimulation). After a period (e.g., about 1-4 weeks) of stimulation, a controlled measure of autonomic function, e.g., HRV, can be reassessed 1708.

Figure 9B:
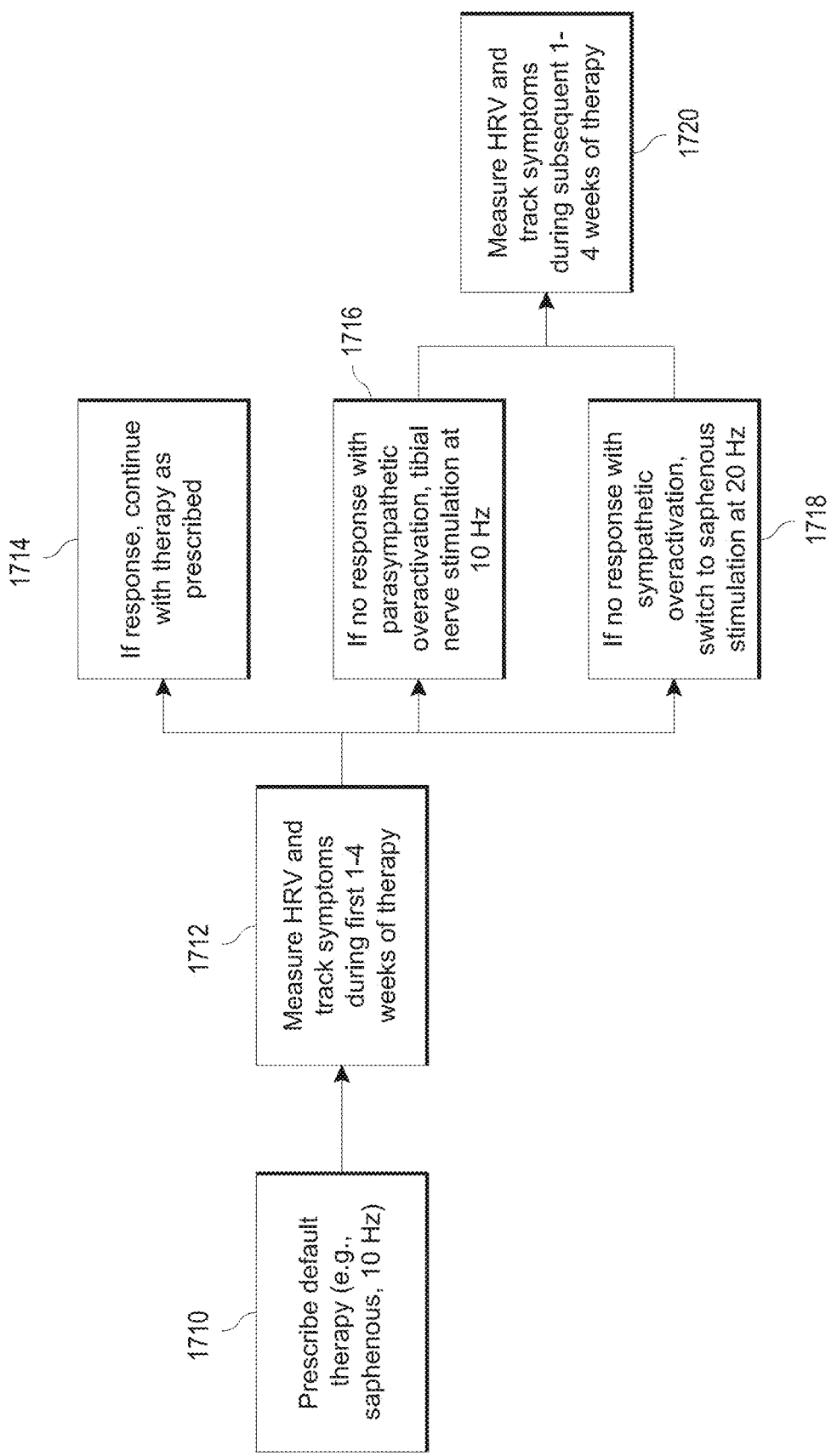
Figure 9C:
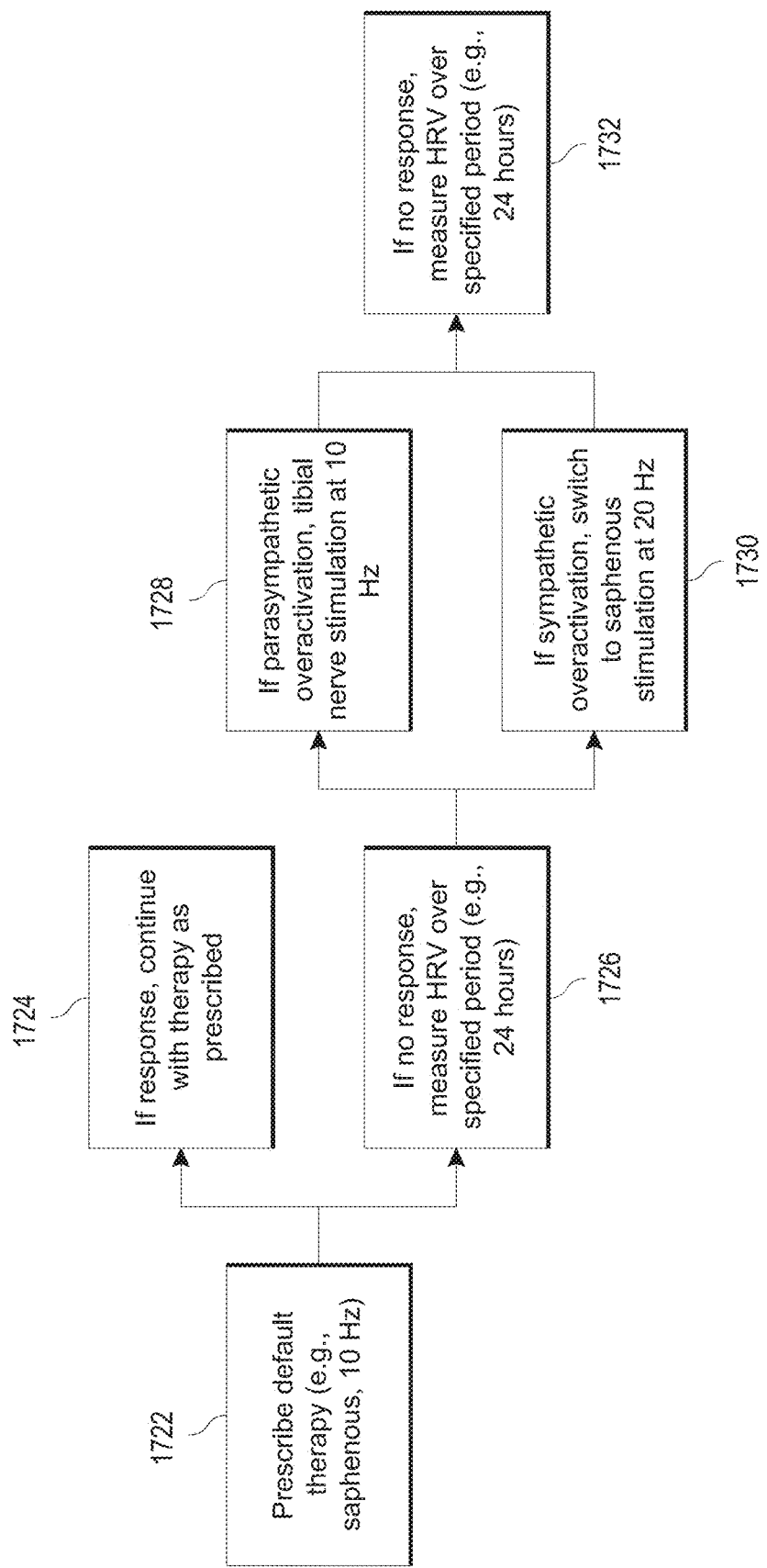

In some embodiments, sympathetic and parasympathetic activity are assessed prior to initial stimulation to select specific nerve targets, stimulation waveforms, stimulator parameters, or dosing of stimulation (e.g., time of day, duration of stimulation, number of times per day or week). In other embodiments, a default stimulation is applied in a trial fashion, and only if a person does not respond to treatment is sympathetic and parasympathetic activity assessed. In some embodiments, sympathetic and parasympathetic activity are assessed over a single day or over multiple days during an initial period of treatment to measure any changes in autonomic activity. In some embodiments, IBD or other symptoms may be tracked by the patient, either manually or on paper, onboard the stimulation device, or on an external computing device such as a smartphone, tablet, laptop, etc. to be correlated with parameters, such as HRV and changes in autonomic activity, for example. As illustrated in FIG. 9B, a default therapy is prescribed (e.g., 10 Hz saphenous nerve stimulation) 1710, and parameters such as HRV are measured (e.g., during the first 1-4 weeks of therapy), and symptoms tracked 1712. If there is an acceptable response to therapy, it can be continued as prescribed 1714. If no response to therapy and parasympathetic overactivation is determined 1716, a second therapy can be added (e.g., 10 Hz tibial nerve stimulation). If there is no response and sympathetic overactivation is determined, therapy can be switched to an alternative therapy 1718 (e.g., 20 Hz saphenous nerve stimulation). Parameters such as HRV are measured, and symptoms tracked during a subsequent therapy period 1720. As illustrated in FIG. 9C, a default therapy is prescribed (e.g., 10 Hz saphenous nerve stimulation) 1722, although parameters such as HRV need not necessarily be measured. If there is an acceptable response to therapy, it can be continued as prescribed 1724. If no acceptable response to therapy, parameters such as HRV can be measured 1726. If no response to therapy and parasympathetic overactivation is determined 1728, a second therapy can be added (e.g., 10 Hz tibial nerve stimulation). If there is no response and sympathetic overactivation is determined, therapy can be switched to an alternative therapy 1730 (e.g., 20 Hz saphenous nerve stimulation). If no response, parameters such as HRV are measured, and symptoms tracked during a subsequent therapy period 1732.

In some embodiments, if a person does not respond to therapy, a number of parameters can be altered to modify therapy, including but not limited to increasing or decreasing, or otherwise changing any number of the following: duration of session (e.g., 20-120 minutes); number of sessions per day or week (e.g., 2 times per day to 3 times per week); time of day or night of stimulation; stimulation frequency; bursting or other stimulation pattern (including bursting frequency); nerve target (e.g., saphenous or tibial); and/or stimulation amplitude.

In some embodiments, therapy can have an unexpectedly synergistic effect when combined with one, two, or more pharmacologic agents. Anti-inflammatory drugs are often the first step in the treatment of inflammatory bowel disease. Anti-inflammatories include corticosteroids and aminosalicylates, such as mesalamine (Asacol HD, Delzicol, others), balsalazide (Colazal) and olsalazine (Dipentum). Immunosuppressant drugs can also be utilized in therapy. Some examples of immunosuppressant drugs include azathioprine (Azasan, Imuran), mercaptopurine (Purinethol, Purixan), cyclosporine (Gengraf, Neoral, Sandimmune), tacrolimus, and methotrexate (Trexall). One class of drugs called tumor necrosis factor (TNF)-alpha inhibitors, or biologics, works by neutralizing a protein produced by the immune system, such as with a monoclonal antibody. Examples include infliximab (Remicade), adalimumab (Humira) and golimumab (Simponi). Other biologic therapies that may be used are natalizumab (Tysabri), vedolizumab (Entyvio) and ustekinumab (Stelara). Antibiotics may be used in addition to other medications or when infection is a concern—in cases of perianal Crohn's disease, small intestinal bacterial overgrowth (SIBO), and others for example. Frequently prescribed antibiotics include a quinolone such as ciprofloxacin (Cipro), metronidazole (Flagyl), vancomycin (Vancocin), and rifaximin (Xifaxan), among others.

In some embodiments, the effector can be excitatory to the nerve. In other embodiments, the effector can be inhibitory to the nerve. In some embodiments, the system can be used to excite the nerve during some portions of the treatment and inhibit the nerve during other portions of the treatment.

In several embodiments, over-the-counter agents such as loperamide and bismuth compounds (e.g., loperamide hydrochloride and bismuth subsalicylate) work in a synergistically beneficial manner with the neuromodulation (e.g., neurostimulation) embodiments described herein. In some embodiments, the use of neuromodulation (e.g., neurostimulation) as described herein results in a greater half-life of pharmacological agents and/or a reduced dosage. This can be particularly helpful to manage the side effects of these agents, which can be exacerbated in patients with sensitive digestive tracts. Dosages when combined with neurostimulation are reduced, in some embodiments, by at least 5%, 10-20%, 20-40%, 40-60% or more (including overlapping ranges therein) as compared to dosages needed to achieve a similar effect in the absence of neurostimulation. In one embodiment, the combination of neurostimulation and a pharmacological agent allows the pharmacological agent to work more quickly (e.g., 20-60% more rapidly, or higher).

Some embodiments, as shown in FIGS. 11, 12A-12D for example, are related to a device and system that provides peripheral nerve stimulation, targeting individual nerves. Some embodiments involve a device and system 10 that allows customization and optimization of electrical treatment to an individual. In particular, the device 10 described can be configured for electrical stimulation of the median, radial, ulnar, auricular vagus, peroneal, saphenous, tibial and/or other nerves or meridians accessible on the limbs, head, neck, or ears, for treating inflammatory bowel diseases. Targeting those specific nerves and utilizing appropriately customized stimulation surprisingly results in more effective therapy. In some embodiments, therapy can reduce or eliminate the number, dose, and/or frequency of medications that a patient may need to take for their inflammatory bowel disease or other medical condition, advantageously reducing side effects/potential toxicities. In some embodiments, therapy can have an unexpectedly synergistic effect when combined with one, two, or more pharmacologic agents.

Figure 10A:
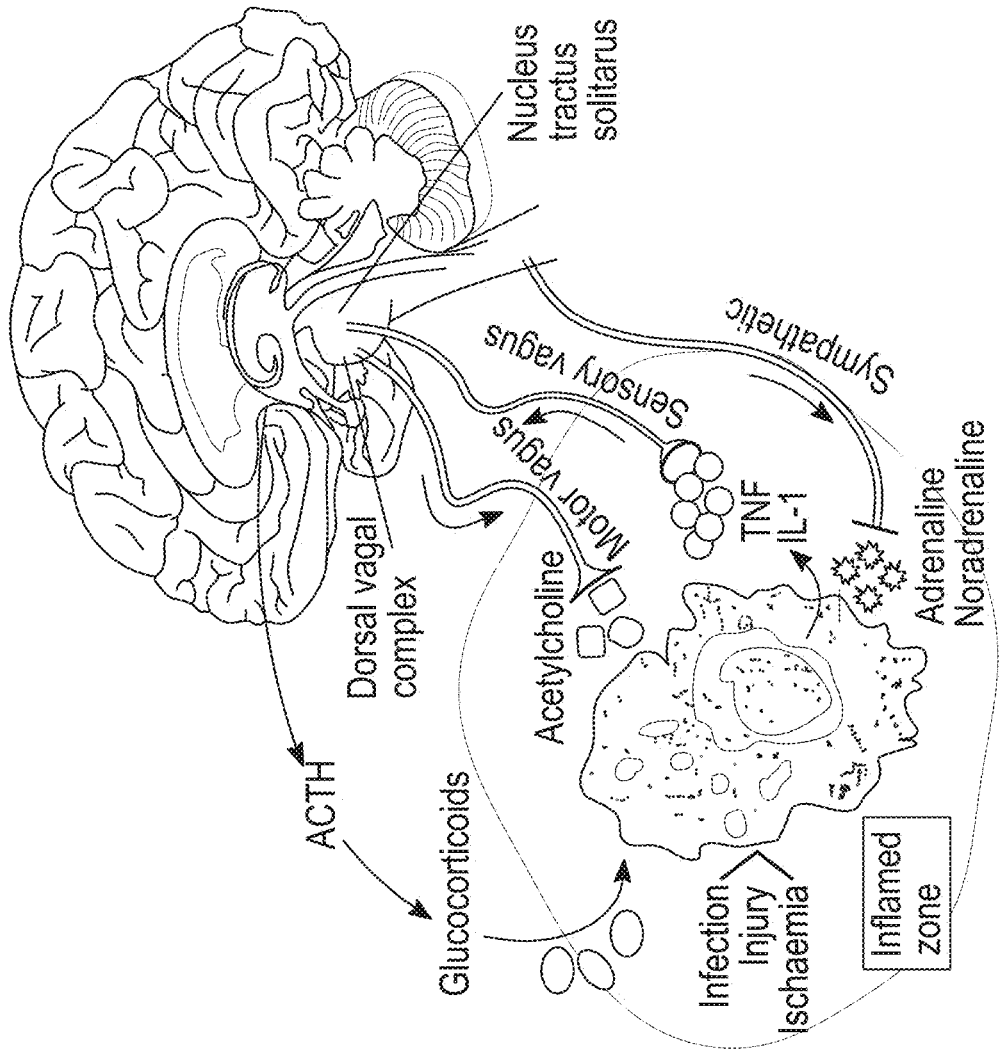
FIGS. 10A-B illustrate the neural pathways that can be modulated to reduce inflammatory response.
Figure 10B:
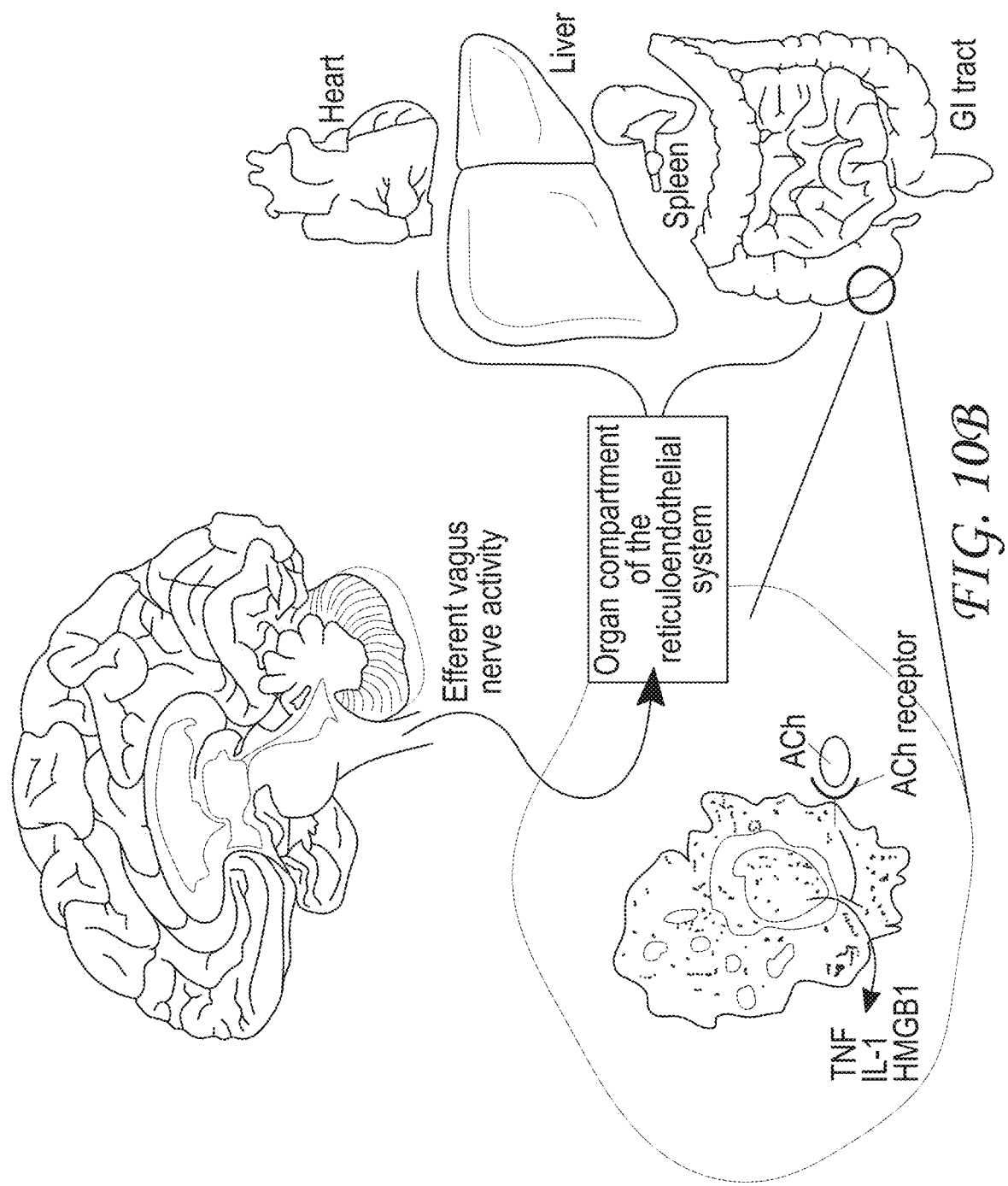
Figure 11A:
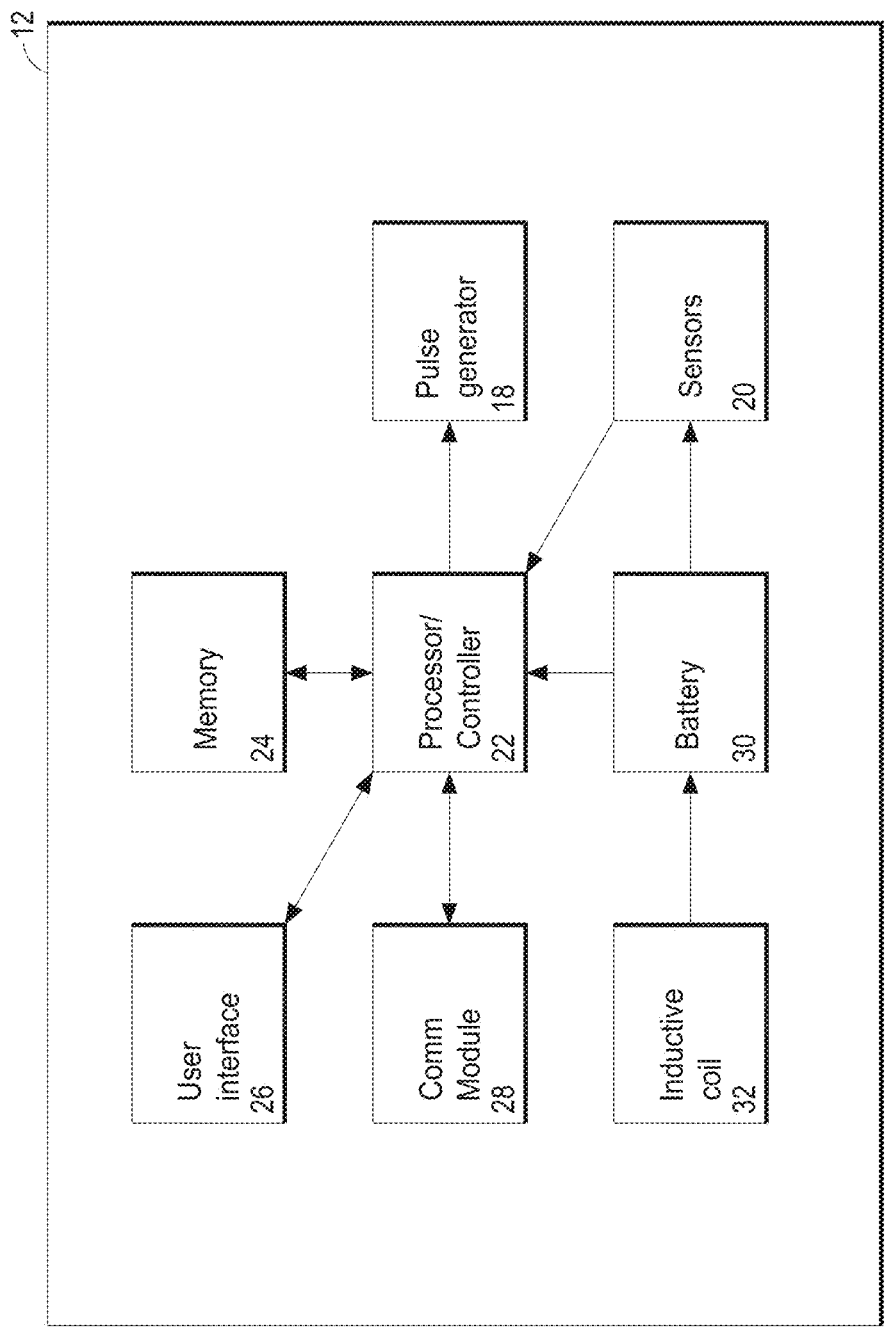
FIG. 11A illustrates a block diagram of an embodiment of a device and system that provides peripheral nerve stimulation and senses a biological measure that is used to customize or modify the delivery of an electrical stimulus.

Afferent nerves in the periphery or distal limbs, including but not limited to the median nerve, are connected via neural pathways to sensitized peripheral and central neurons connected to the nucleus tractus solitarus; vagus nerve; or other regions of the brain and brain stem associated with regulation of inflammation, as illustrated in FIGS. 10A-10B.

FIGS. 11, 12A-12D illustrate an embodiment of a device and system 10 that provides transcutaneous peripheral nerve stimulation, targeting individual nerves, to treat inflammatory bowel disease or other inflammatory conditions. In some embodiments, the device 10 is designed to be worn on the wrist or arm; leg; or in or around the ear. In some embodiments, electronics located in a watch-like housing 12 measure heart rate, motion, and/or electrodermal activity, and also generate an electrical stimulation waveform. Electrical contacts in a band 14 and/or housing 12 transmit the stimulation waveform to the disposable electrodes 16. The location of the contacts in the band 12 is arranged such that one or more specific nerves are targeted at the wrist, such as the median, radial, and/or ulnar nerves on the arm; tibial, saphenous and/or peroneal on the leg; auricular branch of the vagus nerve or trigeminal nerve in or around the ear. The electronics housing 12 also can have a digital display screen to provide feedback about the stimulation and sensor measurements, derived characteristics and history to the wearer of the device.

In some embodiments, the treatment device 10 is a wrist-worn device that can include, for example, 1) an array of electrodes 16 encircling the wrist, 2) a skin interface to ensure good electrical contact to the person, 3) an electronics box or housing 12 containing the stimulator or pulse generator 18, sensors 20, and other associated electronics such as a controller or processor 22 for executing instructions, memory 24 for storing instructions, a user interface 26 which can include a display and buttons, a communications module 28, a battery 30 that can be rechargeable, and optionally an inductive coil 32 for charging the battery 30, and the like, and 4) a band to hold all the components together and securely fasten the device around the wrist of an individual.

In FIG. 12D, electrodes 16 are placed circumferentially around the wrist and excited on opposite sides of the wrist, the electric field extends through the wrist and this enables excitation of nerves deeper in the tissue. Therefore, the circumferential array is compact, allowing a band width that is approximately the same size as the electrode width, and thus advantageous for wearable devices. In some embodiments, the advantage of having the configurability of the array is that the same nerves can be reached, but in a more compact form factor than conventional median nerve excitation. The devices described herein may be described and illustrated with electrodes placed circumferentially or longitudinally, but it should be understood that either electrode configuration can be used by the devices. In addition, the devices may be described and shown with 2, 3 or more electrodes, but it should be understood that the device can have only 2 electrodes, or can have more than 2 electrodes. Some devices may be designed to stimulate just a single nerve, such as the median nerve, and some devices may be designed to stimulate more than one nerve.

Figure 13A:
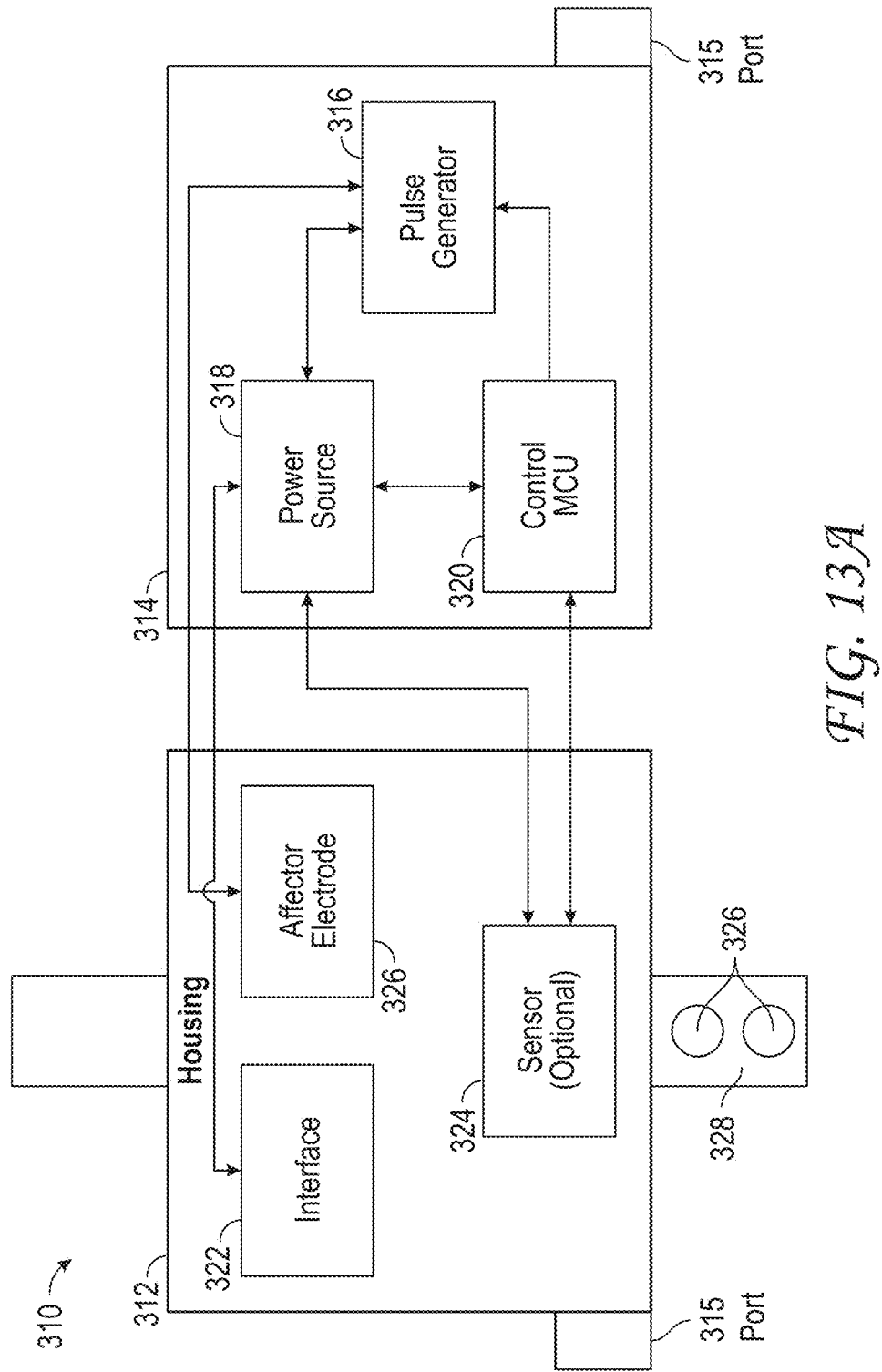
FIGS. 13A and 13B illustrate various embodiments of a monitoring unit and a therapy unit that form a two-part treatment system.

One embodiment, as shown in FIG. 13A, is a two-part system 310 including a monitor unit 312 that can be wearable in some embodiments and a therapy unit 314. In some embodiments, the therapy unit 314 can be can be detachable and can be reversibly attached to the wearable monitor unit 312. The therapy unit 314 may contain an electrical stimulation signal generator 316, power source 318, and a microprocessor and/or microcontroller 320 to control the stimulation. The therapy unit 314 can reversibly connect and communicate directly and/or wirelessly to the wearable monitor unit 312. In some embodiments, the therapy unit 314 may remain separate from the wearable monitor unit 312 and can communicate wirelessly with the wearable monitor unit 312. In some embodiments, the therapy unit 314 can have a data/power port 315, such as a USB port that allows a user to charge the power source 318, update the software and/or parameters on the microcontroller 320, and/or retrieve data from memory on the wearable monitor unit 312 and/or therapy unit 314. In some embodiments, the data/power port can be located on the wearable monitor unit 312 or both the wearable monitor unit 12 and therapy unit 314. In some embodiments, the wearable monitor unit 312 and/or therapy unit 314 can communicate wirelessly with an external computing device to update the software and/or parameters and/or retrieve data.

In some embodiments, the wearable monitor unit 312 can have a housing with a user interface 322 that encloses one or more sensors 324. In some embodiments, the wearable monitor 312 can be used to measure heart rate, rhythm, heart rate variability (HRV), or other measures correlated or related to inflammatory bowel disease or other inflammatory conditions, or response of the autonomic nervous system. In some embodiments, the wearable monitor 312 can have one or more electrodes 326 located on the base of the housing that makes contact with the patient's skin. In addition, or alternatively, the wearable monitor 312 can have a band 328 or other securement feature with one or more electrodes on the skin facing side of the band 328. In some embodiments, the wearable monitor unit 312 has exactly or no more than 2 or 3 electrodes, or at least 2 or 3 electrodes. In some embodiments, the wearable monitor unit 312 lacks a power source and relies on the power source 318 in the therapy unit 314 for power. In other embodiments, both the wearable monitor unit 312 and the therapy unit 314 have power sources. In some embodiments, only the wearable monitor unit 312 has a power source and the therapy unit relies on power from the monitoring unit.

Figure 13B:
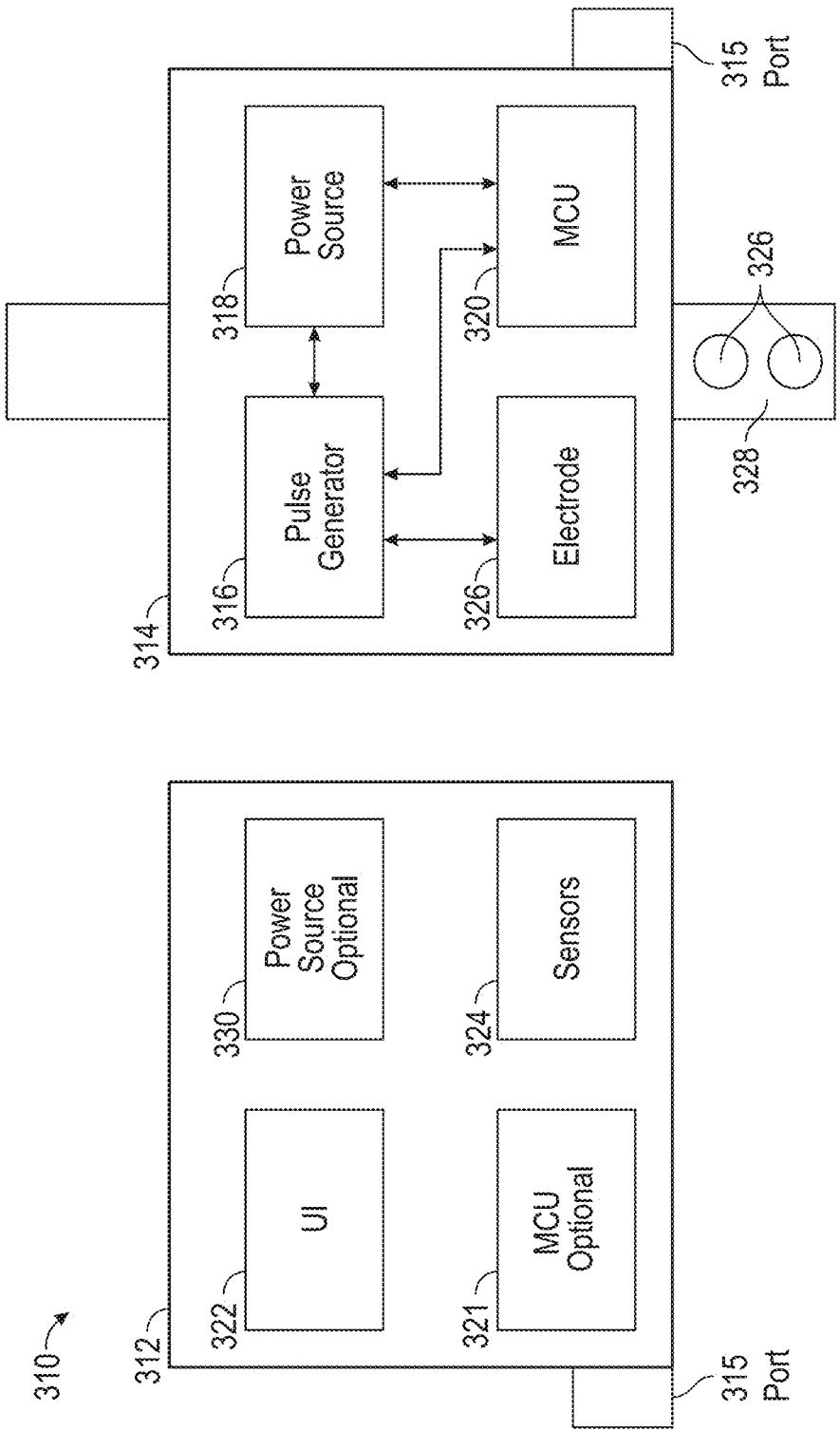

In some embodiments, as shown in FIG. 13B, the therapy unit 314' may directly make contact with the wearer's skin and have the capability to provide electrical stimulation of targeted nerves, such as the median, radial, ulnar, and/or ABVN, using electrodes 326. In some embodiments, the therapy unit 14' has 2 or 3 electrodes, or at least 2 or 3 electrodes. These electrodes 326 may be located on the housing of the therapy unit 314' and/or the therapy unit 314' may also have a band 328 or securement feature with electrodes 326. In some embodiments, when the therapy unit 314' has electrodes 326, the wearable monitor unit 312' does not have electrodes. In some embodiments, both the monitor unit and the therapy unit can have electrodes. As above, the therapy unit 314' can have a stimulator 316, power source 318, and microcontroller 320. The wearable monitor unit 312' can have a user interface 322 and one or more sensors 324 and, optionally, a power source 330 and microcontroller 321. In some embodiments, when the monitor unit has a power source 330 and/or a microcontroller 321, the therapy unit does not have a power source and/or a microcontroller. In some embodiments, the wearable monitor unit 312' is a smart watch or other wearable device, such as the Apple Watch or an Android based smart watch, with an application that allows the wearable device to communicate with the therapy unit and perform as a monitor unit. In some embodiments, the wearable monitor unit 312' can communicate with the therapy unit 314' wirelessly, and one or both of these devices can also communicate with an external computing device wirelessly. In some embodiments, one or both of the wearable monitor unit 312' and the therapy unit 314' can have a data/power port 315. In some embodiments, the wearable monitor unit 312 and the therapy unit 314' can be connected to each other through the data/power ports 315.

In some embodiments, the sensors can be located in or on the therapy unit instead of the monitoring unit. In some embodiments, the sensors can be located on both the therapy unit and the monitoring unit. In some embodiments, one or more sensors can be located on a separate wearable device, such as a sensor on a band that can be worn around the arm, leg, neck, or chest, or a sensor implanted inside the body, which may communicate via a wired or wireless connection with the therapy unit and/or the monitoring unit.

In some embodiments, the monitor unit can instead be carried by the user in, for example, the user's hand or pocket, rather than be worn. For example, a monitor unit carried by the user can be a smart phone, such as an Android smartphone or iPhone.

In some embodiments, the two-part system or the monitor unit may instruct the user to perform an action, such as to sit and relax the arm, or to remain still or to attempt to remain still while the wearable monitor unit takes a measurement with one of the sensors.

In some embodiments, the user interface can include a display. In some embodiments, the display can be a touch screen display or capacitive sensor. In some embodiments, the display can be an array of LED lights. In some embodiments, the user interface can include one or more buttons, a dial, and/or a keyboard.

In some embodiments, the electrodes can be dry-contact (e.g., fabric, metal, silicone or any other plastic impregnated with conductive fillers, or a combination), use a conductive gel (e.g., hydrogels), or have a wet electrode surface (e.g., a sponge with water or conductive liquids or gels), or have fine micro needles, for example. In some embodiments, the electrodes can have a foam backing.

In some embodiments, the monitor unit can be a wearable monitor having a housing with a user interface. The housing can use a plurality of sensors to collect, store, and analyze biological measures about the wearer including, but not limited to, blood pressure, motion (e.g., accelerometers, gyroscopes, magnetometer, bend sensors), muscle activity (e.g., EMG using electrodes), cardiovascular rhythm measures (e.g., heart rate, heart rate variability, or ventricular and/or atrial dyssynchrony using electrodes to measure ECG, heart rhythm abnormalities), skin conductance (e.g., skin conductance response, galvanic skin response, using electrodes), skin temperature, pupil diameter, and sleep state (e.g., awake, light sleep, deep sleep, REM). Heart rhythm measures can be recorded with optical, electrical, and/or accelerometry-based sensors. In particular, studies have shown that increased stress levels can increase blood pressure. Activities such as exercise, can also affect onset of inflammatory bowel diseases or other inflammatory conditions—measuring accelerometry (motion), heart rate, etc. could help identify these activities and normalize the measurements by similar activities. Thus, using standard statistical analysis, machine learning, deep learning, or big data techniques, such as a logistical regression or Naïve Bayes classifier, these biological measures can be analyzed to assess a person's state, such as level of stress, which in turn, can serve as a predictor for inflammatory bowel disease or other inflammatory conditions. In some embodiments, the device can provide stimulation based on measurements of one or more biological measures, a determination of a person's state, and/or a prediction of inflammatory bowel disease or other inflammatory conditions.

In some embodiments, the responsiveness of stimulation could be dependent on one, two, or more sensors housed in the device to collect, store, and analyze biological measures about the wearer including, but not limited to, motion (e.g., accelerometers, gyroscopes, magnetometer, bend sensors), ground reaction force or foot pressure (e.g., force sensors or pressure insoles), muscle activity (e.g., EMG), cardiovascular measures (e.g., heart rate, heart rate variability (HRV), photoplethysmography (PPG), or ventricular and/or atrial dyssynchrony using electrodes to measure ECG and/or heart rhythm abnormalities), skin conductance (e.g., skin conductance response, galvanic skin response), respiratory rate, skin temperature, pupil diameter, and sleep state (e.g., awake, light sleep, deep sleep, REM). Using standard statistical analysis, machine learning, deep learning, or big data techniques, such as a logistical regression or a Naïve Bayesian classifier, these biological measures can be analyzed to assess the wearer's activity state, such as sedentary versus active, level of stress and the like, which in turn, can serve as a predictor inflammatory bowel disease or other inflammatory conditions.

Figure 13C:
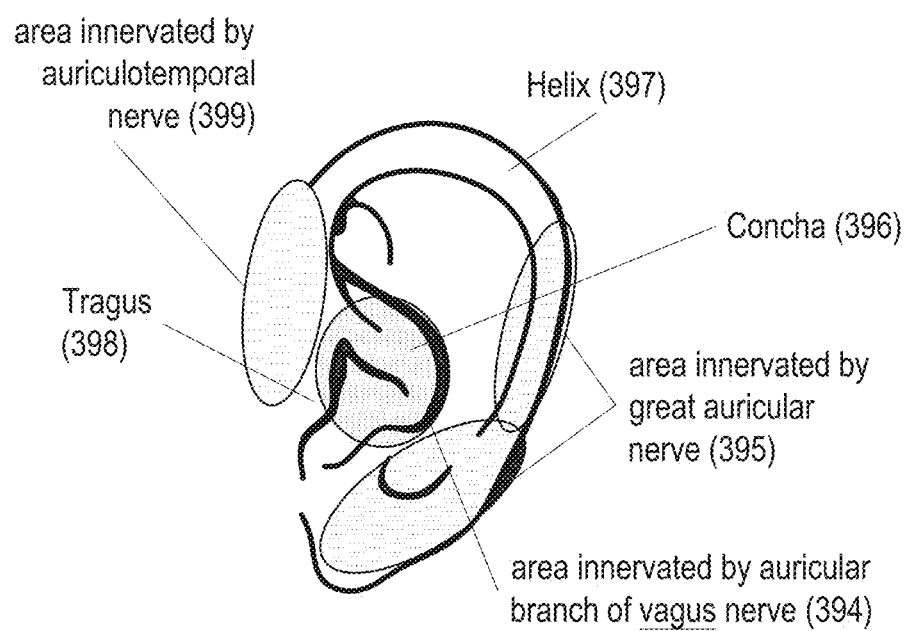
FIG. 13C schematically illustrates selected anatomy relating to the ear, including the area innervated by the auricular branch of the vagus nerve (ABVN).

In some embodiments, stimulation of one, two, or more nerves in the upper and/or lower extremity can be combined with stimulation of the ABVN, such as by way of the cymba concha or tragus, to modulate vagal activity and restore balance of the autonomic nervous system. In some embodiments, the system can stimulate solely the ABVN. FIG. 13C illustrates select anatomy of the ear 390, including a relatively medial area of the ear 390 generally innervated by the auriculotemporal nerve 399, the tragus 398, the helix 397, the concha 396, an area innervated by the great auricular nerve 395 generally at the inferior and lateral edge of the ear, and an area innervated by the ABVN 394 more centrally and generally in the vicinity of the cymba concha or tragus 398. In some embodiments, systems and methods do not directly stimulate the cervical vagus nerve, and/or any nerve within the neck. In some embodiments, systems and methods do not involve trans-spinal stimulation, such as trans-spinal direct current stimulation. In some embodiments, systems and methods do not involve transcranial and/or peripheral magnetic stimulation. In some embodiments, systems and methods do not stimulate a nerve within the abdomen, such as any number of the splenic nerve, celiac plexus, celiac ganglion, aorticrenal ganglion, greater thoracic splanchnic nerve, and/or lesser thoracic splanchnic nerve.

Figure 13D:
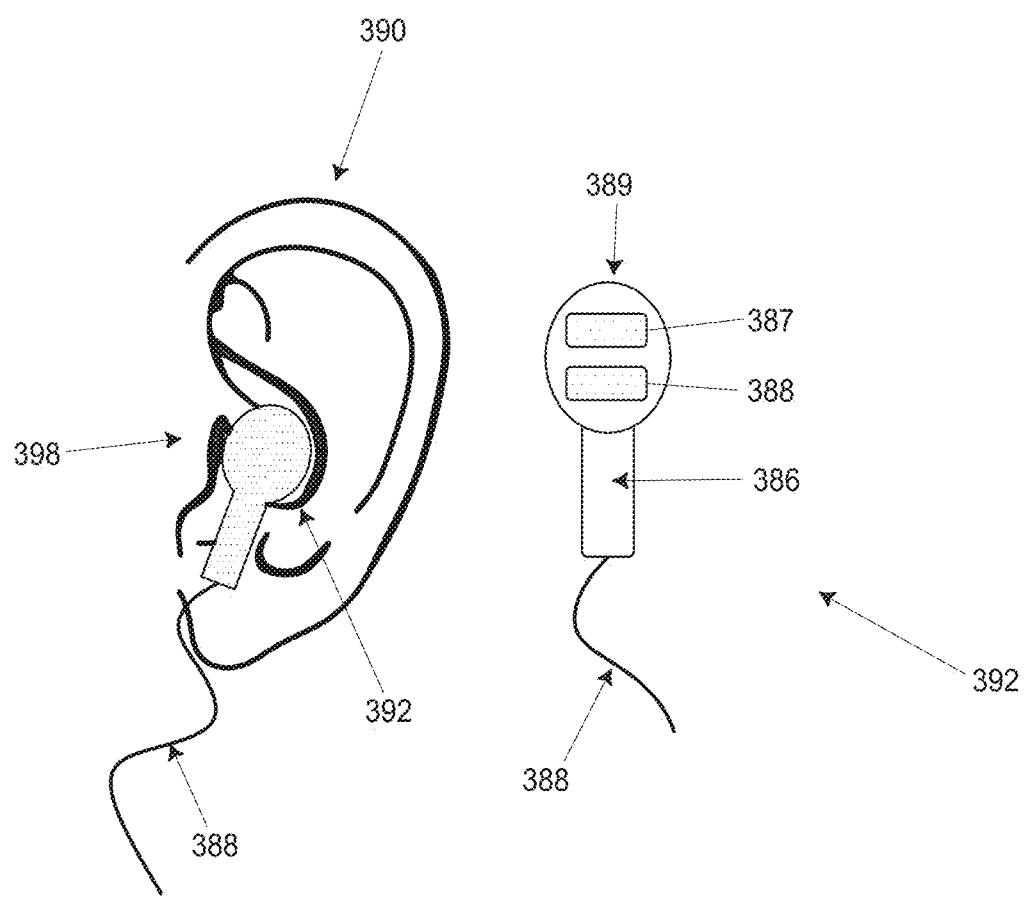
FIG. 13D illustrates an embodiment of an auricular stimulation device.
Figure 14A:
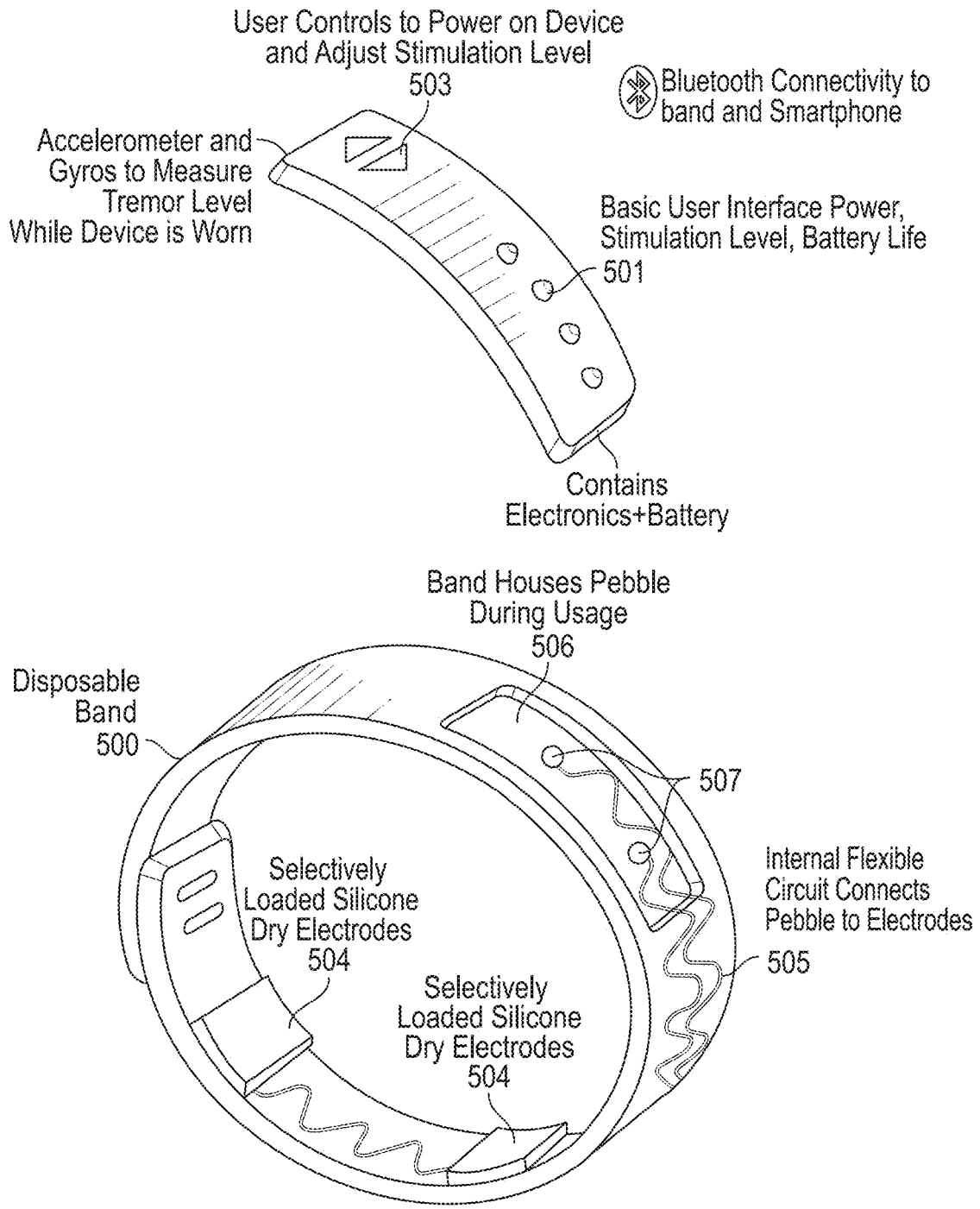

Stimulation of the cymba concha or tragus can occur, for example, noninvasively via a plug, earpiece, or other device that can include electrodes for transcutaneous electrical stimulation in some cases. FIG. 13D illustrates an embodiment of a tragus stimulator 392 with an earbud configuration positioned in the tragus 398 of the ear 390. The stimulator 392 can be wired as shown, or wireless in other embodiments. The stimulator 392 can include a distal ear receptacle portion 389 that can include a cathode 387 and an anode 388, a hub 386 proximate the receptacle portion 389, and a conduit 388 to a source of electromagnetic energy, such as electrical energy. In some embodiments, the auricular stimulator 392 includes one or more sensors for measuring parameters relating to stimulation and/or physiologic function as discussed elsewhere herein. The auricular stimulator 392 can be unilateral or bilateral (e.g., placed in both ears).

In some embodiments, a system can include a plurality of stimulators that communicate with each other wirelessly and provided a synchronized, patterned stimulation. In some embodiments, multiple stimulators may be in electrical connection with multiple electrode pairs to stimulate multiple nerves simultaneously. In one embodiment, a system can include a stimulator on the wrist to target median nerve and a stimulator in the ear to target the ABVN. Each stimulator in the system can communicate with each other via a wired or wireless connection. Multiple stimulators can provide synchronized stimulation to the multiple nerves. Stimulation may be, for example, burst, offset, or alternating between the multiple nerves.

The device could also be responsive to number of episodes of symptoms, including but not limited voiding, incontinence, sense of urgency, nocturia, abdominal or intestinal pain. If more episodes occur in one day, treatment can be increased by increasing the amplitude of the stimulation, duration of the stimulation, or number of treatment sessions, for example.

The number of episodes of symptoms could be detected in various ways to control the stimulation applied by system and devices. In some embodiments, the patient can enter events related to symptoms, including but not limited voiding, incontinence, sense of urgency, nocturia, abdominal or intestinal pain.

One embodiment of the system could centrally store biological measures from multiple wearers on a server system (e.g., the cloud), along with other relevant demographic data about each user, including age, weight, height, gender, ethnicity, etc. Data collected from multiple wearers can be analyzed using standard statistical analysis, machine learning, deep learning, or big data techniques, such as a logistic regression or Naive Bayes classifier (or other classifiers), to improve prediction of episodes of inflammatory bowel disease or other inflammatory conditions by determining correlations between biological measures and other recorded symptom events associated with the treated disease. These correlations can be used to set parameters of the stimulation waveform applied by the therapy unit, determine best time to apply stimulation therapy, and/or adapt the stimulation waveform applied by the therapy unit in real time.

In one embodiment of the system, the wearable monitor automatically detects and records the dosage and consumption of medications to (1) track compliance of the patient; (2) combine with the logging of symptom events to assess therapeutic effectiveness, and (3) determine or predict unpleasant symptoms associated with inflammatory bowel disease or other inflammatory diseases. The dosage and consumption of medications can be detected and recorded in multiple ways, including (1) using a visual scanner to record a marking on the pill pack or bottle each time medication is consumed, (2) a smart pill cap with force sensors and a wireless transmitter to detect each time the medication is consumed from a pill bottle, (3) an RFID chip that is of similar size and shape as a pill that is consumed with each dosage of medication that is activated by digestion and communicates with the monitor device, (4) an RFID chip embedded in a sugar pill that is consumed with each dosage of medication that is activated by digestion and communicates with the monitor device, (5) a pill with a visual encoding that is scanned and recorded by a camera on the monitor unit each time medication is consumed, or (6) by having the patient logging drug consumption into the device.

The system can also log the patient satisfaction after each stimulation session or the end of a specified period, like a day or week or month, via an input on the device, which provides another piece of information to help feedback application of therapy. In some cases, if a person is satisfied, the therapy is maintained at the current stimulation waveforms and levels. In other cases, this may mean that the stimulation treatment may need to be optimized, for example, by changing stimulation parameters such as waveform frequency or amplitude.

In some embodiments, the wearable monitor can have a visual, auditory, tactile (e.g., squeezing band), or vibrotactile cues to notify the wearer of key events based on analysis of biological measures, including, but not limited to, prediction of symptoms caused by inflammatory bowel diseases or other inflammatory conditions, and/or increase in stress level, heart rate, heart rate variability, or other parameters. The cuing system could also notify the wearer of other predetermined events or reminders set by the wearer.

In some embodiments, the form of the wearable monitor and/or therapy unit could be a wrist band or watch, a ring, a glove, an arm sleeve or arm band or cuff, knee band, sock, leg sleeve or cuff, an ear piece/headphone, head band, a necklace or neck band, or a compliant patch that conforms to multiple locations on the body.

In one embodiment, the wearable monitor can have a processing unit and memory that collects, stores, processes, and analyzes the biological measures, along with other data input by the wearer.

In some embodiments, the wearable monitor can take user input about events, including diet history, medication history, caffeine intake, alcohol intake, sodium intake, etc. The monitor can use accelerometers to measure specific movements, gestures, or tapping patterns to record user inputs at specific prompts. Other touch sensors, such as resistive strips or pressure sensitive screens, could be used to measure specific gestures to record user inputs. These gesture-based measures to record user input minimize the complexity of steps required to input user data into the device. The data can be stored in memory and processed by the processing unit. In some embodiments, the data can be transmitted from the wearable monitor to an external computing device.

In one embodiment, the wearable monitor and/or the therapy unit can connect with other applications, such as calendars and activity logs, to sync and track events or a saved calendar can be saved and stored on the device. In some embodiments, the wearable monitor and/or the therapy unit can communicate with a variety of computing devices, such as a smart phone, a smart watch, a tablet, a laptop computer, or a desktop computer, for example, that have these applications. In some embodiments, the wearable monitor can include an ambulatory blood pressure monitor.

In one embodiment, the monitor unit and/or therapy unit can have a GPS or similar device to track the location and assess activity of the wearer. GPS measures can be combined with mapping or location systems to determine context of the wearer's activity (e.g., gym, office, home) or determine changes in elevation during specific activities, such as running or cycling.

FIGS. 14A-14E illustrates another embodiment of a two-part therapy system that includes a disposable band 500 and a therapy unit 502 that can be reversibly attached to the disposable band 500. The disposable band 500 can have two or more electrodes 504 disposed on a skin facing or inside surface of the band and a receptacle 506 or receiving portion for reversibly receiving the therapy unit 502. Within the band 500 are wires and/or conductive traces that form a flexible circuit 505 that runs from the electrodes 504 to the receptacle 506 for electrically connecting the electrodes 504 to the therapy unit 502 when the therapy unit 502 is disposed in the receptacle 506. In some embodiments, the wires and/or conductive traces of the flexible circuit 505 are arranged in a wave or undulating pattern in order to improve its ability to flex. In some embodiments, the receptacle 506 can have one or more electrical contact points, such as one or more pin holes 507, for receiving one or more complementary electrical contacts, such as pins 509, from the therapy unit 502. The flexible circuit 505 can extend to the pin holes 507 such that an electrical connection is formed when the pins are inserted into the pin holes. The electrodes 504 can be dry electrodes or can be coated with a conductive gel.

In some embodiments, the therapy unit 502 can include a battery, which may be rechargeable, and electronics to deliver electrical stimulation through the electrodes to the patient's nerves. The electronics can include a stimulator and a microcontroller, and may also include memory and one or more sensors, such as a blood pressure sensor and/or a sensor to measure heart rate and/or heart rate variability and/or galvanic skin response, or one, two, or more ECG electrodes to measure dyssynchrony. In some embodiments, the device is able to sense the impedance of the electrodes in order to assess the integrity of the electrode to skin interface. In some embodiments, there can be an electrical indication (e.g. reading of a chip, pushing in of a sensor on the connector, etc.) to detect integrity of the connection between the band and the therapy unit. In some embodiments, the therapy unit 502 can have one or more LEDs, mini OLED screens, LCS, or indicators 501 that can indicate the status of the therapy unit 502, such as whether the therapy unit 502 is connected to the band 500, the power remaining in the battery of the therapy unit 502, whether a stimulation is being delivered, the stimulation level, whether data is being transmitted, whether a sensor measurement is being taken, whether a calibration routine is being performed, whether the therapy unit 502 is initializing, whether the therapy unit 502 is paired with another device such as a smart watch and/or smart phone, whether the battery is being charged, and the like. In some embodiments, the therapy unit 502 may also include a user interface 503, such as one or more buttons.

FIG. 14B illustrates a kit including a wrist worn device that can be sent to a user. The kit can contain a plurality of bands 500 of different sizes, shapes, colors, etc. to accommodate patients having different wrist sizes or other body part sizes, such as ankles, arms, fingers, and legs and to accommodate different types of connected accessories like secondary displays (e.g. smart watch). In some embodiments, the kit has three bands to accommodate a majority of wrist sizes. In some embodiments, the kit has two bands to cover most sizes. Additionally, the kit can contain one or more electronic units 502. If multiple electronic units 502 are provided in the kit, the battery capacity of the different electronic units 502 can be different to accommodate different usage types. For example, a relatively low capacity battery can be used for on-demand stimulation, while a relatively high capacity battery can be used for automated and/or responsive stimulation driven by the microcontroller. In some embodiments, only a single electronic unit is provided. In other embodiments, a plurality of electronic units are provided while a single band is provided. The kit may also include a charger 508 to charge the therapy unit 502. In some embodiments, the charger 508 can inductively charge the therapy unit 502. In other embodiments, the charger 508 can charge the therapy unit with a charge cable that can be inserted into a power port in the therapy unit. In some embodiments, the therapy unit 502 can be docked with the charger 508 for charging.

FIG. 14C illustrates an embodiment where a smart watch 510, such as the Apple Watch, is reversibly or permanently fastened to a band 500, which may also have a therapy unit 502. In some embodiments, the smart watch 510 may provide a display and a user interface for the therapy unit 502. The smart watch 510 may communicate with the therapy unit 502 wirelessly, such as through Bluetooth or Wi-Fi, or through a direct connection through a data port in the smart watch and a data port in the therapy unit 502. In some embodiments, the electronic unit 502 and/or smart watch 510 may communicate with a smart phone 512, as described herein, to transmit data or to update the software and/or stimulation parameters on the therapy unit 502 and/or smart watch 510. In some embodiments, the band 500 and therapy unit 502 are permanently affixed or integrated together while the smart watch 510 is reversibly attachable to the band 500. The smart phone 512 and/or the smart watch 510 can include an application, which may be downloaded through the cloud or a computer, configured to interface with the therapy unit 502.

FIGS. 14D and 14E illustrate that the wearable two-part system can be worn and used throughout the day. When the power remaining in the battery of the therapy unit is low, the therapy unit 502 can be recharged with the charger 508. Charging can be performed at night or whenever the battery is low or when desired. In some embodiments, the therapy unit can be removed from the band before charging. In some embodiments, the user can swap a low charge therapy unit with a high charged therapy unit so that the user can always be wearing a therapy unit.

In some embodiments, the kit illustrated in FIG. 14B can be used as a diagnostic trial kit. The patient can initially wear the therapy system for about, at least about, or no more than about 1 day to about 90 days, or about or at least about 1, 2, 3, 4, 5, 6, 9, 12, or more months, or for a predetermined length of time. This initial period is used to collect data with the sensors in the therapy unit and/or band in order to characterize the patient's symptomology, or other related measures, or other disease variables, and assess the patient's response to the therapy during the trial period in order to identify how well the patient is responding to the various treatments. The sensor data can be stored in memory in the therapy unit, and/or can be transmitted through a network to the cloud or a server or to another computing device, which can be accessed by the patient's physician, the company, or another third party.

Figure 15:
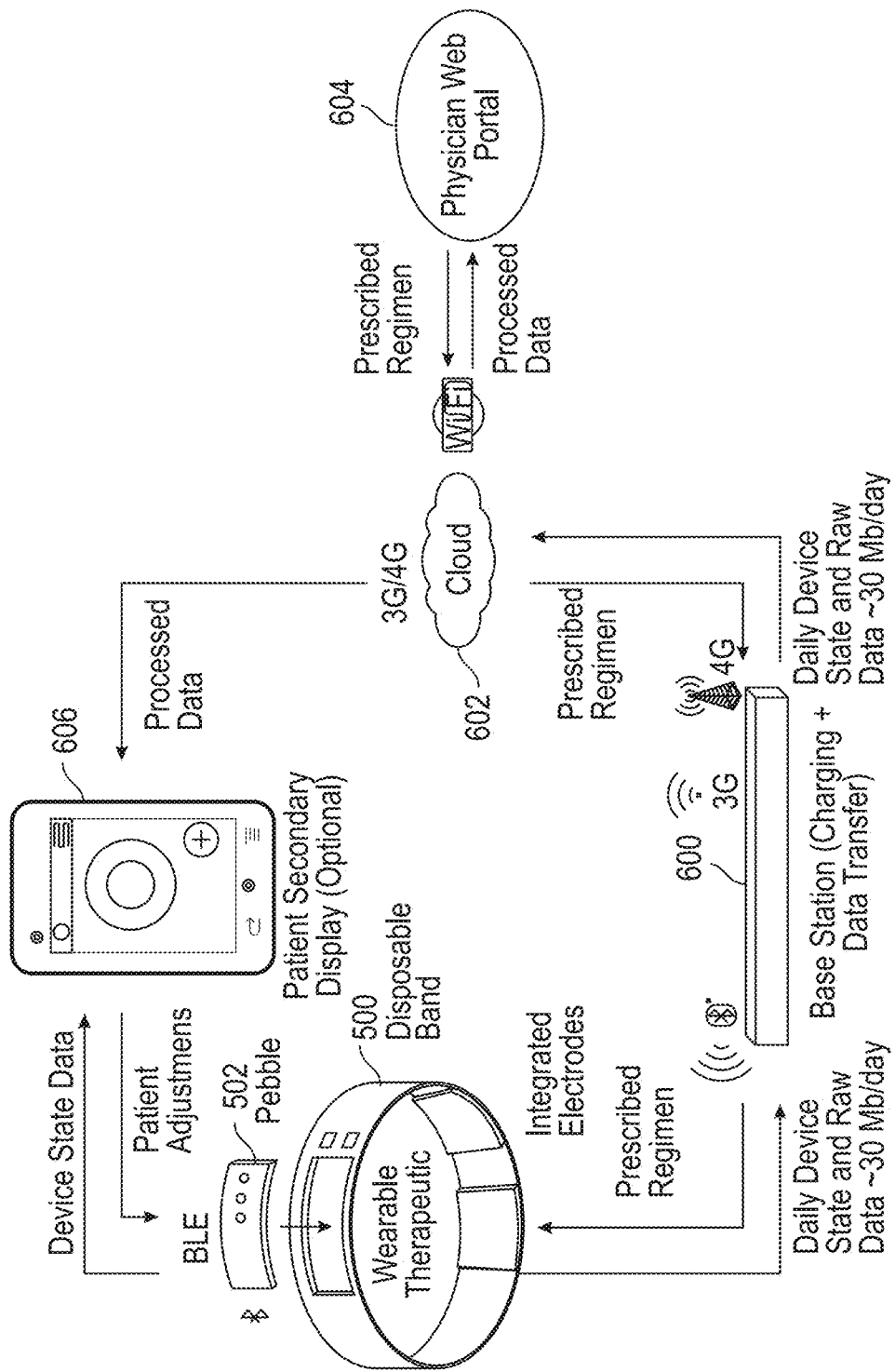
FIG. 15 illustrates an embodiment of the wearable therapy system that uses the cloud to receive and transmit data between the therapy system, a secondary patient device, and a physician.

FIG. 15 illustrates an embodiment of a system for treating inflammatory bowel disease or other conditions including those disclosed herein using a wearable therapy device. As described above, the therapy device may have two parts, a band 500 and therapy unit 502. A base station 600, which may replace the charger in the kit described above, can be used to both charge the therapy device and to receive and transmit data to the therapy device and to the cloud 602. Communication between the base station 600 and the therapy device can be wireless, such as through Bluetooth and/or Wi-Fi, and communication between the base station 600 and the cloud 602 can be through a cellular network, using a 3G or 4G connection, or through a wired connection to the internet, using DSL or cable or Ethernet, for example. A physician or other user can view and/or retrieve data stored on the cloud 602 using an online portal or a physician web portal 604. In addition, the physician can prescribe and/or modify a treatment regimen on the therapy unit 502 through the cloud 602 and base station 600 using the web portal 604.

In some embodiments, the base station 600 is used to receive and transmit relatively large amounts of data that may require a high bandwidth, such as the transmission of raw data from the therapy device, which may be about 10 to 100 Mb/day, or about 10, 20, 30, 40, or 50 Mb/day. In some embodiments, the data may be stored in memory in the base station 600 and transmitted at another interval, such as weekly or twice weekly, with a scaling up of the bandwidth of transmission. The high bandwidth transmission of the raw data can occur daily while the therapy device is being charged, such as at night during a regular charging period. In some embodiments, the raw data can be processed by the cloud and/or the physician into processed data and sent back to the therapy device.

In some embodiments, the system may optionally include a portable computing device 606, such as a smart phone or tablet, to provide a secondary display and user interface for the patient and to run applications to more easily control the therapy device and view the raw and processed data. The portable computing device can be used to make patient or physician adjustments to the therapy device, such as adjusting the stimulation parameters and dosing, and can receive device state data from the therapy device, which includes data relating to the device, such as when the device was used, errors, therapy parameters such as amplitude and when they were set and delivered. In some embodiments, the portable computing device 606 can receive processed data from the cloud 602 through a cellular network and/or through an internet connection using Wi-Fi, for example.

Figure 16:
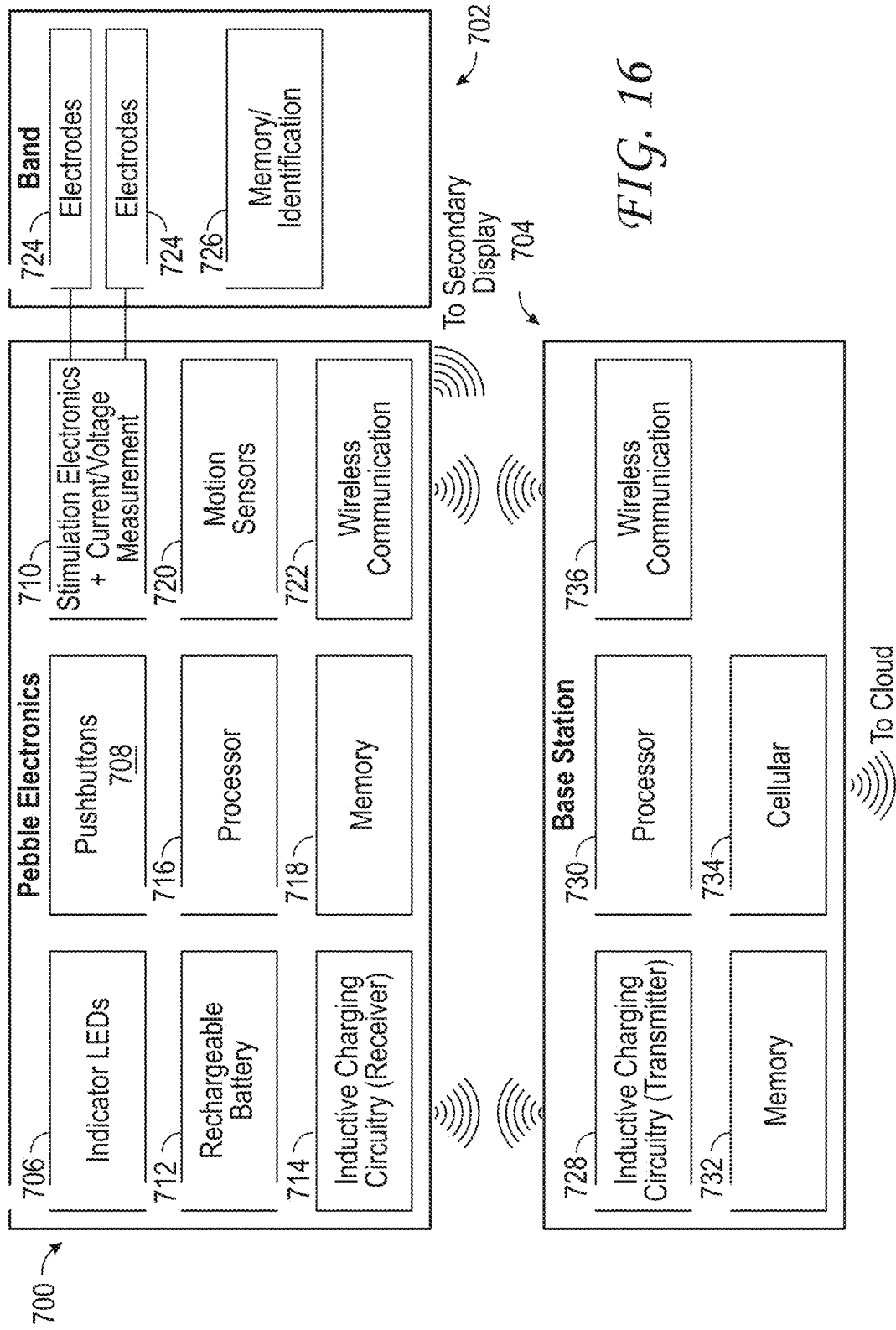
FIG. 16 is a block diagram that illustrates the individual components of the therapy unit, band, and base station shown in FIG. 15.

FIG. 16 illustrates the various components that can be included in a therapy unit 700, band 702, and base station 704. These components are described in detail above and also below as one particular embodiment. For example, the therapy unit 700 includes one or more indicators 706, which can be LEDs, and a user interface 708, which can be push buttons, for example. The therapy unit 700 can also have a stimulator 710 with stimulation electronics and may include the capability to measure current and voltage. The therapy unit 700 can also have a battery 712, which may be rechargeable and can be recharged using charging circuitry 714, which may be inductive. The therapy unit 710 may further include a processor 716 and memory 718 to store and execute programs and instructions to accomplish the functions described herein. The therapy unit 710 may also include sensors 720, such as blood pressure sensors, and a communications module 722, which may be wireless and can communicate with the base station 704 and/or a secondary display/computing device.

The band 702 can have electrodes 724 and may also include memory to store identification information or may include some other form of identifier 726 as described herein.

The base station 704 can include charging circuitry 728, which may also be inductive and can transmit power to the complementary charging circuitry 714 on the therapy unit 700. The base station 704 can also have a processor and memory for storing and executing instructions and programs. The base station 704 can further include a communication module 732, which may be cellular, to communicate with the cloud, and another communication module 734, which may be wireless and used to communicate with the therapy unit.

In some embodiments, the device can be a biological sensor, such as a heart rate monitor worn on the body, which could include an integrated nerve stimulator. In some embodiments, the nerve stimulator and sensor device can be separate devices that communicate wirelessly. In some embodiments, the device can measure a biological measurement over the course of minutes, hours, days, weeks and/or months to determine whether the patient's condition is increasing, decreasing, or staying the same. In some embodiments, the measurements are time averaged over a window, which can be days, weeks, or months. In some embodiments, a sensor, such as a motion sensor, IMU, or GPS, can be used to detect patient activity, which can affect other measurements. In some embodiments, the sensor can be an electrode that measures galvanic skin response, which can be correlated to stress, a known trigger for inflammatory exacerbations. In some embodiments, measurements are collected at the same time each day with the same conditions to improve measurement consistency and to reduce variability. In some embodiments, the stimulator is applied to one wrist or arm or ear to stimulate one peripheral nerve in the arm, such as the median nerve or ABVN, or specific nerve location, such as an acu-pressure point or meridians.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously stimulating an afferent peripheral nerve" includes "instructing the stimulation of an afferent peripheral nerve."

What is claimed is:

1. A method for treating symptoms of an inflammatory gastrointestinal disease in a patient with transcutaneous stimulation of a peripheral nerve comprising:
    positioning a first peripheral nerve effector on the patient's skin to stimulate the peripheral nerve of the patient;
    delivering a first electrical nerve stimulation signal transcutaneously to the peripheral nerve through the first peripheral nerve effector;
    receiving an input relating to activation of the first peripheral nerve;
    calculating one or more features from the input relating to activation at least based in part on a nerve conduction velocity of the first peripheral nerve;
    adjusting an electrical stimulation parameter based on one or more features of the nerve conduction velocity of the first peripheral nerve to selectively activate a first preselected nerve fiber type; and
    delivering the adjusted electrical stimulation pattern via an electrical nerve stimulation signal through the first peripheral nerve effector to affect at least one brain or spinal cord autonomic feedback loop relating to release of neurotransmitters from an autonomic nervous system that modulate synthesis of inflammatory biomarkers and reduce inflammation relating to the inflammatory gastrointestinal disease.

2. The method of claim 1, further comprising:
    positioning a second peripheral nerve effector on the patient's skin to stimulate a second peripheral nerve of the patient;
    delivering a second electrical nerve stimulation signal transcutaneously to a second peripheral nerve through the second peripheral nerve effector;
    adjusting an electrical stimulation parameter based on one or more features of a nerve conduction velocity of the second peripheral nerve to selectively activate a second preselected nerve fiber type; and
    modifying at least one brain or spinal cord autonomic feedback loop relating to release of neurotransmitters from the autonomic nervous system that modulate synthesis of inflammatory biomarkers and reduce inflammation relating to the inflammatory gastrointestinal disease.

3. The method of claim 1, wherein the preselected nerve fiber type is selected from the group consisting of: A-alpha, A-beta, A-delta, A-gamma, and B fibers.

4. The method of claim 1, wherein adjusting the electrical stimulation parameter comprises adjusting at least one of a pulse width or a pulse duration of the electrical stimulation to within about 10% of a chronaxie of the first preselected nerve fiber type.

5. The method of claim 1, wherein adjusting the electrical stimulation parameter comprises adjusting at least one of a pulse width or a pulse duration of the electrical stimulation to within about 5% of a chronaxie of the first preselected nerve fiber type.

6. The method of claim 1, wherein adjusting the electrical stimulation parameter comprises adjusting at least one of a pulse width or a pulse duration of the electrical stimulation to about a chronaxie of the first preselected nerve fiber type.

7. The method of claim 1, wherein the nerve conduction velocity is measured orthodromic ally.

8. The method of claim 1, wherein the nerve conduction velocity is measured antidromic ally.

9. The method of claim 2, wherein the first peripheral nerve and the second peripheral nerve do not directly innervate abdominal organs.

10. The method of claim 2, wherein the first peripheral nerve and the second peripheral nerve are not within an abdomen.

11. The method of claim 2, wherein the first peripheral nerve and the second peripheral nerve are not a cervical branch of a vagus nerve.

12. A wearable device for treating symptoms of an inflammatory gastrointestinal disease in a patient with transcutaneous stimulation of one or more peripheral nerves comprising:
a controller;
a first peripheral nerve effector, comprising at least one stimulation electrode configured to be positioned on the skin to stimulate a first peripheral nerve of the patient;
a first sensor or data input source, comprising at least one sensing electrode configured to be positioned on the skin to measure activity of the first peripheral nerve;
wherein the controller comprises a processor and a memory for receiving feedback information from one or more sensors that, when executed by the processor, cause the device to:
calculate one or more features of nerve conduction velocity of the first peripheral nerve based at least in part on the feedback information of the first sensor;
adjust one or more parameters of a first electrical stimulus based at least in part one or more features of nerve conduction velocity to selectively activate or maximize activation of a preselected fiber type in the first peripheral nerve; and
deliver a first electrical stimulus to a first peripheral nerve through the first peripheral nerve effector to modify at least one brain or spinal cord autonomic feedback loop relating to release of neurotransmitters from an autonomic nervous system that modulate synthesis of inflammatory biomarkers and reduce inflammation relating to the inflammatory gastrointestinal disease.

13. The device of claim 12, further comprising:
a second peripheral nerve effector, comprising at least one stimulation electrode configured to be positioned on the skin to stimulate a second peripheral nerve of the patient;
a second sensor or data input source, comprising at least one sensing electrode configured to be positioned on the skin to measure activity of the second peripheral nerve;
wherein the controller comprises a processor and a memory for receiving the feedback information from one or more sensors that, when executed by the processor, cause the device to:
calculate one or more features of nerve conduction velocity of the second peripheral nerve based at least in part on the feedback information of the second sensor;
adjust one or more parameters of a second electrical stimulus based at least in part one or more features of nerve conduction velocity to selectively activate or maximize activation of a preselected fiber type in the second peripheral nerve; and
deliver a second electrical stimulus to a second peripheral nerve through the second peripheral nerve effector to modify at least one brain or spinal cord autonomic feedback loop relating to release of neurotransmitters from the autonomic nervous system that modulate synthesis of inflammatory biomarkers and reduce inflammation relating to the inflammatory gastrointestinal disease.

14. The device of claim 12, wherein the preselected nerve fiber type is selected from the group consisting of: A-alpha, A-beta, A-delta, A-gamma, and B fibers.

15. The device of claim 12, wherein the controller is configured adjust at least one of a pulse width or a pulse duration of the electrical stimulation to within about 10% of a chronaxie of the first preselected nerve fiber type.

16. The device of claim 12, wherein the controller is configured adjust at least one of a pulse width or a pulse duration of the electrical stimulation to within about 10% of a chronaxie of the first preselected nerve fiber type.

17. The device of claim 12, wherein the controller is configured adjust at least one of a pulse width or a pulse duration of the electrical stimulation to about a chronaxie of the first preselected nerve fiber type.

18. The device of claim 12, wherein the device is configured such that the first peripheral nerve and the second peripheral nerve do not directly innervate abdominal organs.

19. The device of claim 12, wherein the device is configured such that, wherein the first peripheral nerve and the second peripheral nerve are not within the abdomen.

20. The device of claim 12, wherein the device is configured such that the first peripheral nerve and the second peripheral nerve are not a cervical branch of a vagus nerve.

* * * * *